United States Patent [19]

Yoshino et al.

[11] Patent Number: 5,250,549
[45] Date of Patent: Oct. 5, 1993

[54] SULFONAMIDE DERIVATIVES

[75] Inventors: Hiroshi Yoshino, Chiba; Norihiro Ueda, Ibaraki; Hiroyuki Sugumi, Ibaraki; Jun Niijima, Ibaraki; Yoshihiko Kotake, Ibaraki; Toshimi Okada, Ibaraki; Nozomu Koyanagi, Ibaraki; Tatsuo Watanabe, Osaka; Makoto Asada, Ibaraki; Kentaro Yoshimatsu, Ibaraki; Atsumi Iijima, Ibaraki; Takeshi Nagasu, Ibaraki; Kappei Tsukahara, Ibaraki; Kyosuke Kitoh, Ibaraki, all of Japan

[73] Assignee: Eisai Co., Ltd., Tokyo, Japan

[21] Appl. No.: 742,618

[22] Filed: Aug. 8, 1991

[30] Foreign Application Priority Data

Aug. 20, 1990 [JP] Japan ................... 2-218710
Mar. 5, 1991 [JP] Japan ................... 2-38509
May 27, 1991 [JP] Japan ................... 3-121041

[51] Int. Cl.$^5$ ............... C07D 213/74; C07D 213/75; C07D 213/76; A61K 31/44
[52] U.S. Cl. ................. 514/345; 514/348; 514/349; 514/352; 546/307; 546/22; 546/24
[58] Field of Search ........... 546/307, 22, 24; 514/352, 345, 348, 349

[56] References Cited

U.S. PATENT DOCUMENTS 2,202,933 6/1940 Tisza et al. ................ 546/307
2,307,650 1/1943 Tisza et al. ................ 546/307

OTHER PUBLICATIONS

Chemical Abstracts 96, 85186v, Simov et al.
Chemical Abstracts 99, 30703t, Gabrielsen et al.
Chemical Abstracts 100, 219086z, Konishiroku.
Chemical Abstracts 109, 110014j, 110, 38738z, 38739a, Hashimoto et al.
Chemical Abstracts 52, 18467d, Huisger et al.
Chemical Abstracts 54, 5522, Kloetzel et al.
Chemical Abstracts 54, 7650b, Johnson et al.
Chemical Abstracts 58, 5665h, Takeshi Ichii.
Chemical Abstracts 75, 140404h, Shine et al.
Chemical Abstracts 76, 14457k, Shirai et al.
Chemical Abstracts 78, 147777c, Werner.
Chemical Abstracts 79, 92103t, Mysyk et al.
Chemical Abstracts 81, 152199g, Nagarajan et al.
Chemical Abstracts 82, 16506y, Mysyk et al.
Chemical Abstracts 82, 170835m, Friedrichsen et al.
Chemical Abstracts 94, 65559z, Coutts et al.

*Primary Examiner*—C. Warren Ivy
*Assistant Examiner*—Phyllis Spivack
*Attorney, Agent, or Firm*—Flynn, Thiel, Boutell & Tanis

[57] ABSTRACT

Sulfonamide derivatives of the general formula (I):

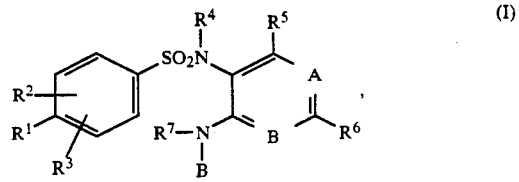

wherein preferably $R^1$ represents a lower alkoxy group, $R^2$, $R^3$, $R^4$, $R^5$, $R^6$ and $R^7$ are as defined in the specification, A and B may be the same or different from each other and each represents $=N-$ or $=CH-$, E represents an aromatic 6-membered cyclic group, which may have 1 or 2 nitrogen atoms in the ring, and may be substituted with 1 to 3 substituents which may be the same or different from one another with the proviso that a combination of $R^1$ which is a hydrogen atom, lower alkyl group, nitro group or amino group which may be protected, $R^2$ and $R^3$ which are each a hydrogen atom, A and B which are each $=CH-$ and E which is a phenyl group which may be substituted with 1 to 3 substituents G which may be the same or different from one another is excluded, or pharmacologically acceptance salts of them.

9 Claims, No Drawings

SULFONAMIDE DERIVATIVES

FIELD OF INDUSTRIAL APPLICATION

The present invention relates to new sulfonamide derivatives, processes for producing them and a medicinal composition containing the same as the active ingredient.

Chemotherapeutic agents for cancers used heretofore include various substances, for example, alkylating agents such as cyclophosphamide, antimetabolites such as methotrexate and fluorouracil, antibiotics such as adriamycin, mitomycin and bleomycin, those derived from plants such as vincristine and etoposide, and metal complexes such as cisplatin.

4-Aminobenzenesulfonamide derivatives (see Japanese Patent Publication No. 3093/1968), 2-sulfonylamide/quinoxaline derivatives (see Japanese Patent Laid-Open No. 426/1987) and m-AMSA derivatives (see J. Med. Chem., 18, 1110 (1975)) were reported as active antineoplastic compounds having a sulfonamide group.

Most of them have only a low effectiveness on human tumors, particularly solid tumors having a low growth rate, such as lung cancer or colon cancer, and exhibit serious adverse reactions. Under these circumstances, the development of a new medicine having only a low toxicity and an excellent antitumor activity is demanded.

An object of the present invention is to provide new sulfonamide derivatives having an excellent antitumor activity and only a low toxicity. Another object of the present invention is to provide a process for producing these compounds and a medicinal composition containing them as the active ingredient.

SUMMARY OF THE INVENTION

After intensive investigations made for the purpose of finding an antitumor compound having only a low toxicity as described above, the inventors have found that new sulfonamide derivatives, which will be described below, have an excellent antitumor activity and only a low toxicity. The present invention has been completed on the basis of this finding.

Thus the present invention relates to sulfonamide derivatives of the general formula (I) or pharmacologically acceptable salts of them:

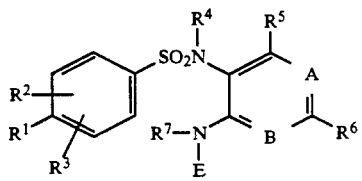

wherein:
$R^1$ represents a hydrogen atom, halogen atom, lower alkyl group, lower alkoxy group, hydroxyl group, nitro group, phenoxy group, cyano group, acetyl group or amino group, which may be protected,
$R^2$ and $R^3$ may be the same or different from each other and each represent a hydrogen atom, halogen atom, lower alkyl group or lower alkoxy group,
$R^4$ and $R^7$ may be the same or different from each other and each represent a hydrogen atom or lower alkyl group,
$R^5$ and $R^6$ may be the same or different from each other and each represent a hydrogen atom, halogen atom, lower alkoxyl group or amino group which may be substituted,
A represents a group of the formula: =N— or =CH—,
B represents a group of the formula:

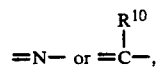

in which $R^{10}$ represents a hydrogen atom or lower alkyl group,
E represents a group of the formula:

in which Q represents an oxygen atom or sulfur atom and $R^{11}$ represents a hydrogen atom, lower alkyl group, amino group which may be substituted with a lower alkyl group, lower alkoxy group, 2-thienyl group, 2-furyl group or group of the formula:

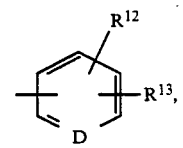

being a group of the formula: =N— or =CH—,
and $R^{12}$ and $R^{13}$ being the same or different from each other and each being a hydrogen atom, halogen atom, nitro group, hydroxyl group, which may be protected, or lower alkyl group; or an aromatic 6-membered cyclic group which may be substituted with 1 to 3 substituents G, which may be the same or different from one another, and which cyclic group may have 1 or 2 nitrogen atoms in the ring, G being a halogen atom, lower alkyl group, lower alkoxy group, hydroxyl group which may be protected, carboxyl group which may be esterified or amidated, lower alkylthio group or phenoxy group, with the proviso that the following combinations are excluded:

(1) a combination of $R^1$ which is a hydrogen atom, lower alkyl group, nitro group or amino group, which may be protected, $R^2$ and $R^3$ are each a hydrogen atom, A and B are each =CH— and E is a phenyl group which may be substituted with 1 to 3 substituents G, which may be the same or different from one another, and (2) a combination of $R^1$, $R^2$ and $R^3$, which may be the same or different from one another and which are each a hydrogen atom, lower alkyl group, nitro group or halogen atom, A and B are each =CH—,
and E is a group of the formula:

in which $R^{11}$ is a lower alkyl group, amino group, which may be substituted with a lower alkyl group, or a group of the formula:

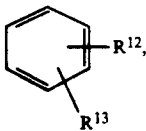

$R^{12}$ and $R^{13}$ being each as defined above.

The detailed description will now be made of the present invention.

The lower alkyl groups in the definition of $R^1$, $R^2$, $R^3$, $R^7$, $R^{10}$, $R^{11}$, $R^{12}$, $R^{13}$ and the substituent G which may be substituted in the definition of E of the above general formula (I) include straight-chain and branched alkyl groups having 1 to 6 carbon atoms, such as methyl, ethyl, n-propyl, isopropyl, n-butyl, isobutyl, sec-butyl, tert-butyl, n-pentyl (amyl), isopentyl, neopentyl, tert-pentyl, 1-methylbutyl, 2-methylbutyl, 1,2-dimethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl groups. Among them, methyl, ethyl, propyl and isopropyl groups are preferred, with methyl and ethyl groups being most preferred.

The lower alkoxy groups in the definition of $R^1$, $R^2$, $R^3$, $R^5$, $R^6$, $R^{11}$ and the substituent G which may be substituted in the definition of E are those derived from the above-described lower alkyl groups, such as methoxy, ethoxy, n-propoxy, isopropoxy, n-butoxy, isobutoxy and t-butoxy groups. Among them, the most desirable are methoxy and ethoxy groups. The halogen atoms include fluorine, chlorine and bromine atoms.

The substituted amino groups in the definition of $R^5$ and $R^6$ include amino groups substituted with a lower alkyl group, such as methylamino, ethylamino and dimethylamino groups, and amino groups substituted with a phenyl group.

The hydroxyl groups which may be protected of the substituent G, which may be substituted in the definition of E, include hydroxyl, methoxymethyloxy, tetrahydropyranyloxy, benzyloxy, phosphoric ester, sulfuric ester, sulfonic ester, such as an ester of p-methoxybenzenesulfonic acid or methanesulfonic acid, amino acid ester, such as an ester of glycine, alanine, leucine, tyrosine, aspartic acid, glutamic acid, lysine, arginine, proline, sarcosine, β-alanine or γ-aminobutyric acid, glycoside, such as glucoside and glucuronide, carbamoyloxy which may be substituted with a lower alkyl, such as carbamoyloxy, methylcarbamoyloxy and dimethylcarbamoyloxy, lower acyloxy having 1 to 5 carbon atoms, such as formyloxy, acetoxy, propionyloxy and pivaloyloxy and benzoyloxy.

The aromatic ring of the benzoyloxy group may be, if desired, substituted with a lower alkyl group such as a methyl, ethyl, n-propyl or isopropyl group, a lower alkoxy group such as a methoxy, ethoxy, n-propoxy or isopropoxy group, a halogen atom such as a fluorine, chlorine or bromine atom or an amino group which may be substituted with a lower alkyl group.

The amino groups which may be protected in the definition of $R^1$ include unsubstituted amino group, lower acylamino groups having 1 to 4 carbon atoms, such as formylamino, acetamino and propionylamino groups, and benzyloxycarbonylamino group.

The carboxyl groups which may be esterified or amidated in the definition of the substituent G which may be substituted in the definition of E include carboxyl group, lower alkoxycarbonyl groups having 2 to 5 carbon atoms, such as methoxycarbonyl, ethoxycarbonyl and isopropyloxycarbonyl groups, unsubstituted aminocarbonyl group, and aminocarbonyl groups substituted with an alkyl group having 1 to 4 carbon atoms, such as methylaminocarbonyl, ethylaminocarbonyl and dimethylaminocarbonyl groups.

The sulfonamide derivatives represented by the above general formula (I) may form a salt with an acid or base. The salts of the compounds (I) are also included in the present invention. Examples of the salts of them with an acid include inorganic acid salts such as hydrochloride, hydrobromide and sulfate as well as organic acid salts such as acetate, lactate, succinate, fumarate, maleate, citrate, benzoate, methanesulfonate and p-toluenesulfonate. Examples of the salts of them with a base include inorganic salts such as sodium, potassium and calcium salts and salts with organic bases such as triethylamine, arginine and lysine.

As a matter of course, hydrates of these compounds and optical isomers, if present, are also included in the present invention. The compounds of the present invention exhibit a potent antineoplastic activity. Compounds which exhibit an antineoplastic activity upon undergoing metabolism such as oxidation, hydrolysis or conjugation in vivo are also included in the present invention.

The compounds (I) of the present invention can be produced by various processes. Typical processes among them are as follows:

(1) A sulfonic acid of the general formula (II) or its reactive derivative:

Chemical formula 14

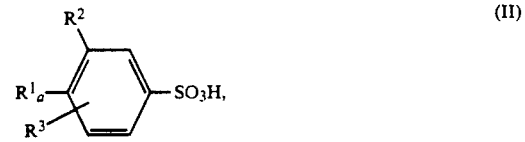

(II)

wherein $R^2$ and $R^3$ are as defined above and $R^1_a$ represents a hydrogen atom, halogen atom, or lower alkyl, lower alkoxy, protected hydroxyl, nitro, phenoxy, cyano, acetyl or protected amino group, is reacted with a compound of the general formula (III):

Chemical formula 15

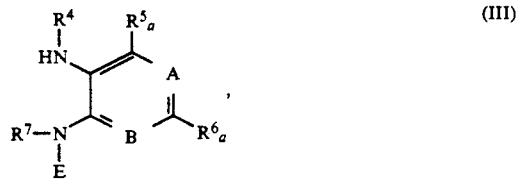

(III)

wherein $R^4$, $R^7$, A, B and E are each as defined above, and $R^5_a$ and $R^6_a$ may be the same or different from each other and each represent a hydrogen or halogen atom, lower alkoxy, or protected or substituted amino group.

The reactive derivatives of the sulfonic acids (II) include those usually used, such as sulfonyl halide, sulfonil anhydride and N-sulfonylimidazolide. Among them, particularly preferred is sulfonyl halide. The reaction proceeds when they are used in stoichiometrically equimolar amounts. Although the solvents used for the reaction are not particularly limited, desirable solvents are those in which the starting materials are soluble and which do not easily react with the starting materials. The solvents are, for example, pyridine, tetrahydrofuran, dioxane, benzene, ether, methylene chloride, dimethylformamide and mixtures of two or more of them. When an acid is liberated as the reaction proceeds, as in the case a sulfonyl halide, the reaction is desirably conducted in the presence of a suitable acid binder. Therefore, the use of a basic solvent such as pyridine is particularly preferred. When a neutral solvent is used, a basic substance such as an alkali carbonate or an organic tertiary amine may be added. As a matter of course, the solvents usable herein are not limited to those described above. The reaction usually proceeds at room temperature and, if desired, may be conducted under cooling or heating. The reaction time usually ranges from 10 min to 20 h. It is suitably determined depending on the varieties of the starting compounds and reaction temperature.

When the amino, hydroxyl or carboxyl group in the resulting sulfonamide derivative (I) is protected, it can be subjected to an ordinary method of removing protective groups, such as an acid treatment, alkali treatment or catalytic reduction, if desired, to obtain a compound (I) having a free hydroxyl, amino or carboxyl group.

(2) A compound of the general formula (IV)

Chemical formula 16

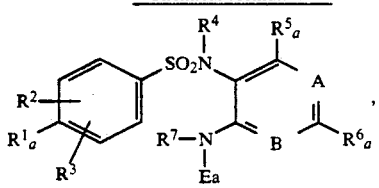

(IV)

wherein $R^1_a$, $R^2$, $R^3$, $R^4$, $R^5_a$, $R^6_a$, $R^7$, A and B are each as defined above, and Ea represents an aromatic 6-membered cyclic group, which may contain 1 or 2 nitrogen atoms in the ring, substituted with 1 to 3 substituents Ga which may be the same or different from one another, Ga being a halogen atom, lower alkyl group, lower alkoxy group, hydroxyl group, carboxyl group, which may be esterified or amidated, lower alkylthio group or phenoxy group, with the proviso that at least one Ga on the ring is a hydroxyl group,
is reacted with a compound of the general formula (V):

$$X-Y \quad (V)$$

wherein X represents a group capable of bonding with the oxygen atom of the hydroxyl group and Y represents a removable group,
or with an inorganic acid or organic acid anhydride reactive with the hydroxyl group.

X—Y include reactive derivatives of aromatic and aliphatic sulfonic acids, aromatic and aliphatic carboxylic acids, amino acids which may be protected, phosphoric acid which may be protected, sulfuric acid which may be protected, carbamic acid which may be substituted with a lower alkyl group and saccharides which may be protected. Examples of them include p-methoxybenzenesulfonyl chloride, methanesulfonyl chloride, o-chlorobenzoyl chloride, acetyl chloride, N-(t-butoxycarbonylaminoacetyl)imidazole, phosphorus oxychloride, chlorosulfonic acid, N,N-dimethylcarbamoyl chloride and methyl 1,2,3,4-tetra-O-acetyl-D-glucuronate. Examples of the anhydrides include inorganic acid anhydrides, such as diphosphorus pentoxide and sulfur trioxide, as well as organic acid anhydrides, such as N-carboxy anhydrides (NCA) of α-amino acids and isatoic anhydride.

Although the solvents used in the reaction are not particularly limited, desirable solvents are those in which the starting materials are soluble and which do not easily react with the starting materials. The solvents are, for example, pyridine, tetrahydrofuran, dioxane, benzene, ether, methylene chloride, dimethylformamide and mixtures of two or more of them. When a liquid starting compound such as phosphorus oxychloride is used, the reaction can be conducted without using any solvent.

(3) A compound of the general formula (VI):

Chemical formula 17

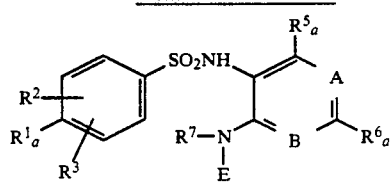

(VI)

wherein $R^1_a$, $R^2$, $R^3$, $R^5_a$, $R^6_a$, $R^7$, A, B and E are each as defined above,
is reacted with a compound of the general formula:

$$R^4_a-L$$

wherein $R^4_a$ represents a lower alkyl group and L represents a halogen atom,
in the presence of a base such as sodium hydride.

(4) A compound of the general formula (VII):

Chemical formula 18

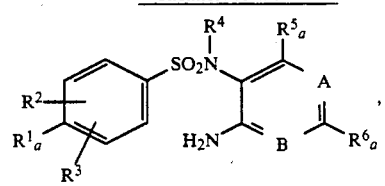

(VII)

wherein $R^1_a$, $R^2$, $R^3$, $R^4$, $R^5_a$, $R^6_a$, A and B are each as defined above,
is reacted with a compound of the general formula (VIII):

$$R^{11}-Z \quad (VIII)$$

wherein $R^{11}$ is as defined above, and Z represents a carboxyl group or its reactive derivative,
or when $R^{11}$ is a lower alkylamino group, it is reacted with a lower alkyl isocyanate.

The reactive derivatives of the carboxylic acids usable herein are, for example, acid halides, acid anhydrides, active amide compounds and active esters.

Examples of the acid halides usable herein are, for example, acid chlorides and acid bromides. The acid anhydrides usable herein are, for example, mixed monoalkylcarbonic acid anhydrides, mixed acid anhydrides comprising aliphatic carboxylic acids, such as acetic acid, pivalic acid, valeric acid, isovaleric acid and trichloroacetic acid, mixed aromatic carboxylic acids, such as benzoic acid, and symmetric acid anhydrides.

The active amide compounds usable herein are, for example, amides of acids with imidazole, pyrazole, 4-substituted imidazole, dimethylpyrazole, triazole, tetrazole and benzothiazole. The active esters are suitably selected from among methyl esters, methoxymethyl esters, cyanomethyl esters, propargyl esters, 4-nitrophenyl esters, 2,4-dinitrophenyl esters, trichlorophenyl esters, pentachlorophenyl esters, methanesulfonylphenyl esters, phenylazophenyl esters and esters with 1-hydroxy-1H-2-pyridone, N-hydroxysuccinimide, N-hydroxyphthalimide or 1-hydroxybenzotriazole.

The carboxylic acid (VIII) can be reacted with the amine (VII) in the presence of a condensing agent such as N,N'-dicyclohexylcarbodiimide (DCC) or N-cyclohexyl-N'-morpholinoethylcarbodiimide.

When $R^{11}$ is an amino group substituted with a lower alkyl group, the amine (VII) may be reacted with a lower alkyl isocyanate. When $R^{11}$ is an amino group, the amine (VII) may be reacted with an alkali metal salt of cyanic acid.

These reactions can be conducted in the presence of a base such as an organic tertiary amine, e.g. triethylamine, N,N-dimethylaniline or pyridine, alkali carbonate or alkali hydrogencarbonate or an acid, if necessary. The reaction proceeds when the reactants are each used in a stoichiometrically equimolar amount. Although the solvents used in the reaction are not particularly limited, desirable solvents are those in which the starting materials are soluble and which do not easily react with the starting materials. The solvents are, for example, pyridine, tetrahydrofuran, dioxane, benzene, ether, methylene chloride, dimethylformamide and mixtures of two or more of them. When a reagent difficultly soluble in the organic solvent, such as a cyanate, is used, the reaction may be conducted under hydrous conditions. The solvents usable herein are not limited to those described above. The reaction temperature is not particularly limited so far as the reaction proceeds. It is usually room temperature and, if desired, the reaction may be conducted under cooling or heating. The reaction time usually ranges from 5 min to 20 h. It is suitably determined depending on the varieties of the starting compounds and reaction temperature. When the product has a protected hydroxyl or amino group, it can be subjected to an ordinary method of removing protective groups, such as an acid treatment, alkali treatment or catalytic reduction to obtain a compound (I) having a free hydroxyl or amino group. When the product has a nitro group, this group may be converted into an amino group by reducing it by an ordinary method of reducing nitro groups, such as catalytic reduction conducted in the presence of a palladium/carbon catalyst or a method wherein zinc powder and hydrochloric acid are used.

Next the description will be made on the processes for producing the starting compounds (IX) used in the present invention:

Chemical formula 19

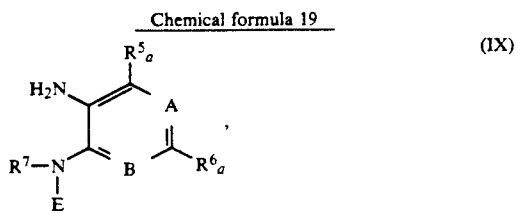
(IX)

wherein $R^5_a$, $R^6_a$, $R^7$, A, B and E are each as defined above,
or salts of them.

Production process 1

Chemical formula 20

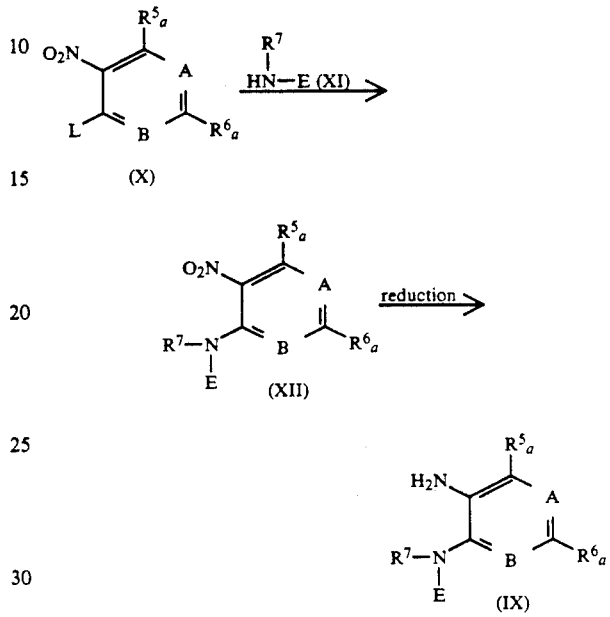

wherein L represents a halogen atom and $R^5_a$, $R^6_a$, $R^7$, A, B and E are each as defined above.

The compounds of the general formula (XII) can be synthesized by various processes described in publications such as J. Med. Chem., Vol. 21, p. 965, J. Org. Chem., Vol. 28, p. 3114, J. Chem. Soc. Perkin I, 1974, 1611, 1974, 1970 and 1979, 135, Helv. Chim. Acta, Vol. 61, p. 2452 or processes analogous to them. Namely, they can be produced by reacting a compound of the general formula (X) with a compound of the general formula (XI) in the presence or absence of an organic solvent, such as dimethylformamide, ethanol or dioxane, at room temperature or under heating.

When it is desired to remove a hydrogen halide thus formed, an organic base such as triethylamine or pyridine or an alkali carbonate is added as a acid binder or the reaction is conducted by using at least two equivalents of the compound (XI) per equivalent of the compound (X). When the product (XII) has a highly reactive halogen atom on its aromatic ring, it can be further reacted with an alkoxide or amine to convert it into another compound. The compound of the general formula (IX) can be obtained by reducing the compound (XII) produced as described above by an ordinary process for reducing nitro groups. In a preferred example of the reduction processes, catalytic reduction is conducted in the presence of a palladium/carbon catalyst or the reduction is conducted by using zinc powder and acetic acid. The catalytic reduction can be conducted usually in an organic solvent such as methanol, tetrahydrofuran or dimethylformamide under atmospheric or elevated pressure.

Production process 2

Chemical formula 21

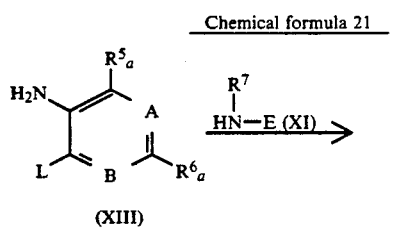

(XIII)

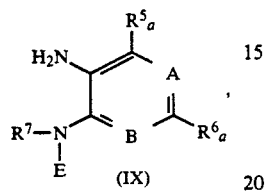

(IX)

wherein $R^5{}_a$, $R^6{}_a$, $R^7$, A, B, E and L are each as defined above.

The compounds represented by the general formula (IX) can be synthesized by, for example, a process described in J. Org. Chem., Vol. 24, p. 1314, a process described in J. Heterocycl. Chem., Vol. 20, p. 1339, or a process analogous to them. Namely, they can be produced by reacting a compound of the general formula (XIII) with a compound of the general formula (XI) in the presence of an acid catalyst, such as hydrochloric acid or sulfuric acid in a solvent such as water, ethanol or diethylene glycol. For increasing the reaction velocity, it is advantageous to heat the reaction mixture.

Production process 3

Chemical formula 22

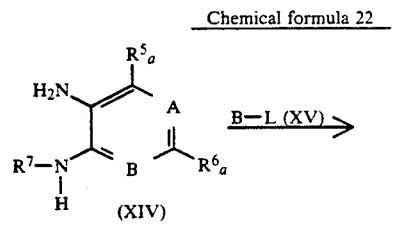

(XIV)

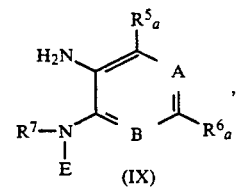

(IX)

wherein $R^5{}_a$, $R^6{}_a$, $R^7$, A, B, E and L are each as defined above.

The compounds represented by the general formula (IX) can be synthesized by, for example, a process described in J. Chem. Soc. (C) (1970), p. 1355 or a process analogous to it. Namely, they can be produced by reacting a compound of the general formula (XIV) with a compound of the general formula (XV) in the presence or absence of an organic solvent such as dimethylformamide or dioxane at room temperature or under heating.

Production process 4

Chemical formula 23

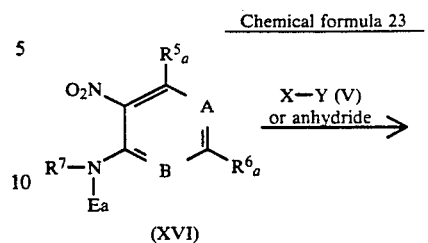

(XVI)

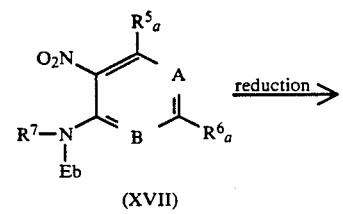

(XVII)

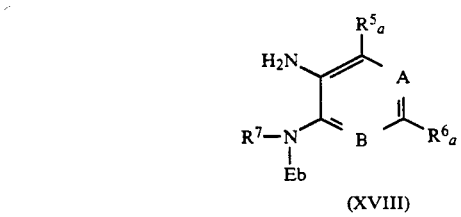

(XVIII)

wherein $R^5{}_a$, $R^6{}_a$, $R^7$, A, B and Ea are each as defined above and Eb represents E defined above in which at least one G is a protected hydroxyl group.

The compounds represented by the general formula (XVII) can be produced by reacting a compound of the general formula (XVI) with a compound of the general formula: X—Y (V), wherein X and Y are as defined above or with an inorganic acid or organic acid anhydride reactive with the hydroxyl group. The reaction conditions vary depending on the varieties of X—Y (V) and the anhydride. The reaction solvent is preferably an inert solvent which is not reactive with these compounds, such as dimethylformamide, tetrahydrofuran or dioxane. To increase the reaction velocity, a base such as sodium hydride, potassium carbonate or triethylamine may be added to the reaction system or the reaction system may be heated. When $R^7$ is a hydrogen atom, it is sometimes preferred to protect it with an ordinary amino-protective group such as a benzyloxycarbonyl group prior to the reaction with X—Y (V) or the anhydride and to remove the protective group after the completion of the reaction. The compounds represented by the general formula (XVIII) can be produced by reducing the compounds (XVII) produced as described above by an ordinary process for reducing nitro groups.

Production process 5

Chemical formula 24

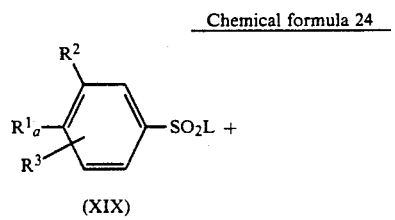

(XIX)

-continued
Chemical formula 24

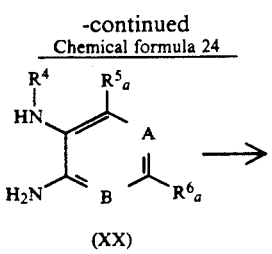

(XX)

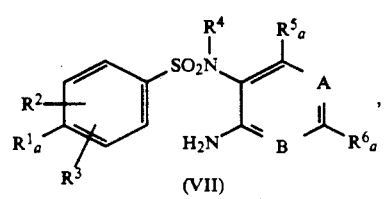

(VII)

wherein $R^1_a$, $R^2$, $R^3$, $R^4$, $R^5_a$, $R^6_a$, A, B and L are each as defined above.

The compounds represented by the general formula (VII) can be produced by reacting a compound of the general formula (XIX) with a compound of the general formula (XX). The reaction conditions vary depending on the compounds. Usually 2 to 4 equivalents of the compound (XX) is preferably used per equivalent of the sulfonyl halide (XIX). The reaction solvent is preferably tetrahydrofuran, dioxane, pyridine, dimethylformamide or the like. The reaction can be conducted also under hydrous conditions. The reaction usually proceeds at room temperature and, if desired it may be conducted under cooling or heating.

When the compounds of the present invention are used as medicines, they are given by oral or parenteral administration. The dosage is not limited, since it varies depending on the symptoms; age, sex, body weight and sensitivity of the patient; administration method; time and interval of administration; properties, formulation and kind of preparation; and the variety of the active ingredient.

The dose, which varies depending on the administration manner, is usually 10 to 6000 mg, preferably about 50 to 4000 mg and, more preferably, 100 to 3000 mg a day for adult. This dose of the compound is given in portions 1 to 3 times a day.

In the production of a solid preparation for oral administration, an excipient and, if necessary, binder, disintegrator, lubricant, colorant, corrigent, etc., are added to the active ingredient and they are shaped into tablets, coated tablets, granules, fine granules, powder or capsules.

Examples of the excipients include lactose, corn starch, white sugar, glucose, sorbitol, crystalline cellulose and silicon dioxide. Examples of the binders include polyvinyl alcohol, polyvinyl ether, ethylcellulose, methylcellulose, acacia, tragacanth, gelatin, shellac, hydroxypropylcellulose, hydroxypropylmethylcellulose, calcium citrate, dextrin and pectin. Examples of the lubricants include magnesium stearate, talc, polyethylene glycol, silica and hardened vegetable oils. The colorants are those admitted to be added to medicines. Examples of the corrigents include cocoa powder, methanol, aromatic powder, peppermint oil, borneol and cinnamon powder. These tablets and granules may be suitably coated with sugar, gelatin or the like, as a matter of course.

In the preparation of an injection, a pH modifier, buffering agent, suspension agent, solubilizer, stabilizer, isotonizer, preservative, etc., are added to the active ingredient to form an intravenous, subcutaneous or intramuscular injection by an ordinary process. If necessary, they are freeze-dried.

Examples of the suspension agents include methylcellulose, Polysorbate 80, hydroxyethylcellulose, acacia, tragacanth powder, sodium carboxymethylcellulose and polyoxyethylene sorbitan monolaurate.

Examples of the solubilizers include polyoxyethylene-hardened castor oil, Polysorbate 80, nicotinamide, polyoxyethylene sorbitan monolaurate, macrogol and ethyl esters of castor oil fatty acids.

Examples of the stabilizers include sodium sulfite, sodium metasulfite and ether. Examples of the preservatives include methyl p-hydroxybenzoate, ethyl p-hydroxybenzoate, sorbic acid, phenol, cresol and chlorocresol.

EFFECT OF THE INVENTION

The following pharmacological experiments will illustrate the effects of the compounds of the present invention.

Experimental Example 1

In vitro antineoplastic test on KB cells (human nasopharyngeal cells):

$1.25 \times 10^3$ (0.1 ml) of KB cells suspended in a RPMI 1640 medium (a product of Nissui Seiyaku Co., Ltd.) containing 20% of bovine fetus serum, penicillin (100 units/ml), streptomycin (100 μg/ml), mercaptoethanol ($5 \times 10^{-5}$M) and sodium pyruvate (1 mM) were placed in each hole of a 96-hole flat-bottom microplate and cultured in an incubator containing 5% of carbon dioxide at 37° C. for one day.

A compound of the present invention was dissolved in dimethyl sulfoxide to obtain a 20 mg/ml solution, which was diluted to a concentration of 100 μg/ml with 0.1% bovine fetus serum/RPMI 1640 culture liquid. This concentration was the maximum one, which was subjected to two-fold serial dilution with 0.1% bovine fetus serum RPMI 1640 culture liquid containing 0.5% of dimethyl sulfoxide. It was added to the KB cells in each hole of the above-described culture plate in an amount of 0.1 ml and cultured in an incubator containing 5% of carbon dioxide at 37° C. for three days.

After the completion of the culture, 0.05 ml of MTT [3-(4,5-dimethylthiazol-2-yl)-2,5-diphenyltetrazolium bromide] solution (3.3 mg/ml) was added to each hole and the culture was conducted for an additional 1 h. The supernatant liquid was removed from each hole by suction and a formazan thus formed was dissolved in 0.1 ml of dimethyl sulfoxide. The absorbance at 540 nm was determined with a microplate reader to use as an index of a viable count. A percentage inhibition was calculated according to the following formula and the concentration of the test compound for 50% inhibition ($IC_{50}$) was determined.

Numerical formula 1

$$\text{Percentage inhibition } (\%) = (C-T)/C \times 100$$

T: absorbance of the hole containing the test compound
C: absorbance of the hole containing no test compound Values of $IC_{50}$ of KB cells in vitro thus determined are given in Table 1.

TABLE 1

| Compound (Ex. No.) | IC$_{50}$ (μg/ml) |
| --- | --- |
| 1 | 1.5 |
| 2 | 1.7 |
| 3 | 0.27 |
| 4 | 1.9 |
| 5 | 0.73 |
| 6 | 0.42 |
| 7 | 1.0 |
| 8 | 0.89 |
| 9 | 0.34 |
| 10 | 0.21 |
| 11 | 0.33 |
| 13 | 2.6 |
| 16 | 1.5 |
| 17 | 0.94 |
| 18 | 0.73 |
| 21 | 1.1 |
| 27 | 1.4 |
| 34 | 0.11 |
| 35 | 0.45 |
| 36 | 0.72 |
| 37 | 1.3 |
| 40 | 2.1 |
| 42 | 0.59 |
| 43 | 0.26 |
| 47 | 2.6 |
| 52 | 0.54 |
| 54 | 0.54 |
| 57 | 0.17 |
| 58 | 1.2 |
| 59 | 0.18 |
| 61 | 0.83 |
| 62 | 0.53 |
| 63 | 0.20 |
| 64 | 0.55 |
| 65 | 0.20 |
| 67 | 1.4 |
| 68 | 0.17 |
| 70 | 0.033 |
| 71 | 0.11 |
| 72 | 0.012 |
| 76 | 0.13 |
| 82 | 0.026 |
| 85 | 0.010 |
| 88 | 0.010 |
| 91 | 0.079 |
| 94 | 0.064 |
| 95 | 0.045 |
| 97 | 0.15 |
| 98 | 0.079 |
| 101 | 0.10 |
| 104 | 0.099 |
| 106 | 0.30 |

Experimental Example 2

In vivo antineoplastic test on colon 38 (cancer of the colon of mice):

About 75 mg of colon 38 was subcutaneously transplanted in the side of the body of each of 7-week old female BDF$_1$ mice. A compound of the present invention was suspended in 0.5% methylcellulose and oral administration of a predetermined amount of the suspension once a day was started on the next day and continued for 8 days. 0.5% methylcellulose was orally given to a control group. The control group consisted of 10 mice and the group to which the medicine was given consisted of 6 mice.

21 days after the transplantation, the tumors were taken out and weighed. The tumor growth inhibition ratio of the group to which the medicine was given to the control group was determined according to the following formula:

Numerical formula 2

Growth inhibition ratio (%) $(C-T)/C \times 100$

T: average weight of tumor in the group to which the test compound was given

C: average weight of tumor in the control group

The results of the experiments are given in Table 2.

TABLE 2

| Compound (Ex. No.) | Dose (mg/kg/day) | Growth inhibition ratio | Survival rate on the day of judgement (the 21st day) |
| --- | --- | --- | --- |
| 1 | 100 | 80 | 100 |
| 2 | 100 | 69 | 100 |
| 3 | 100 | 98 | 100 |
| 4 | 100 | 99 | 100 |
| 6 | 100 | 98 | 100 |
| 7 | 50 | 61 | 100 |
| 70 | 50 | 63 | 100 |

Experimental Example 3: Toxicity tests

A 0.5% suspension of a compound of Example 3, 4 or 6 in methylcellulose was given to a group of five 7-week old female BDF$_1$ mice once and the viability of them was observed for 7 days after the administration. No mouse died, even with 1651 mg/kg of the compound.

It is apparent from the above Experimental Examples that the compounds of the present invention exhibit a quite excellent antineoplastic effect. In addition, the compounds of the present invention have such a high safety that they are useful as a remedy for malignant tumors, i.e. as an antineoplastic agent.

EXAMPLES

The following Production Examples will illustrate the processes for producing the starting compounds of the compounds of the present invention and the following Examples will illustrate the typical compounds of the present invention, which by no means limit the invention.

Production Example 1

2-Anilino-3-nitropyridine:

Chemical formula 25

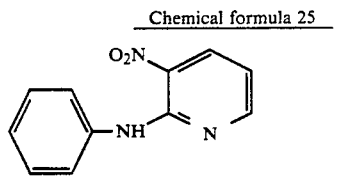

A mixture of 11.21 g (70 mmol) of 2-chloro-3-nitropyridine and 19.56 g (210 mmol) of aniline was heated under stirring at 100° C. for 1 h. The reaction liquid was cooled to room temperature and dissolved in ethyl acetate. The solution was washed with an aqueous citric acid solution and then with water. After drying over magnesium sulfate, the solvent was distilled off under reduced pressure and the residue was recrystallized from ethyl acetate/n-hexane to obtain 13.7 g of the title compound.

Melting point: 73° to 74° C.

FAB mass spectrometry m/z: 216 ([M+H]$^+$)

$^1$H-NMR (CDCl$_3$) δ (ppm): 6.84 (1H, dd, J=8.4, 4.4 Hz), 7.18–7.22 (1H, m), 7.37–7.43 (2H, m), 7.62–7.68 (2H, m), 8.49 (1H, dd, J=4.4, 2.0 Hz), 8.53 (1H, dd, J=8.4, 2.0 Hz), 10.12 (1H, br-s)

| Elementary analysis for $C_{11}H_9N_3O_2$: | | | |
|---|---|---|---|
| | C | H | N |
| Calculated: | 61.39 | 4.22 | 19.53 |
| Found: | 61.49 | 4.34 | 19.23 |

Production Example 2

3-Amino-2-anilinopyridine:

Chemical formula 26

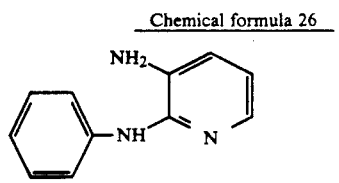

6.8 g (31.6 mmol) of the compound produced in Production Example 1 was dissolved in a mixture of 40 ml of tetrahydrofuran and 6 ml of methanol. Palladium/-carbon was added to the solution to conduct hydrogenation at room temperature under atmospheric pressure. The palladium/carbon was removed by filtration, the solvent was distilled off under reduced pressure and the residue was recrystallized from ethyl acetate/n-hexane to obtain 5.5 g of the title compound.

Melting point: 143° to 144° C.

FAB mass spectrometry m/z: 186 ([M+H]+)

$^1$H-NMR (DMSO-d$_6$) δ (ppm): 4.95–5.10 (2H, br), 6.61 (1H, dd, J=7.2, 4.8 Hz), 6.80–6.86 (1H, m), 6.90 (1H, dd, J=7.2, 1.6 Hz), 7.18–7.24 (2H, m), 7.49 (1H, dd, J=4.8, 1.6 Hz), 7.60–7.65 (2H, m), 7.69 (1H, s)

| Elementary analysis for $C_{11}H_{11}N_3$: | | | |
|---|---|---|---|
| | C | H | N |
| Calculated: | 71.33 | 5.99 | 22.69 |
| Found: | 71.49 | 6.04 | 22.59 |

Production Example 3

4-[(3-Nitro-2-pyridyl)amino]phenol

Chemical formula: 27

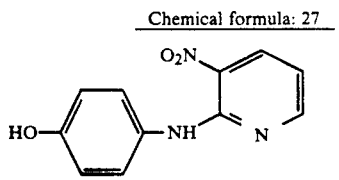

8.17 g (50 mmol) of 2-chloro-3-nitropyridine and 16.70 g (150 mmol) of p-aminophenol were added to 50 ml of dimethylformamide and the mixture was stirred at 100° C. for 40 min. The solvent was distilled off under reduced pressure, the same treatment as that of Production Example 1 was repeated and the product was recrystallized from ethanol to obtain 9.4 g of the title compound.

Melting point: 143° to 144° C.

FAB mass spectrometry m/z: 231 (M+)

$^1$H-NMR (CDCl$_3$) δ (ppm): 5.23 (1H, s), 6.79 (1H, dd, J=4.8, 8.4 Hz), 6.84 (2H, d, J=8.8 Hz), 7.41 (2H, d, J=8.8 Hz), 8.44 (1H, dd, J=1.6, 4.8 Hz), 8.52 (1H, dd, J=1.6, 8.4 Hz), 9.94 (1H, br-s)

| Elementary analysis for $C_{11}H_9N_3O_3$: | | | |
|---|---|---|---|
| | C | H | N |
| Calculated: | 57.14 | 3.92 | 18.18 |
| Found: | 57.15 | 3.97 | 18.14 |

Production Example 4

4-[(3-Amino-2-pyridyl)amino]phenol

Chemical formula: 28

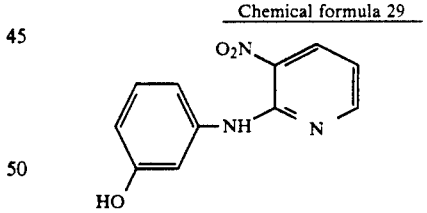

9.25 g (40 mmol) of the compound produced in Production Example 3 was catalytically reduced and treated in the same manner as that of Production Example 2 and the product was recrystallized from methanol to obtain 7.8 g of the title compound.

Melting point: 205° to 207° C.

FAB mass spectrometry m/z: 202 ([M+H]+)

$^1$H-NMR (DMSO-d$_6$) δ (ppm): 4.94 (2H, br-s), 6.50 (1H, dd, J=4.8, 7.6 Hz), 6.66 (2H, d, J=8.8 Hz), 6.82 (1H, dd, J=1.6, 7.6 Hz), 7.38 (1H, s), 7.39 (2H, d, J=8.8 Hz), 7.40 (1H, dd, J=1.6, 4.8 Hz), 8.85 (1H, s)

| Elementary analysis for $C_{11}H_{11}N_3O$: | | | |
|---|---|---|---|
| | C | H | N |
| Calculated: | 65.66 | 5.51 | 20.88 |
| Found: | 65.85 | 5.51 | 20.84 |

Production Example 5

3-[(3-Nitro-2-pyridyl)amino)]phenol:

Chemical formula 29

Melting point: 148° to 149° C. (recrystallized from ethanol)

FAB mass spectrometry m/z: 232 ([M+H]+)

$^1$H-NMR (CDCl$_3$) δ (ppm): 5.31 (1H, br-s), 6.65 (1H, dd, J=8.0, 2.4 Hz), 6.85 (1H, dd, J=8.4, 4.8 Hz), 7.08 (1H, dd, J=8.0, 2.4 Hz), 7.24 (1H, t, J=8.0 Hz), 7.37 (1H, t, J=2.4 Hz), 8.49 (1H, dd, J=4.8, 1.6 Hz), 8.54 (1H, dd, J=8.4, 1.6 Hz), 10.11 (1H, br-s)

| Elementary analysis for $C_{11}H_9N_3O_3$: | | | |
|---|---|---|---|
| | C | H | N |
| Calculated: | 57.14 | 3.92 | 18.17 |
| Found: | 57.33 | 4.03 | 18.18 |

Production Example 6

3-[(3-Amino-2-pyridyl)amino)]phenol:

Chemical formula 30

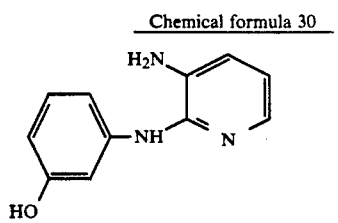

Melting point: gradual decomposition observed at 198° C. (recrystallized from ethanol)

FAB mass spectrometry m/z: 202 ([M+H]+)

$^1$H-NMR (DMSO-d$_6$) δ (ppm): 5.04 (2H, s), 6.24–6.28 (1H, m), 6.60 (1H, dd, J=7.6, 4.8 Hz), 6.89 (1H, dd, J=7.6, 1.6 Hz), 6.97–6.99 (2H, m), 7.23 (1H, br-s), 7.50 (1H, dd, J=4.8, 1.6 Hz), 7.57 (1H, s), 9.10 (1H, s)

Elementary analysis for C$_{11}$H$_{11}$N$_3$O:

|  | C | H | N |
|---|---|---|---|
| Calculated: | 65.66 | 5.51 | 20.88 |
| Found: | 65.92 | 5.58 | 20.86 |

Production Example 7

2-[(4-Methoxymethyloxyphenyl)amino]-3-nitropyridine

Chemical formula 31

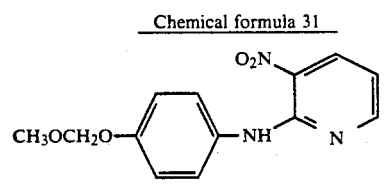

8.4 g (54.8 mmol) of 4-methoxymethyloxyaniline and 7.5 g (49 mmol) of 2-chloro-3-nitropyridine were dissolved in 35 ml of dimethylformamide. 7.6 g (55 mmol) of anhydrous potassium carbonate was added to the solution. The resulting solution was heated under stirring at 100° C. for 4 h. The reaction liquid was cooled to room temperature and an insoluble matter thus formed was removed by filtration. The solvent was distilled off under reduced pressure and the residue was dissolved in ethyl acetate. The solution was washed with an aqueous citric acid solution and then with water. After drying over magnesium sulfate, the solvent was distilled off under reduced pressure and the residue was recrystallized from ethanol to obtain 9.68 g of the title compound.

Melting point: 80° to 81° C.

FAB mass spectrometry m/z: 275 (M+)

$^1$H-NMR (CDCl$_3$) δ (ppm): 3.50 (3H, s), 5.19 (2H, s), 6.79 (1H, dd, J=4.4, 8.4 Hz), 7.08 (2H, d, J=8.8 Hz), 7.50 (2H, d, J=8.8 Hz), 8.45 (1H, dd, J=1.6, 4.4 Hz), 8.51 (1H, dd, J=1.6, 8.4 Hz), 9.99 (1H, br-s)

Elementary analysis for C$_{13}$H$_{13}$N$_3$O$_4$:

|  | C | H | N |
|---|---|---|---|
| Calculated: | 56.73 | 4.76 | 15.27 |
| Found: | 57.06 | 4.83 | 15.02 |

Production Example 8

2-[N-Benzyloxycarbonyl-N-(4-methoxymethyloxyphenyl)amino]-3-nitropyridine:

Chemical formula 32

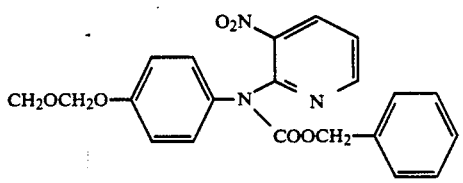

4.0 g (14.5 mmol) of the compound produced in Production Example 7 was dissolved in 70 ml of dimethylformamide. 720 mg (18 mmol) of sodium hydride (60%) was added to the solution. 3.2 ml (22.4 mmol) of benzyl chloroformate was added dropwise thereto under stirring at room temperature. After stirring at room temperature overnight, the solvent was distilled off under reduced pressure. Ethyl acetate and water were added to the residue and the ethyl acetate layer was separated. After washing the separated layer with water followed by drying (over magnesium sulfate), concentration and purification by silica gel column chromatography, 4.5 g of an oily title compound was obtained.

$^1$H-NMR (CDCl$_3$) δ (ppm): 3.47 (3H, s), 5.17 (4H, s+s), 7.06 (2H, d, J=8.8 Hz), 7.22–7.26 (2H, m), 7.29–7.33 (4H, m), 7.37 (2H, d, J=8.8 Hz), 8.29 (1H, d, J=8.0 Hz), 8.56 (1H, d, J=4.4 Hz)

Production Example 9

4-[N-Benzyloxycarbonyl-N-(3-nitro-2-pyridyl)amino]phenol:

Chemical formula 33

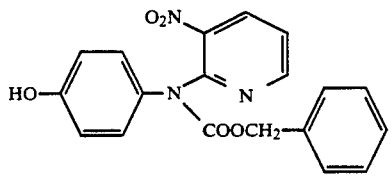

500 mg (1.22 mmol) of the compound produced in Production Example 8 was dissolved in a mixture of 6 ml of tetrahydrofuran and 1 ml of water. 2 ml of concentrated hydrochloric acid was added to the solution. After the mixture was stirred at room temperature overnight, the solvent was distilled off under reduced pressure. Ethyl acetate and a saturated aqueous sodium hydrogencarbonate solution were added to the residue and the ethyl acetate layer thus formed was separated. After washing the separated layer with water followed by drying (over magnesium sulfate) and concentration, 445 mg of the title compound was obtained.

$^1$H-NMR (DMSO-d$_6$) δ (ppm): 5.11 (2H, s), 6.77 (2H, d, J=8.8 Hz), 7.18–7.24 (4H, m), 7.31–7.34 (3H, m), 7.58 (1H, dd, J=4.8, 8.0 Hz), 8.51 (1H, dd, J=1.6, 8.0 Hz), 8.66 (1H, dd, J=1.6, 4.8 Hz), 9.64 (1H, s)

Production Example 10

4-[(3-Amino-2-pyridyl)amino]phenyl tert-butoxycarbonylaminoacetate:

Chemical formula 34

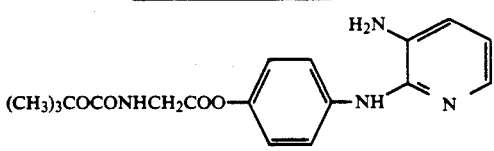

440 mg (1.2 mmol) of the compound produced in Production Example 9, 250 mg (1.43 mmol) of N-(tert-butoxycarbonyl)glycine and 25 mg (0.2 mmol) of 4-dimethylaminopyridine were dissolved in 10 ml of pyridine. 290 mg (1.41 mmol) of 1,3-dicyclohexylcarbodiimide was added to the solution. After stirring at room temperature overnight, the solvent was distilled off under reduced pressure. Ethyl acetate was added to the residue, the insoluble matter was removed by filtration and the solvent was distilled off under reduced pressure. The residue was purified according to silica gel column chromatography and the resulting compound was catalytically reduced in the presence of a palladium/carbon catalyst by an ordinary process. After the removal of the catalyst by filtration followed by concentration, the residue was purified by silica gel column chromatography to obtain 236 mg of the title compound.

$^1$H-NMR (DMSO-d$_6$) δ (ppm): 1.41 (9H, s), 3.93 (2H, d, J=6.0 Hz), 5.05 (2H, br-s), 6.62 (1H, dd, J=4.8, 7.2 Hz), 6.90 (1H, dd, J=1.6, 7.2 Hz), 6.96 (2H, d, J=9.2 Hz), 7.37 (1H, br-t, J=6.4 Hz), 7.49 (1H, dd, J=1.6, 4.8 Hz), 7.64 (2H, d, J=9.2 Hz), 7.79 (1H, s)

Production Example 11

4-[[3-(4-Methoxybenzenesulfonamido)-2-pyridyl]amino]phenyl-2,3,4,6-tetra-O-acetyl-β-D-glucopyranoside:

Chemical formula 35

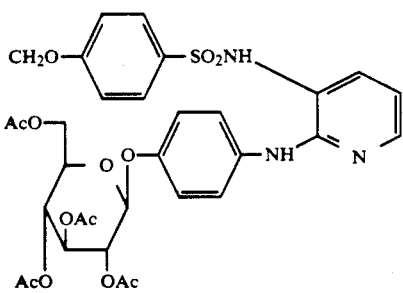

3.753 g (10.10 mmol) of the compound produced in Example 6 and 3.959 g (10.14 mmol) of β-D-glucose pentacetate were suspended in 200 ml of 1,2-dichloroethane. 30 ml of a 1.0M solution of tin tetrachloride in dichloromethane was added dropwise to the suspension under stirring and under cooling with ice in a nitrogen atmosphere. After stirring under cooling with ice for 2 h and then at room temperature for 4 days, the reaction mixture was added to ice/water containing 16 g of sodium hydrogencarbonate. The organic solvent was distilled off under reduced pressure. Ethyl acetate was added to the residue and the insoluble matter thus formed was removed by filtration. The ethyl acetate layer was separated, washed with water, dried, concentrated and purified by silica gel column chromatography to obtain 2.47 g of the title compound.

$^1$H-NMR (CDCl$_3$) δ (ppm): 2.04 (3H, s), 2.05 (3H, s), 2.08 (3H, s), 2.10 (3H, s), 3.80–3.86 (1H, m), 3.84 (3H, s), 4.17 (1H, dd, J=12.4, 2.4 Hz), 4.30 (1H, dd, J=12.4, 5.6 Hz), 4.99 (1H, d, J=7.6 Hz), 5.16 (1H, t, J=9.6 Hz), 5.23–5.32 (2H, m), 6.37 (1H, br-s), 6.54 (1H, dd, J=4.8, 7.6 Hz), 6.84 (1H, dd, J=1.6, 7.6 Hz), 6.92 (2H, d, J=8.8 Hz), 6.94 (2H, d, J=8.8 Hz), 7.32 (1H, br-s), 7.38 (2H, d, J=8.8 Hz), 7.69 (2H, d, J=8.8 Hz), 8.07 (1H, dd, J=1.6, 4.8 Hz)

Production Example 12

N-(2-Aminophenyl)-4-methoxybenzenesulfonamide:

Chemical formula 36

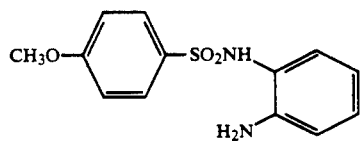

33.1 g (0.3 mol) of 1,2-phenylenediamine was dissolved in 200 ml of dioxane. A solution of 20.87 g (0.1 mol) of 4-methoxybenzenesulfonyl chloride in 110 ml of dioxane was added thereto under stirring. The resulting mixture was stirred at room temperature overnight. 12.1 g (0.12 mol) of triethylamine was added thereto. After concentration followed by addition of an aqueous citric acid solution and ethyl acetate, the organic layer was separated, concentrated and purified by silica gel column chromatography to obtain 27.1 g of the title compound.

Melting point: 141° to 142° C. (recrystallized from ethanol)

FAB mass spectrometry m/z: 279 ([M+H]$^+$)

$^1$H-NMR (DMSO-d$_6$) δ (ppm): 3.81 (3H, s), 4.91 (2H, br-s), 6.37 (1H, td, J=1.6, 7.2, 8.0 Hz), 6.60 (1H, dd, J=1.6, 8.0 Hz), 6.66 (1H, dd, J=1.6, 8.0 Hz), 6.86 (1H, td, J=1.6, 7.2, 8.0 Hz), 7.03 (2H, d, J=8.8 Hz), 7.61 (2H, d, J=8.8 Hz), 9.07 (1H, br-s)

| Elementary analysis for C$_{13}$H$_{14}$N$_2$O$_3$S: | | | |
|---|---|---|---|
| | C | H | N |
| Calculated: | 56.10 | 5.07 | 10.07 |
| Found: | 55.98 | 5.03 | 10.00 |

Production Example 13

N-(2-Aminophenyl)-4-nitrobenzenesulfonamide:

Chemical formula 37

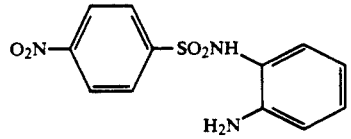

The title compound was produced in the same manner as that of Production Example 12.

Melting point: 190° to 191° C. (recrystallized from benzene)

FAB mass spectrometry m/z: 294 ([M+H]$^+$)

$^1$H-NMR (DMSO-d$_6$) δ(ppm): 4.90 (2H, br-s), 6.42 (1H, dt, J=1.6, 8.0 Hz), 6.61 (1H, dd, J=1.6, 8.0 Hz), 6.71 (1H, dd, J=1.6, 8.0 Hz), 6.91 (1H, dt, J=1.6, 8.0 Hz), 7.91 (2H, d, J=8.8 Hz), 8.36 (2H, d, J=8.8 Hz)

Elementary analysis for C$_{12}$H$_{11}$N$_3$O$_4$S:

|  | C | H | N |
|---|---|---|---|
| Calculated: | 49.14 | 3.78 | 14.33 |
| Found: | 49.38 | 3.82 | 14.13 |

Production Example 14

N-(2-Amino-3-methylphenyl)-4-methoxybenzenesulfonamide:

Chemical formula 38

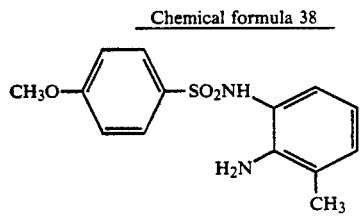

The title compound was produced in the same manner as that of Production Example 12.

Melting point: 177° to 178° C. (recrystallized from ethanol)

FAB mass spectrometry m/z: 293 ([M+H]$^+$)

$^1$H-NMR (DMSO-d$_6$) δ (ppm): 2.03 (3H, s), 3.81 (3H, s), 4.75 (2H, br-s), 6.30 (1H, t, J=7.6 Hz), 6.44 (1H, dd, J=1.2, 7.6 Hz), 6.79 (1H, dd, J=1.2, 7.6 Hz), 7.04 (2H, d, J=8.8 Hz), 7.61 (2H, d, J=8.8 Hz)

Elementary analysis for C$_{14}$H$_{16}$N$_2$O$_3$S:

|  | C | H | N |
|---|---|---|---|
| Calculated: | 57.52 | 5.52 | 9.58 |
| Found: | 57.76 | 5.51 | 9.57 |

Example 1

N-(2-Anilino-3-pyridyl)-p-toluenesulfonamide:

Chemical formula 39

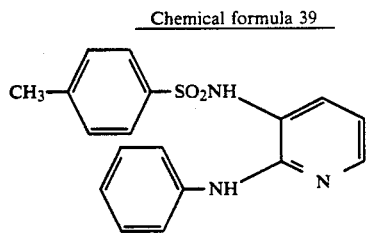

3.7 g (20 mmol) of the compound produced in Production Example 2 was dissolved in 30 ml of pyridine. 30 ml of a solution of 3.81 g (20 mmol) of p-toluenesulfonyl chloride in tetrahydrofuran was added in portions to the solution under stirring at room temperature. After stirring overnight, the solvent was distilled off under reduced pressure and the residue was dissolved in ethyl acetate. The solution was washed with water and dried over magnesium sulfate. The solvent was distilled off under reduced pressure and the residue was recrystallized from ethanol to obtain 5.2 g of the title compound.

Melting point: 164° to 165° C.

FAB mass spectrometry m/z: 340 ([M+H]$^+$)

$^1$H-NMR (DMSO-d$_6$) δ (ppm): 2.23 (3H, s), 6.73 (1H, dd, J=4.8, 7.6 Hz), 6.86-6.92 (1H, m), 7.18-7.24 (2H, m), 7.24 (2H, d, J=8.0 Hz), 7.27 (1H, dd, J=7.6, 1.6 Hz), 7.36-7.42 (2H, m), 7.54 (2H, d, J=8.0 Hz), 7.86 (1H, s), 7.99 (1H, dd, J=4.8, 1.6 Hz), 9.62 (1H, s)

Elementary analysis for C$_{18}$H$_{17}$N$_3$O$_2$S:

|  | C | H | N |
|---|---|---|---|
| Calculated: | 63.70 | 5.05 | 12.38 |
| Found: | 63.77 | 5.11 | 12.28 |

Example 2

N-(2-Anilino-3-pyridyl)-4-ethylbenzenesulfonamide:

Chemical formula 40

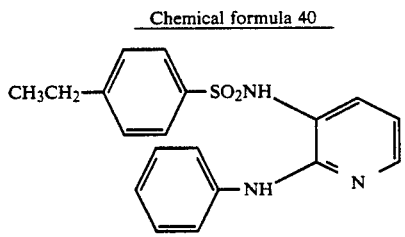

3.11 g (16.8 mmol) of the compound produced in Production Example 2 was reacted with 3.43 g (16.8 mmol) of p-ethylbenzenesulfonyl chloride and the product was treated in the same manner as that of Example 1 to obtain 5.0 g of the title compound.

Melting point: 138° to 139° C. (recrystallized from ethanol)

FAB mass spectrometry m/z: 354 ([M+H]$^+$)

$^1$H-NMR (DMSO-d$_6$) δ (ppm): 1.02 (3H, t), 2.50 (2H, q), 6.72 (1H, dd, J=5.2, 8.0 Hz), 6.83-6.89 (1H, m), 7.14-7.20 (2H, m), 7.24 (2H, d, J=8.4 Hz), 7.29 (1H, dd, J=8.0, 1.8 Hz), 7.32-7.37 (2H, m), 7.54 (2H, d, J=8.4 Hz), 7.80 (1H, s), 7.97 (1H, dd, J=5.2, 1.8 Hz), 9.60 (1H, s)

Elementary analysis for C$_{19}$H$_{19}$N$_3$O$_2$S:

|  | C | H | N |
|---|---|---|---|
| Calculated: | 64.57 | 5.42 | 11.89 |
| Found: | 64.89 | 5.33 | 12.00 |

Example 3

N-(2-Anilino-3-pyridyl)-4-methoxybenzenesulfonamide:

Chemical formula 41

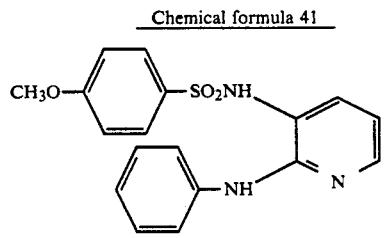

1.39 g (7.5 mmol) of the compound produced in Production Example 2 was reacted with 1.55 g (7.5 mmol) of p-methoxybenzenesulfonyl chloride and the product was treated in the same manner as that of Example 1 to obtain 2.6 g of the title compound.

Melting point: 172° to 173° C. (recrystallized from ethanol)

FAB mass spectrometry m/z: 356 ([M+H]+)

1H-NMR (DMSO-d6) δ (ppm): 3.68 (3H, s), 6.71 (1H, dd, J=7.6, 5.0 Hz), 6.84-6.90 (1H, m), 6.92 (2H, d, J=9.2 Hz), 7.15-7.22 (2H, m), 7.25 (1H, dd, J=7.6, 1.2 Hz), 7.36-7.42 (2H, m), 7.57 (2H, d, J=9.2 Hz), 7.86 (1H, s), 7.97 (1H, dd, J=5.0, 1.2 Hz), 9.51 (1H, s)

Elementary analysis for $C_{18}H_{17}N_3O_3S$:

|  | C | H | N |
|---|---|---|---|
| Calculated: | 60.83 | 4.82 | 11.82 |
| Found: | 61.02 | 4.69 | 11.86 |

Example 4

4-Methoxy-N-[2-[(4-methoxyphenyl)amino]-3-pyridyl]-benzenesulfonamide:

Chemical formula 42

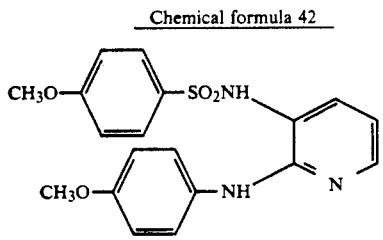

The title compound was obtained in the same manner as that of Example 1.

Melting point: 145° to 147° C. (recrystallized from ethanol)

FAB mass spectrometry m/z: 386 ([M+H]+)

1H-NMR (CDCl3) δ (ppm): 3.79 (3H, s), 3.85 (3H, s), 6.16 (1H, br-s), 6.52 (1H, dd, J=4.8, 7.6 Hz), 6.85 (3H, d, J=8.8 Hz), 6.93 (2H, d, J=8.8 Hz), 7.12 (1H, br-s), 7.32 (2H, d, J=8.8 Hz), 7.69 (2H, d, J=8.8 Hz), 8.07 (1H, dd, J=1.6, 4.8 Hz)

Elementary analysis for $C_{19}H_{19}N_3O_4S$:

|  | C | H | N |
|---|---|---|---|
| Calculated: | 59.21 | 4.97 | 10.90 |
| Found: | 59.26 | 5.05 | 10.75 |

Example 5

4-Methoxy-N-[2-[(4-methoxymethyloxyphenyl)amino]-3-pyridyl]benzenesulfonamide:

Chemical formula 43

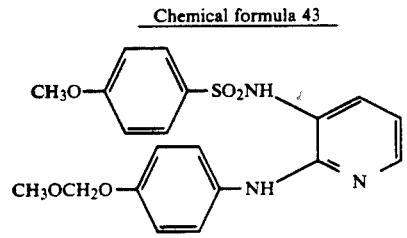

The title compound was produced in the same manner as that of Example 1.

Melting point: 118° to 119° C. (recrystallized from ethanol)

FAB mass spectrometry m/z: 416 ([M+H]+)

1H-NMR (CDCl3) δ (ppm): 3.48 (3H, s), 3.83 (3H, s), 5.13 (2H, s), 6.45 (1H, br-s), 6.52 (1H, dd, J=4.4, 7.6 Hz), 6.87 (1H, dd, J=1.6, 7.6 Hz), 6.92 (2H, d, J=8.8 Hz), 6.97 (2H, d, J=8.8 Hz), 7.16 (1H, br-s), 7.31 (2H, d, J=8.8 Hz), 7.69 (2H, d, J=8.8 Hz), 8.07 (1H, d)

Elementary analysis for $C_{20}H_{21}N_3O_5S$:

|  | C | H | N |
|---|---|---|---|
| Calculated: | 57.82 | 5.09 | 10.11 |
| Found: | 57.93 | 5.02 | 9.84 |

Example 6

N-[2-[(4-Hydroxyphenyl)amino]-3-pyridyl]-4-methoxybenzenesulfonamide:

Chemical formula 44

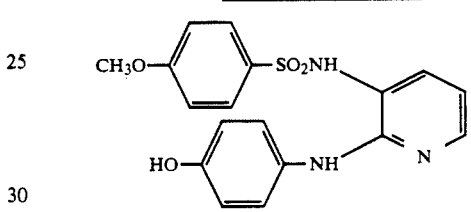

1.01 g (5 mmol) of the compound produced in Production Example 4 was reacted with 1.05 g (5 mmol) of p-methoxybenzenesulfonyl chloride and the product was treated in the same manner as that of Example 1 to obtain 1.43 g of the title compound.

Melting point: 178° to 179° C. (recrystallized from ethanol)

FAB mass spectrometry m/z: 372 ([M+H]+)

1H-NMR (DMSO-d6) δ (ppm): 3.75 (3H, s), 6.60 (1H, dd, J=4.8, 7.6 Hz), 6.63 (2H, d, J=8.8 Hz), 6.98 (2H, d, J=8.8 Hz), 7.14 (2H, d, J=8.8 Hz), 7.18 (1H, dd, J=1.6, 7.6 Hz), 7.58 (1H, br-s), 7.60 (2H, d, J=8.8 Hz), 7.88 (1H, dd, J=1.6, 4.8 Hz), 8.97 (1H, s), 9.44 (1H, s)

Elementary analysis for $C_{18}H_{17}N_3O_4S$:

|  | C | H | N |
|---|---|---|---|
| Calculated: | 58.21 | 4.61 | 11.31 |
| Found: | 58.40 | 4.67 | 11.38 |

2.0 g of the title compound was dissolved in 50 ml of tetrahydrofuran. 0.5 ml of concentrated hydrochloric acid was added to the solution and the resulting solution was concentrated to dryness. The residue was recrystallized from methanol to obtain 1.9 g of hydrochloride of the title compound.

Melting point: gradual decomposition observed at 225° C.

Elementary analysis for $C_{18}H_{17}N_3O_4S \cdot HCl$:

|  | C | H | N |
|---|---|---|---|
| Calculated: | 53.01 | 4.45 | 10.30 |
| Found: | 52.97 | 4.33 | 10.19 |

Example 7

4-Methoxy-N-[2-[(4-pyridyl)amino]-3-pyridyl]benzenesulfonamide:

Chemical formula 45

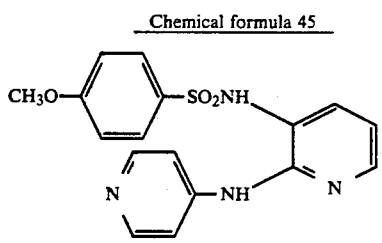

The title compound was produced in the same manner as that of Example 1.

Melting point: 172° to 173° C. (recrystallized from ethyl acetate)

FAB mass spectrometry m/z: 357 ([M+H]+)

$^1$H-NMR (DMSO-d$_6$) δ (ppm): 3.67 (3H, s), 6.86–6.91 (3H, m), 7.37 (1H, dd, J=1.6, 7.6 Hz), 7.48 (2H, d, J=5.6 Hz), 7.54 (2H, d, J=9.2 Hz), 8.04 (1H, dd, J=1.6, 4.8 Hz), 8.26 (2H, d, J=5.6 Hz), 8.59 (1H, br-s)

Elementary analysis for $C_{17}H_{16}N_4O_3S$:

|  | C | H | N |
|---|---|---|---|
| Calculated: | 57.29 | 4.53 | 15.72 |
| Found: | 57.37 | 4.56 | 15.66 |

Example 8

4-Methoxy-N-[2-[(4-methylphenyl)amino]-3-pyridyl]benzenesulfonamide:

Chemical formula 46

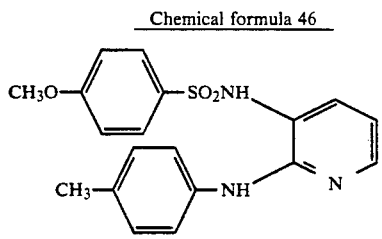

The title compound was produced in the same manner as that of Example 1.

Melting point: 188° to 189° C. (recrystallized from ethanol)

FAB mass spectrometry m/z: 370 ([M+H]+)

$^1$H-NMR (DMSO-d$_6$) δ (ppm): 2.21 (3H, s), 3.69 (3H, s), 6.66 (1H, dd, J=6.4, 2.4 Hz), 6.92 (2H, d, J=7.2 Hz), 6.99 (2H, d, J=7.6 Hz), 7.21 (1H, dd, J=6.4, 1.6 Hz), 7.27 (2H, d, J=7.2 Hz), 7.56 (2H, d, J=7.6 Hz), 7.75 (1H, s), 7.93 (1H, dd, J=2.4, 1.6 Hz), 9.48 (1H, br-s)

Elementary analysis for $C_{19}H_{19}N_3O_3S$:

|  | C | H | N |
|---|---|---|---|
| Calculated: | 61.77 | 5.18 | 11.38 |
| Found: | 61.82 | 5.21 | 11.30 |

Example 9

N-[2-[(2-Fluorophenyl)amino]-3-pyridyl]-4-methoxybenzenesulfonamide:

Chemical formula 47

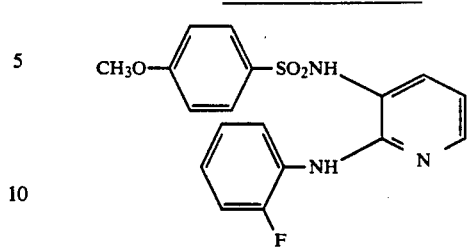

The title compound was produced in the same manner as that of Example 1.

Melting point: 148° to 150° C. (recrystallized from ethanol)

FAB mass spectrometry m/z: 374 ([M+H]+)

$^1$H-NMR (DMSO-d$_6$) δ (ppm): 3.72 (3H, s), 6.76 (1H, dd, J=7.6, 4.8 Hz), 6.90–6.98 (3H, m), 7.05 (1H, td, J=8.0, 0.8 Hz), 7.13–7.20 (2H, m), 7.57 (2H, d, J=8.8 Hz), 7.82 (1H, d, J=2.8 Hz), 7.95 (1H, t, J=8.0 Hz), 8.01 (1H, dd, J=4.8, 1.6 Hz), 9.76 (1H, s)

Elementary analysis for $C_{18}H_{16}FN_3O_3S$:

|  | C | H | N |
|---|---|---|---|
| Calculated: | 57.90 | 4.32 | 11.25 |
| Found: | 57.93 | 4.57 | 10.98 |

Example 10

N-[2-[(3-Fluorophenyl)amino]-3-pyridyl]-4-methoxybenzenesulfonamide:

Chemical formula 48

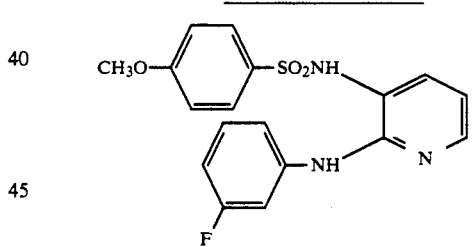

The title compound was produced in the same manner as that of Example 1.

Melting point: 180° to 181° C. (recrystallized from ethanol)

FAB mass spectrometry m/z: 374 ([M+H]+)

$^1$H-NMR (DMSO-d$_6$) δ (ppm): 3.69 (3H, s), 6.67 (1H, td, J=8.4, 2.0 Hz), 6.81 (1H, dd, J=7.6, 4.8 Hz), 6.92 (2H, d, J=8.8 Hz), 7.09 (1H, dd, J=8.4, 2.0 Hz), 7.22 (1H, dt, J=8.4, 6.8 Hz), 7.31 (1H, dd, J=7.6, 1.6 Hz), 7.49 (1H, dt, J=2.0, 12.4 Hz), 7.56 (2H, d, J=8.8 Hz), 8.05 (1H, dd, J=4.8, 1.6 Hz), 8.12 (1H, s), 9.52 (1H, br-s)

Elementary analysis for $C_{18}H_{16}FN_3O_3S$:

|  | C | H | N |
|---|---|---|---|
| Calculated: | 57.90 | 4.32 | 11.25 |
| Found: | 57.89 | 4.42 | 11.16 |

Example 11

N-[2-[(4-Fluorophenyl)amino]-3-pyridyl]-4-methoxybenzenesulfonamide:

Chemical formula 49

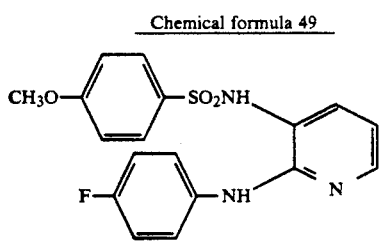

The title compound was produced in the same manner as that of Example 1.

Melting point: 196° to 197° C. (recrystallized from ethanol)

FAB mass spectrometry m/z: 374 ([M+H]+)

$^1$H-NMR (DMSO-d$_6$) δ (ppm): 3.71 (3H, s), 6.72 (1H, dd, J=4.8, 7.6 Hz), 6.95 (2H, d, J=8.8 Hz), 7.04 (2H, t, J=8.8 Hz), 7.25 (1H, dd, J=1.6, 7.6 Hz), 7.42 (2H, m), 7.58 (2H, d, J=8.8 Hz), 7.95 (1H, br-s), 7.98 (1H, dd, J=1.6, 4.8 Hz), 9.48 (1H, br-s)

Elementary analysis for C$_{18}$H$_{16}$FN$_3$O$_3$S:

|  | C | H | N |
|---|---|---|---|
| Calculated: | 57.90 | 4.32 | 11.25 |
| Found: | 57.83 | 4.32 | 11.21 |

Example 12

N-(2-Anilino-3-pyridyl)benzenesulfonamide:

Chemical formula 50

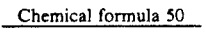

The title compound was produced in the same manner as that of Example 1.

Melting point: 148° to 150° C. (recrystallized from methanol)

FAB mass spectrometry m/z: 326 ([M+H]+)

$^1$H-NMR (DMSO-d$_6$) δ (ppm): 6.73 (1H, dd, J=7.6, 4.8 Hz), 6.87-6.93 (1H, m), 7.18-7.24 (2H, m), 7.25 (1H, dd, J=7.6, 1.6 Hz), 7.41-7.47 (2H, m), 7.47-7.51 (2H, m), 7.51-7.57 (1H, m) 7.67-7.72 (2H, m), 7.90 (1H, s), 7.99 (1H, dd, J=4.8, 1.6 Hz), 9.73 (1H, s)

Elementary analysis for C$_{17}$H$_{15}$N$_3$O$_2$S:

|  | C | H | N |
|---|---|---|---|
| Calculated: | 62.75 | 4.65 | 12.91 |
| Found: | 63.03 | 4.74 | 12.67 |

Example 13

4-Methoxy-N-[2-[(3-methoxyphenyl)amino]-3-pyridyl]benzenesulfonamide:

Chemical formula 51

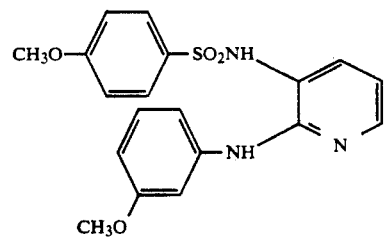

The title compound was produced in the same manner as that of Example 1.

Melting point: 161° to 162° C. (recrystallized from ethanol)

FAB mass spectrometry m/z: 386 ([M+H]+)

$^1$H-NMR (DMSO-d$_6$) δ (ppm): 3.67, 3.70 (3H×2), 6.47 (1H, dd, J=8.0, 2.0 Hz), 6.73 (1H, dd, J=8.0, 4.8 Hz), 6.93 (2H, d, J=8.8 Hz), 6.97 (1H, dd, J=8.0, 2.0 Hz), 7.10 (1H, t, J=8.0 Hz), 7.13 (1H, t, J=2.0 Hz), 7.29 (1H, dd, J=8.0, 1.6 Hz), 7.59 (2H, d, J=8.8 Hz), 7.89 (1H, s), 8.01 (1H, dd, J=4.8, 1.6 Hz), 9.55 (1H, s)

Elementary analysis for C$_{19}$H$_{19}$N$_3$O$_4$S:

|  | C | H | N |
|---|---|---|---|
| Calculated: | 59.21 | 4.97 | 10.90 |
| Found: | 59.14 | 4.96 | 10.74 |

Example 14

4-Hydroxy-N-[2-[(4-hydroxyphenyl)amino]-3-pyridyl]benzenesulfonamide:

Chemical formula 52

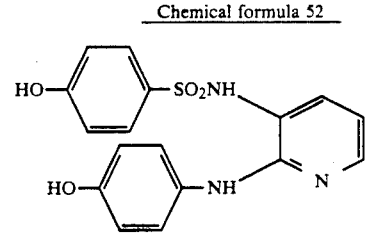

The compound produced in Example 4 was dissolved in DMF and five equivalents of sodium methanethiolate was added to the solution. The resulting solution was heated at 100° C. and treated to obtain the title compound.

Melting point: 252° to 257° C. (decomp.) (recrystallized from ethanol/water)

FAB mass spectrometry m/z: 358 ([M+H]+)

$^1$H-NMR (DMSO-d$_6$) δ (ppm): 6.60 (1H, dd, J=7.6, 4.8 Hz), 6.65 (2H, d, J=8.8 Hz), 6.81 (2H, d, J=8.8 Hz), 7.14 (1H, dd, J=7.6, 1.6 Hz), 7.19 (2H, d, J=8.8 Hz), 7.52 (2H, d, J=8.8 Hz), 7.61 (1H, s), 7.87 (1H, dd, J=4.8, 1.6 Hz), 9.01 (1H, s), 9.39 (1H, s), 10.42 (1H, s)

Example 15

N-[2-[(3,4-Dimethoxyphenyl)amino]-3-pyridyl]-4-methoxybenzenesulfonamide:

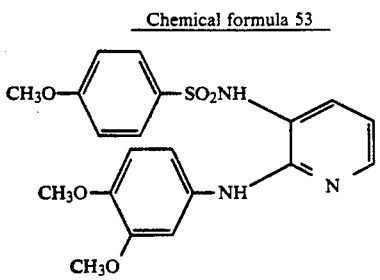

The title compound was produced in the same manner as that of Example 1.

Melting point: 126° to 127° C. (recrystallized from ethanol)

FAB mass spectrometry m/z: 415 (M+)

$^1$H-NMR (DMSO-$d_6$) δ (ppm): 3.72, 3.73 (3H×3), 6.66 (1H, dd, J=8.0, 3.6 Hz), 6.81 (1H, d, J=8.8 Hz), 6.96–6.98 (3H, m), 7.02 (1H, s), 7.21 (1H, dd, J=8.0, 1.2 Hz), 7.60 (2H, d, J=8.0 Hz), 7.73 (1H, s), 7.95 (1H, dd, J=3.6, 1.2 Hz), 9.45 (1H, br-s)

Elementary analysis for $C_{20}H_{21}N_3O_5S$:

|  | C | H | N |
| --- | --- | --- | --- |
| Calculated: | 57.82 | 5.10 | 10.12 |
| Found: | 57.73 | 5.10 | 10.07 |

Example 16

4-Methoxy-N-[2-[(2-methoxyphenyl)amino]-3-pyridyl]benzenesulfonamide:

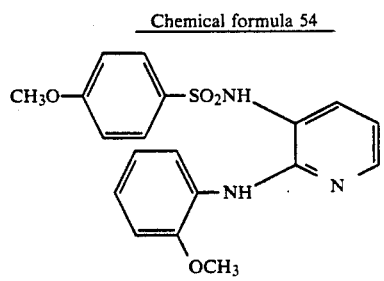

The title compound was produced in the same manner as that of Example 1.

Melting point: 159° to 160° C. (recrystallized from ethanol)

FAB mass spectrometry m/z: 386 ([M+H]+)

$^1$H-NMR (DMSO-$d_6$) δ (ppm): 3.78 (3H, s), 3.89 (3H, s), 6.69 (1H, dd, J=7.6, 4.8 Hz), 6.87–6.90 (2H, m), 6.96–7.01 (2H, m), 7.05 (2H, d, J=8.8 Hz), 7.66 (2H, d, J=8.8 Hz), 8.08 (1H, dd, J=4.8, 1.6 Hz), 8.10 (1H, s), 8.40 (1H, dd, J=6.4, 2.8 Hz), 9.78 (1H, s)

Elementary analysis for $C_{19}H_{19}N_3O_4S$:

|  | C | H | N |
| --- | --- | --- | --- |
| Calculated: | 59.21 | 4.97 | 10.90 |
| Found: | 59.16 | 5.01 | 10.96 |

Example 17

4-Methoxy-N-[2-[(3-methyphenyl)amino]-3-pyridyl]benzenesulfonamide:

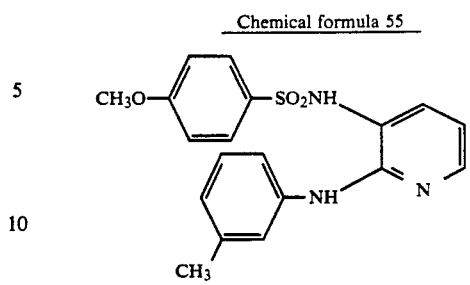

The title compound was produced in the same manner as that of Example 1.

Melting point: 147° to 148° C. (recrystallized from ethanol)

FAB mass spectrometry m/z: 370 ([M+H]+)

$^1$H-NMR (DMSO-$d_6$) δ (ppm): 2.26 (3H, s), 3.71 (3H, s), 6.71–6.73 (2H, m), 6.95 (2H, d, J=7.6 Hz), 7.09 (1H, t, J=7.6 Hz), 7.16 (1H, s), 7.25–7.27 (2H, m), 7.59 (2H, d, J=7.6 Hz), 7.90 (1H, s), 8.00 (1H, dd, J=2.8, 1.6 Hz), 9.53 (1H, br-s)

Elementary analysis for $C_{19}H_{19}N_3O_3S$:

|  | C | H | N |
| --- | --- | --- | --- |
| Calculated: | 61.77 | 5.18 | 11.38 |
| Found: | 61.79 | 5.18 | 11.46 |

Example 18

4-Methoxy-N-[2-[(2-methylphenyl)amino]-3-pyridyl]benzenesulfonamide:

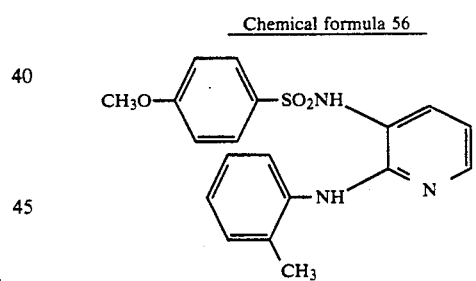

The title compound was produced in the same manner as that of Example 1.

Melting point: 147° to 148° C. (recrystallized from ethanol)

FAB mass spectrometry m/z: 370 ([M+H]+)

$^1$H-NMR (DMSO-$d_6$) δ (ppm): 2.06 (3H, s), 3.77 (3H, s), 6.65 (1H, dd, J=7.6, 4.8 Hz), 6.92 (1H, t, J=7.6 Hz), 7.03 (2H, d, J=8.8 Hz), 7.09 (1H, t, J=7.6 Hz), 7.11–7.15 (2H, m), 7.53 (1H, s), 7.55 (1H, d, J=7.6 Hz), 7.63 (2H, d, J=8.8 Hz), 7.91 (1H, dd, J=4.8, 1.6 Hz), 9.67 (1H, s)

Elementary analysis for $C_{19}H_{19}N_3O_3S$:

|  | C | H | N |
| --- | --- | --- | --- |
| Calculated: | 61.77 | 5.18 | 11.38 |
| Found: | 61.80 | 5.17 | 11.40 |

Example 19

N-(2-Anilino-3-pyridyl)-4-hydroxybenzenesulfonamide:

Chemical formula 57

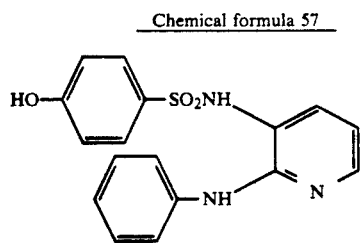

The title compound was produced by treating the compound of Example 3 in the same manner as that of Example 14.

Melting point: 226° to 228° C. (recrystallized from methanol)

FAB mass spectrometry m/z: 342 ([M+H]+)

$^1$H-NMR (DMSO-d$_6$) δ (ppm): 6.71 (1H, dd, J=7.6, 4.8 Hz), 6.79 (2H, d, J=8.8 Hz), 6.88–6.94 (1H, m), 7.21 (1H, dd, J=7.6, 1.6 Hz), 7.21–7.27 (2H, m), 7.46–7.51 (2H, m), 7.52 (2H, d, J=8.8 Hz), 7.92 (1H, s), 7.97 (1H, dd, J=4.8, 1.6 Hz), 9.50 (1H, s), 10.40 (1H, s)

Example 20

N-(2-Anilino-3-pyridyl)-4-nitrobenzenesulfonamide:

Chemical formula 58

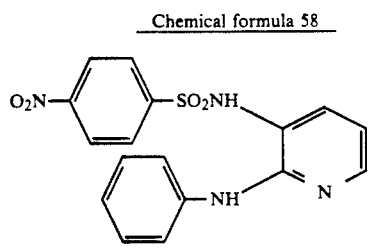

The title compound was produced in the same manner as that of Example 1.

Melting point: 191° to 192° C. (recrystallized from ethanol)

FAB mass spectrometry m/z: 371 ([M+H]+)

$^1$H-NMR (DMSO-d$_6$) δ (ppm): 6.80–6.83 (2H, m), 7.12 (2H, t, J=8.4 Hz), 7.25 (2H, d, J=8.4 Hz), 7.40 (1H, dd, J=1.6, 7.6 Hz), 7.83 (3H, d, J=8.8 Hz), 8.07 (1H, br-s), 8.19 (2H, d, J=8.8 Hz), 9.91 (1H, br-s)

Elementary analysis for C$_{17}$H$_{14}$N$_4$O$_4$S:

| | C | H | N |
|---|---|---|---|
| Calculated: | 55.13 | 3.81 | 15.13 |
| Found: | 55.17 | 3.97 | 14.77 |

Example 21

4-Amino-N-(2-anilino-3-pyridyl)benzenesulfonamide:

Chemical formula 59

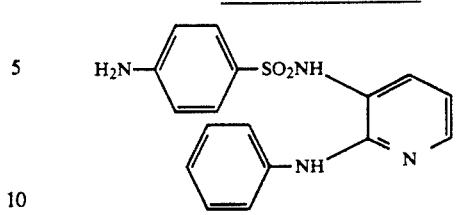

The title compound was produced by catalytically reducing the compound of Example 20 in the presence of a palladium/carbon catalyst by an ordinary process.

Melting point: 228° to 230° C. (recrystallized from ethanol)

FAB mass spectrometry m/z: 341 ([M+H]+)

$^1$H-NMR (DMSO-d$_6$) δ (ppm): 5.99 (2H, br-s), 6.50 (2H, d, J=8.8 Hz), 6.70 (1H, dd, J=4.4, 7.6 Hz), 6.91 (1H, td, J=0.8, 7.2 Hz), 7.18 (1H, dd, J=1.6, 7.6 Hz), 7.24 (2H, t, J=7.6 Hz), 7.33 (2H, d, J=8.8 Hz), 7.53 (2H, dt, J=1.2, 7.6 Hz), 7.95 (2H, br-s), 9.31 (1H, s)

Elementary analysis for C$_{17}$H$_{16}$N$_4$O$_2$S:

| | C | H | N |
|---|---|---|---|
| Calculated: | 59.98 | 4.74 | 16.46 |
| Found: | 60.08 | 4.67 | 16.23 |

Example 22

N-(2-Anilino-3-pyridyl)-3,4-dimethoxybenzenesulfonamide:

Chemical formula 60

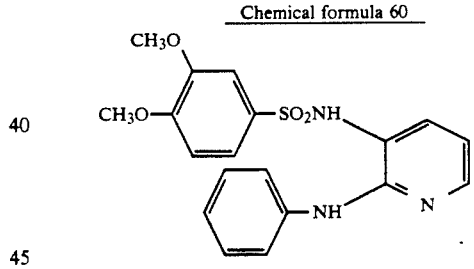

The title compound was produced in the same manner as that of Example 1.

Melting point: 171° to 172° C. (recrystallized from ethanol)

FAB mass spectrometry m/z: 386 ([M+H]+)

$^1$H-NMR (DMSO-d$_6$) δ (ppm): 3.64 (3H, s), 3.69 (3H, s), 6.75 (1H, dd, J=4.8 7.6 Hz), 6.88 (1H, t, J=7.6 Hz), 6.93 (1H, d, J=8.8 Hz), 7.10 (1H, d, J=2.0 Hz), 7.17–7.22 (3H, m), 7.32 (1H, d, J=7.6 Hz), 7.39 (2H, d, J=8.0 Hz), 7.89 (1H, br-s), 8.00 (1H, d, J=4.8 Hz), 9.48 (1H, br-s)

Elementary analysis for C$_{19}$H$_{19}$N$_3$O$_4$S:

| | C | H | N |
|---|---|---|---|
| Calculated: | 59.21 | 4.97 | 10.90 |
| Found: | 59.22 | 4.91 | 10.63 |

Example 23

4-Hydroxy-N-[2-[(4-methoxyphenyl)amino]-3-pyridyl]benzenesulfonamide:

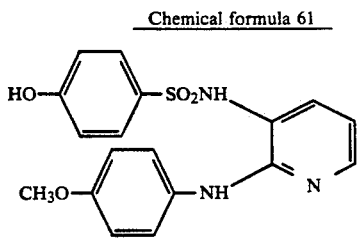

Chemical formula 61

The title compound was produced by the same treatment as that of Example 14.

Melting point: 214° to 216° C. (recrystallized from ethanol/water)

FAB mass spectrometry m/z: 372 ([M+H]+)

$^1$H-NMR (DMSO-d$_6$) δ (ppm): 3.71 (3H, s), 6.63 (1H, dd, J=7.6, 4.8 Hz), 6.80 (2H, d, J=8.8 Hz), 6.82 (2H, d, J=8.8 Hz), 7.16 (1H, dd, J=7.6, 1.6 Hz), 7.35 (2H, d, J=8.8 Hz), 7.51 (2H, d, J=8.8 Hz), 7.75 (1H, s), 7.90 (1H, dd, J=4.8, 1.6 Hz), 9.41 (1H, s), 10.42 (1H, s)

Elementary analysis for C$_{18}$H$_{17}$N$_3$O$_4$S:

|  | C | H | N |
|---|---|---|---|
| Calculated: | 58.21 | 4.61 | 11.31 |
| Found: | 58.21 | 4.74 | 11.01 |

Example 24

N-(2-Anilino-3-pyridyl)-4-chlorobenzenesulfonamide:

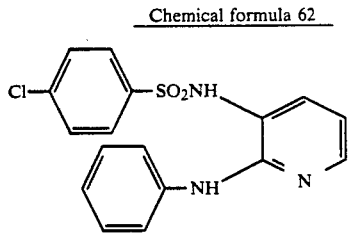

Chemical formula 62

The title compound was produced in the same manner as that of Example 1.

Melting point: 186° to 188° C. (recrystallized from ethanol)

FAB mass spectrometry m/z: 360 ([M+H]+)

$^1$H-NMR (DMSO-d$_6$) δ (ppm): 6.77 (1H, dd, J=7.6, 4.8 Hz), 6.90 (1H, dt, J=7.6, 0.8 Hz), 7.22 (2H, t, J=7.6 Hz), 7.30 (1H, dd, J=7.6, 1.2 Hz), 7.38 (2H, dd, J=7.6, 0.8 Hz), 7.51 (2H, d, J=8.4 Hz), 7.64 (2H, d, J=8.4 Hz), 7.89 (1H, s), 8.02 (1H, dd, J=4.8, 1.2 Hz), 9.76 (1H, br-s)

Elementary analysis for C$_{17}$H$_{14}$ClN$_3$O$_2$S:

|  | C | H | N |
|---|---|---|---|
| Calculated: | 56.74 | 3.92 | 11.68 |
| Found: | 56.79 | 4.03 | 11.67 |

Example 25

N-(2-Anilino-3-pyridyl)-3-chlorobenzenesulfonamide:

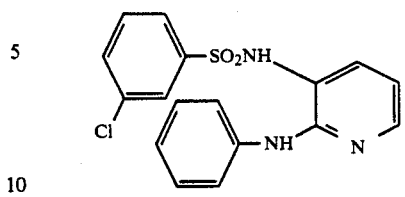

Chemical formula 63

The title compound was produced in the same manner as that of Example 1.

Melting point: 143° to 144° C. (recrystallized from ethanol)

FAB mass spectrometry m/z: 360 ([M+H]+)

$^1$H-NMR (DMSO-d$_6$) δ (ppm): 6.77 (1H, dd, J=7.6, 4.8 Hz), 6.91 (1H, dt, J=7.6, 1.2 Hz), 7.21 (2H, t, J=7.6 Hz), 7.32 (1H, dd, J=7.6, 1.6 Hz), 7.41 (2H, dd, J=7.6, 1.2 Hz), 7.46 (1H, t, J=8.0 Hz), 7.54-7.61 (2H, m), 7.68 (1H, br-s), 7.92 (1H, br-s), 8.04 (1H, dd, J=4.8, 1.6 Hz), 9.80 (1H, br-s)

Elementary anlysis for C$_{17}$H$_{14}$ClN$_3$O$_2$S:

|  | C | H | N |
|---|---|---|---|
| Calculated: | 56.74 | 3.92 | 11.68 |
| Found: | 56.73 | 4.09 | 11.68 |

Example 26

N-(2-Anilino-3-pyridyl)-3-methylbenzenesulfonamide:

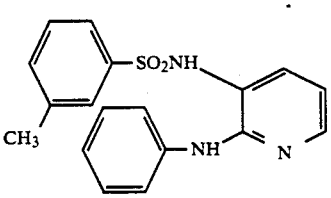

Chemical formula 64

The title compound was produced in the same manner as that of Example 1.

Melting point: 161° to 162° C. (recrystallized from ethanol)

FAB mass spectrometry m/z: 340 ([M+H]+)

$^1$H-NMR (DMSO-d$_6$) δ (ppm): 2.22 (3H, s), 6.74 (1H, dd, J=7.6, 4.8 Hz), 6.90 (1H, dt, J=7.2, 1.2 Hz), 7.21 (2H, t, J=7.2 Hz), 7.27-7.35 (3H, m), 7.42 (2H, dd, J=7.2, 1.2 Hz), 7.45 (1H, td, J=7.2, 2.0 Hz), 7.52 (1H, br-s), 7.92 (1H, s), 8.00 (1H, dd, J=4.8, 1.2 Hz), 9.68 (1H, br-s)

Elementary analysis for C$_{18}$H$_{17}$N$_3$O$_2$S:

|  | C | H | N |
|---|---|---|---|
| Calculated: | 63.70 | 5.05 | 12.38 |
| Found: | 63.81 | 5.16 | 12.43 |

Example 27

N-(2-Anilino-3-pyridyl)-4-ethoxybenzenesulfonamide:

Chemical formula 65

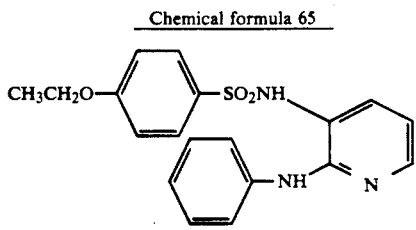

The title compound was produced in the same manner as that of Example 1.

Melting point: 161° to 162° C. (recrystallized from ethanol)

FAB mass spectrometry m/z: 370 ([M+H]+)

$^1$H-NMR (DMSO-d$_6$) δ (ppm): 1.26 (3H, t, J=7.0 Hz), 3.94 (2H, q, J=7.0 Hz), 6.74 (1H, dd, J=7.6, 4.8 Hz), 6.89 (1H, tt, J=7.2, 0.8 Hz), 6.92 (2H, d, J=8.8 Hz), 7.21 (2H, t, J=7.2 Hz), 7.27 (1H, dd, J=7.6, 1.6 Hz), 7.42 (2H, dd, J=7.2, 0.8 Hz), 7.57 (2H, d, J=8.8 Hz), 7.88 (1H, s), 7.99 (1H, dd, J=4.8, 1.6 Hz), 9.53 (1H, br-s)

Elementary analysis for C$_{19}$H$_{19}$N$_3$O$_3$S:

|  | C | H | N |
|---|---|---|---|
| Calculated: | 61.77 | 5.18 | 11.37 |
| Found: | 61.72 | 5.31 | 11.43 |

Example 28

4-Acetylamino-N-(2-anilino-3-pyridyl)benzenesulfonamide:

Chemical formula 66

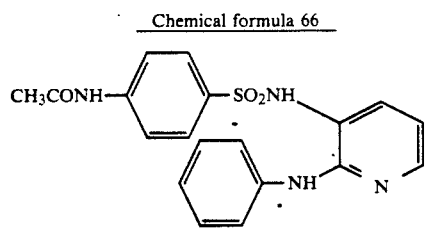

The title compound was produced in the same manner as that of Example 1.

Melting point: 234° to 236° C. (recrystallized from methanol)

FAB mass spectrometry m/z: 383 ([M+H]+)

$^1$H-NMR (DMSO-d$_6$) δ (ppm): 2.04 (3H, s), 6.72 (1H, dd, J=7.6, 4.8 Hz), 6.90 (1H, tt, J=8.0, 1.2 Hz), 7.19-7.24 (3H, m), 7.45 (2H, dd, J=8.0, 1.2 Hz), 7.60 (2H, d, J=9.2 Hz), 7.65 (2H, d, J=9.2 Hz), 7.91 (1H, s), 7.98 (1H, dd, J=4.8, 1.6 Hz), 9.60 (1H, br-s), 10.23 (1H, br-s)

Elementary analysis for C$_{19}$H$_{18}$N$_4$O$_3$S:

|  | C | H | N |
|---|---|---|---|
| Calculated: | 59.67 | 4.74 | 14.65 |
| Found: | 59.69 | 4.82 | 14.38 |

Example 29

N-(2-Anilino-3-pyridyl)-4-phenoxybenzenesulfonamide:

Chemical formula 67

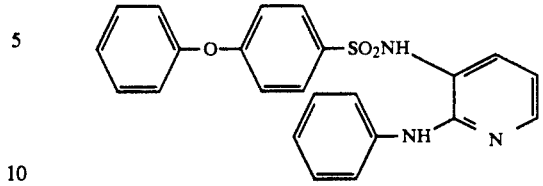

The title compound was produced in the same manner as that of Example 1.

Melting point: 164° to 166° C. (recrystallized from ethanol)

FAB mass spectrometry m/z: 418 ([M+H]+)

$^1$H-NMR (DMSO-d$_6$) δ (ppm): 6.78 (1H, dd, J=7.6, 4.8 Hz), 6.84 (2H, dd, J=7.6, 1.2 Hz), 6.91-6.96 (3H, m), 7.19-7.27 (3H, m), 7.36-7.40 (3H, m), 7.44 (2H, dd, J=7.6, 1.2 Hz), 7.62 (2H, d, J=9.2 Hz), 7.85 (1H, s), 8.02 (1H, dd, J=4.8, 1.6 Hz), 9.62 (1H, br-s)

Elementary analysis for C$_{23}$H$_{19}$N$_3$O$_3$S:

|  | C | H | N |
|---|---|---|---|
| Calculated: | 66.17 | 4.59 | 10.06 |
| Found: | 66.15 | 4.68 | 10.04 |

Example 30

N-(2-Anilino-3-pyridyl)-4-cyanobenzenesulfonamide:

Chemical formula 68

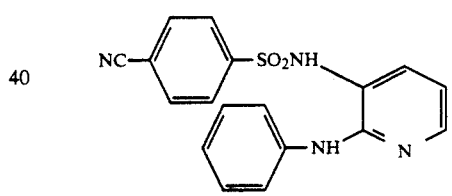

The title compound was produced in the same manner as that of Example 1.

Melting point: 155° to 157° C. (recrystallized from methanol)

FAB mass spectrometry m/z: 351 ([M+H]+)

$^1$H-NMR (DMSO-d$_6$) δ (ppm): 6.80 (1H, dd, J=7.6, 4.8 Hz), 6.90 (1H, t, J=7.6 Hz), 7.20 (2H, t, J=7.6 Hz), 7.31 (2H, d, J=7.6 Hz), 7.36 (1H, dd, J=7.6, 1.6 Hz), 7.76 (2H, d, J=7.6 Hz), 7.86-7.89 (3H, m), 8.05 (1H, br), 9.90 (1H, br-s)

Elementary analysis for C$_{18}$H$_{14}$N$_4$O$_2$S:

|  | C | H | N |
|---|---|---|---|
| Calculated: | 61.70 | 4.03 | 15.99 |
| Found: | 61.73 | 4.14 | 15.75 |

Example 31

N-(2-Anilino-3-pyridyl)-2,4-dimethoxybenzenesulfonamide:

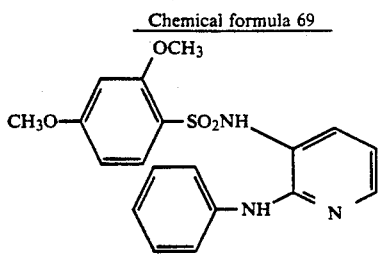

The title compound was produced in the same manner as that of Example 1.

Melting point: 176° to 178° C. (recrystallized from ethanol)

FAB mass spectrometry m/z: 386 ([M+H]+)

$^1$H-NMR (DMSO-d$_6$) δ (ppm): 3.76 (3H, s), 3.81 (3H, s), 6.53 (1H, dd, J=8.8, 2.4 Hz), 6.59 (1H, d, J=2.4 Hz), 6.69 (1H, dd, J=7.6, 4.8 Hz), 6.92 (1H, t, J=7.6 Hz), 7.25 (2H, t, J=7.6 Hz), 7.33 (1H, dd, J=7.6, 1.6 Hz), 7.50 (2H, d, J=7.6 Hz), 7.55 (1H, d, J=8.8 Hz), 7.92 (1H, dd, J=4.8, 1.6 Hz), 8.07 (1H, s)

| Elementary analysis for C$_{19}$H$_{19}$N$_3$O$_4$S: | | | |
|---|---|---|---|
| | C | H | N |
| Calculated: | 59.21 | 4.97 | 10.90 |
| Found: | 59.19 | 5.04 | 10.91 |

EXAMPLE 32

N-(2-Anilino-3-pyridyl)-2-chlorobenzenesulfonamide:

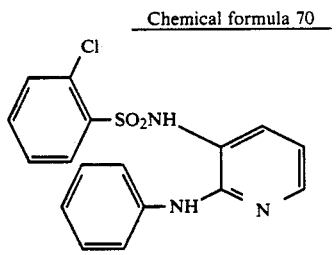

The title compound was produced in the same manner as that of Example 1.

Melting point: 140° to 141° C. (recrystallized from toluene)

FAB mass spectrometry m/z: 360 ([M+H]+)

$^1$H-NMR (DMSO-d$_6$) δ (ppm): 6.72 (1H, dd, J=7.6, 4.8 Hz), 6.93 (1H, t, J=7.6 Hz), 7.25 (2H, t, J=7.6 Hz), 7.31 (1H, dd, J=7.6, 1.6 Hz), 7.42–7.46 (1H, m), 7.49 (2H, d, J=7.6 Hz), 7.56–7.59 (2H, m), 7.87 (1H, d, J=7.6 Hz), 7.95–8.01 (2H, m), 10.14 (1H, br-s)

| Elementary analysis for C$_{17}$H$_{14}$ClN$_3$O$_2$S: | | | |
|---|---|---|---|
| | C | H | N |
| Calculated: | 56.74 | 3.92 | 11.68 |
| Found: | 56.86 | 4.06 | 11.62 |

EXAMPLE 33

4-Acetyl-N-(2-anilino-3-pyridyl)benzenesulfonamide:

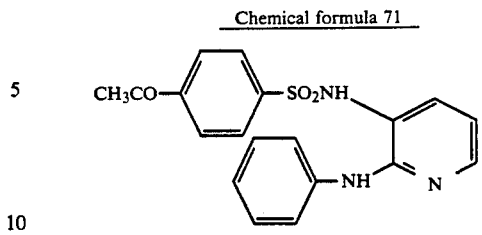

The title compound was produced in the same manner as that of Example 1.

Melting point: 171° to 173° C. (recrystallized from ethanol)

FAB mass spectrometry m/z: 368 ([M+H]+)

$^1$H-NMR (DMSO-d$_6$) δ (ppm): 2.46 (3H, s), 6.78 (1H, dd, J=7.6, 4.8 Hz), 6.85 (1H, t, J=7.6 Hz), 7.15 (2H, t, J=7.6 Hz), 7.31 (2H, dd, J=7.6, 1.2 Hz), 7.35 (1H, dd, J=7.6, 1.6 Hz), 7.74 (2H, d, J=8.4 Hz), 7.85 (1H, s), 7.94 (2H, d, J=8.4 Hz), 8.03 (1H, dd, J=4.8, 1.6 Hz), 9.83 (1H, br-s)

| Elementary analysis for C$_{19}$H$_{17}$N$_3$O$_3$S: | | | |
|---|---|---|---|
| | C | H | N |
| Calculated: | 62.11 | 4.66 | 11.44 |
| Found: | 62.31 | 4.78 | 11.19 |

EXAMPLE 34

N-[2-[(3-Hydroxyphenyl)amino]-3-pyridyl]-4-methoxybenzenesulfonamide:

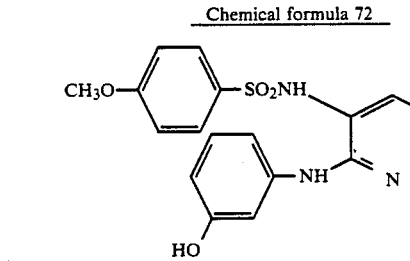

4.0 g (19.9 mmol) of the compound produced in Production Example 6 was reacted with 4.11 g (19.9 mmol) of p-methoxybenzenesulfonyl chloride and the product was treated in the same manner as that of Example 1 to obtain 5.0 g of the title compound.

Melting point: 181° to 182° C. (recrystallized from toluene)

FAB mass spectrometry m/z: 372 ([M+H]+)

$^1$H-NMR (DMSO-d$_6$) δ (ppm): 3.72 (3H, s), 6.31 (1H, dd, J=8.0, 2.0 Hz), 6.72 (1H, dd, J=7.6, 4.8 Hz), 6.79 (1H, d, J=8.0 Hz), 6.96 (2H, d, J=8.8 Hz), 6.98 (1H, t, J=8.0 Hz), 7.02 (1H, t, J=2.0 Hz), 7.25 (1H, dd, J=7.6, 1.6 Hz), 7.59 (2H, d, J=8.8 Hz), 7.77 (1H, s), 7.99 (1H, dd, J=4.8, 1.6 Hz), 9.18 (1H, s), 9.56 (1H, br-s)

| Elementary analysis for C$_{18}$H$_{17}$N$_3$O$_4$S: | | | |
|---|---|---|---|
| | C | H | N |
| Calculated: | 58.21 | 4.61 | 11.31 |
| Found: | 58.26 | 4.67 | 10.99 |

EXAMPLE 35

N[2-[(4-Ethoxyphenyl)amino]-3-pyridyl]-4-methoxybenzenesulfonamide:

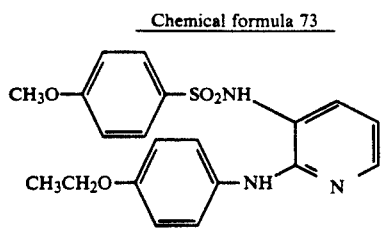

Chemical formula 73

The title compound was produced in the same manner as that of Example 1.

Melting point: 144° to 146° C. (recrystallized from ethanol)

FAB mass spectrometry m/z: 400 ([M+H]+)

$^1$H-NMR (DMSO-d$_6$) δ (ppm): 1.31 (3H, t, J=2.8 Hz), 3.73 (3H, s), 3.97 (2H, q, J=2.8 Hz), 6.65 (1H, dd, J=4.8, 7.6 Hz), 6.80 (2H, d, J=8.8 Hz), 6.98 (2H, d, J=8.8 Hz), 7.21 (1H, dd, J=1.6, 7.6 Hz), 7.28 (2H, d, J=8.8 Hz), 7.60 (2H, d, J=8.8 Hz), 7.72 (1H, br-s), 7.92 (1H, dd, J=1.6, 4.8 Hz), 9.47 (1H, br-s)

| Elementary analysis for C$_{20}$H$_{21}$N$_3$O$_4$S: | | | |
|---|---|---|---|
| | C | H | N |
| Calculated: | 60.13 | 5.30 | 10.52 |
| Found: | 60.02 | 5.27 | 10.21 |

EXAMPLE 36

N-[2-[(4-hydroxy-3-methylphenyl)amino]-3-pyridyl]-4-methoxybenzenesulfonamide:

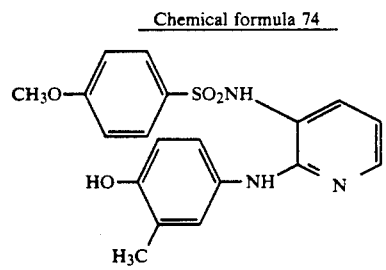

Chemical formula 74

The title compound was produced in the same manner as that of Example 1.

Melting point: 89° to 91° C. (recrystallized from toluene)

FAB mass spectrometry m/z: 386 ([M+H]+)

$^1$H-NMR (DMSO-d$_6$) δ (ppm): 2.07 (3H, s), 3.75 (3H, s), 6.60 (1H, dd, J=4.8, 7.6 Hz), 6.63 (1H, d, J=8.4 Hz), 6.93 (1H, d, J=2.8 Hz), 6.98-7.03 (3H, m), 7.18 (1H, dd, J=1.6, 7.6 Hz), 7.50 (1H, br-s), 7.60 (2H, d, J=8.8 Hz), 7.88 (1H, dd, J=1.6, 4.8 Hz), 8.87 (1H, s), 9.44 (1H, br-s)

| Elementary analysis for C$_{19}$H$_{19}$N$_3$O$_4$S: | | | |
|---|---|---|---|
| | C | H | N |
| Calculated: | 59.21 | 4.97 | 10.90 |
| Found: | 58.97 | 5.06 | 10.53 |

EXAMPLE 37

Ethyl 4-[[3-(4-methoxybenzenesulfonamido)-2-pyridyl]amino]benzoate:

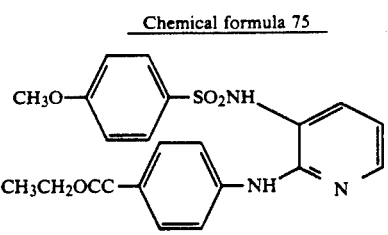

Chemical formula 75

The title compound was produced in the same manner as that of Example 1.

Melting point: 172° to 173° C. (recrystallized from ethanol)

FAB mass spectrometry m/z: 428 ([M+H]+)

$^1$H-NMR (DMSO-d$_6$) δ (ppm): 1.31 (3H, t, J=3.2 Hz), 3.63 (3H, s), 4.27 (2H, q, J=3.2 Hz), 6.88 (2H, d, J=8.8 Hz), 6.88 (1H, dd, J=4.8, 7.6 Hz), 7.38 (1H, dd, J=1.6, 7.6 Hz), 7.51 (2H, d, J=8.8 Hz), 7.54 (2H, d, J=8.8 Hz), 7.80 (2H, d, J=8.8 Hz), 8.10 (1H, dd, J=1.6, 4.8 Hz), 8.34 (1H, br-s), 9.58 (1H, br-s)

| Elementary analysis for C$_{21}$H$_{21}$N$_3$O$_5$S: | | | |
|---|---|---|---|
| | C | H | N |
| Calculated: | 59.00 | 4.95 | 9.83 |
| Found: | 58.98 | 4.91 | 9.63 |

Example 38

4-Methoxy-N-[2-[(4-methylthiophenyl)amino]-3-pyridyl]-benzenesulfonamide:

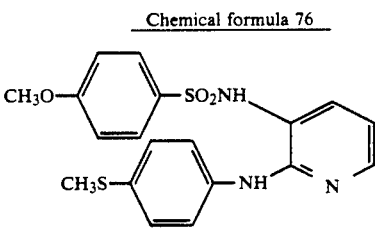

Chemical formula 76

The title compound was produced in the same manner as that of Example 1.

Melting point: 148° to 149° C. (recrystallized from ethanol)

FAB mass spectrometry m/z: 402 ([M+H]+)

$^1$H-NMR (DMSO-d$_6$) δ (ppm): 2.43 (3H, s), 3.70 (3H, s), 6.73 (1H, dd, J=4.8, 7.6 Hz), 6.94 (2H, d, J=8.8 Hz), 7.17 (2H, d, J=8.8 Hz), 7.26 (1H, dd, J=1.6, 7.6 Hz), 7.39 (2H, d, J=8.8 Hz), 7.57 (2H, d, J=8.8 Hz), 7.93 (1H, br-s), 7.98 (1H, dd, J=1.6, 4.8 Hz), 9.51 (1H, br-s)

| Elementary analysis for C$_{19}$H$_{19}$N$_3$O$_3$S$_2$: | | | |
|---|---|---|---|
| | C | H | N |
| Calculated: | 56.84 | 4.77 | 10.47 |
| Found: | 56.90 | 4.77 | 10.24 |

Example 39

Potassium 4-[[3-(4-methoxybenzenesulfonamido)-2-pyridyl]amino]phenyl sulfate:

Chemical formula 77

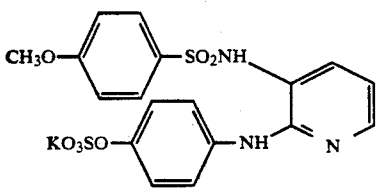

2.0 g (5.38 mmol) of the compound of Example 6 was dissolved in 20 ml of pyridine. 800 mg (6.87 mmol) of chlorosulfonic acid (95%) was added dropwise thereto at −15° to −10° C. The temperature was slowly elevated to room temperature and the mixture was stirred for 3 days. A 1N aqueous potassium carbonate solution was added to the reaction mixture to adjust the pH to 8 to 9. The solvent was distilled off under reduced pressure. Water and ethyl acetate were added to the residue and an aqueous layer thus formed was separated, concentrated, purified by silica gel column chromatography and precipitated with methanol/dichloromethane to obtain 1.58 g of the title compound.

Melting point: 165° to 166° C.

FAB mass spectrometry m/z: 528 ([M+K]+)

$^1$H-NMR (DMSO-d$_6$) δ (ppm): 3.73 (3H, s), 6.68 (1H, dd, J=4.8, 8.0 Hz), 6.98 (2H, d, J=8.8 Hz), 7.02 (2H, d, J=8.4 Hz), 7.25–7.27 (3H, m), 7.61 (2H, d, J=8.8 Hz), 7.83 (1H, s), 7.94 (1H, dd, J=1.2, 4.8 Hz), 9.55 (1H, s)

| Elementary analysis for C$_{18}$H$_{16}$N$_3$O$_7$S$_2$K.3/2H$_2$O: | | | |
|---|---|---|---|
| | C | H | N |
| Calculated: | 41.85 | 3.71 | 8.13 |
| Found: | 41.88 | 3.41 | 8.08 |

Example 40

4-Methoxy-N-[2-[(4-phenoxyphenyl)amino]-3-pyridyl]-benzenesulfonamide:

Chemical formula 78

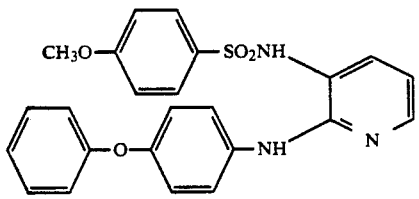

The title compound was produced in the same manner as that of Example 1.

Melting point: 174° to 176° C. (recrystallized from ethanol)

FAB mass spectrometry m/z: 448 ([M+H]+)

$^1$H-NMR (DMSO-d$_6$) δ (ppm): 3.75 (3H, s), 6.72 (1H, dd, J=4.8, 7.6 Hz), 6.92 (2H, d, J=8.8 Hz), 6.91–6.97 (2H, m), 6.96 (2H, d, J=8.8 Hz), 7.05–7.10 (1H, m), 7.27 (1H, dd, J=1.6, 7.6 Hz), 7.32–7.40 (2H, m), 7.43 (2H, d, J=8.8 Hz), 7.59 (2H, d, J=8.8 Hz), 7.92 (1H, br-s), 7.98 (1H, dd, J=1.6, 4.8 Hz), 9.44 (1H, br-s)

| Elementary analysis for C$_{24}$H$_{21}$N$_3$O$_4$S: | | | |
|---|---|---|---|
| | C | H | N |
| Calculated: | 64.41 | 4.73 | 9.39 |
| Found: | 64.71 | 4.96 | 9.30 |

Example 41

4-[[3-(4-Methoxybenzenesulfonamido)-2-pyridyl]amino]benzoic acid:

Chemical formula 79

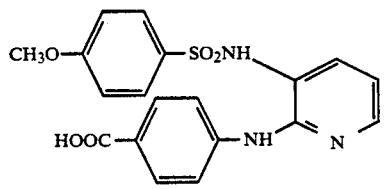

The title compound was produced by an alkaline hydrolysis of the compound of Example 37 in an ordinary manner.

Melting point: 248° to 250° C. (recrystallized from ethanol)

FAB mass spectrometry m/z: 400 ([M+H]+)

$^1$H-NMR (DMSO-d$_6$) δ (ppm): 3.64 (3H, s), 6.87 (1H, dd, J=4.8, 7.6 Hz), 6.89 (2H, d, J=8.8 Hz), 7.37 (1H, dd, J=1.6, 7.6 Hz), 7.49 (2H, d, J=8.8 Hz), 7.54 (2H, d, J=8.8 Hz), 7.78 (2H, d, J=8.8 HZ), 8.09 (1H, dd, J=1.6, 4.8 Hz), 8.29 (1H, br-s), 9.58 (1H, br-s), 12.44 (1H, br)

| Elementary analysis for C$_{19}$H$_{17}$N$_3$O$_5$S: | | | |
|---|---|---|---|
| | C | H | N |
| Calculated: | 57.13 | 4.29 | 10.52 |
| Found: | 57.10 | 4.42 | 10.35 |

Example 42

N-[2-[(4-Chlorophenyl)amino]-3-pyridyl]-4-methoxybenzenesulfonamide:

Chemical formula 80

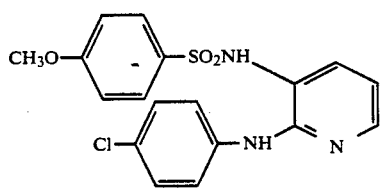

The title compound was produced in the same manner as that of Example 1.

Melting point: 205° to 207° C. (decomp.) (recrystallized from ethanol)

FAB mass spectrometry m/z: 390 ([M+H]+)

$^1$H-NMR (DMSO-d$_6$) δ (ppm): 3.70 (3H, s), 6.78 (1H, dd, J=7.6, 4.8 Hz), 6.93 (2H, d, J=8.8 Hz), 7.24 (2H, d, J=8.8 Hz), 7.30 (1H, dd, J=7.6, 2.0 Hz), 7.45 (2H, d, J=8.8 Hz), 7.56 (2H, d, J=8.8 Hz), 8.02 (1H, dd, J=4.8, 2.0 Hz), 8.05 (1H, s), 9.51 (1H, br-s)

| Elementary analysis for C_{18}H_{16}ClN_3O_3S: | | | |
|---|---|---|---|
| | C | H | N |
| Calculated: | 55.46 | 4.14 | 10.78 |
| Found: | 55.44 | 4.32 | 10.71 |

Example 43

N-[2-[(2-Hydroxyphenyl)amino]-3-pyridyl]-4-methoxybenzenesulfonamide:

Chemical formula 81

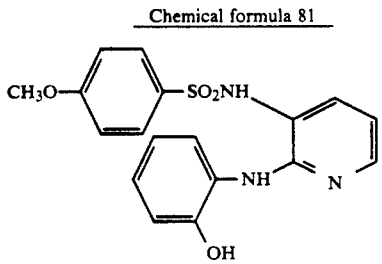

The title compound was produced in the same manner as that of Example 1.

Melting point: 154° to 155° C. (recrystallized from toluene)

FAB mass spectrometry m/z: 372 ([M+H]+)

$^1$H-NMR (DMSO-d$_6$) δ (ppm): 3.81 (3H, s), 6.63 (1H, dd, J=8.0, 5.2 Hz), 6.72–6.79 (2H, m), 6.82–6.86 (2H, m), 7.07 (2H, d, J=8.8 Hz), 7.66 (2H, d, J=8.8 Hz), 8.05 (1H, dd, J=5.2, 1.6 Hz), 8.15 (1H, s), 8.29 (1H, dd, J=7.6, 2.0 Hz), 9.70 (1H, s), 9.94 (1H, s)

| Elementary analysis for C_{18}H_{17}N_3O_4S: | | | |
|---|---|---|---|
| | C | H | N |
| Calculated: | 58.22 | 4.61 | 11.32 |
| Found: | 58.39 | 4.60 | 11.20 |

Example 44

N-(2-Anilino-3-pyridyl)-2,4,6-trimethylbenzenesulfonamide:

Chemical formula 82

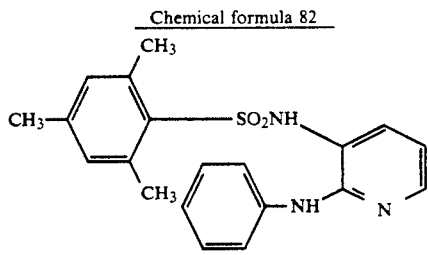

The title compound was produced in the same manner as that of Example 1.

Melting point: 140° to 142° C. (recrystallized from ethanol)

FAB mass spectrometry m/z: 368 ([M+H]+)

$^1$H-NMR (DMSO-d$_6$) δ (ppm): 2.16 (3H, s), 2.41 (6H, s), 6.70 (1H, dd, J=7.6, 4.8 Hz), 6.89–6.94 (3H, m), 7.08 (1H, dd, J=7.6, 1.6 Hz), 7.24 (2H, t, J=7.6 Hz), 7.43 (2H, d, J=7.6 Hz), 7.89 (1H, s), 8.01 (1H, dd, J=4.8, 1.6 Hz), 9.58 (1H, s)

| Elementary analysis for C_{20}H_{21}N_3O_2S: | | | |
|---|---|---|---|
| | C | H | N |
| Calculated: | 65.37 | 5.76 | 11.43 |
| Found: | 65.45 | 5.67 | 11.34 |

Example 45

N-(2-Anilino-3-pyridyl)-4-chloro-2,5-dimethylbenzenesulfonamide:

Chemical formula 83

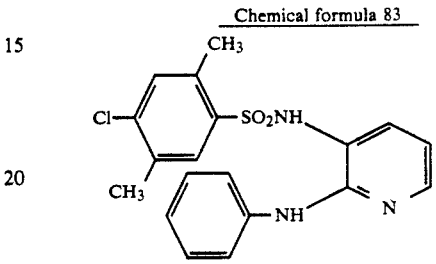

The title compound was produced in the same manner as that of Example 1.

Melting point: 153° to 154° C. (recrystallized from ethanol)

FAB mass spectrometry m/z: 388 ([M+H]+)

$^1$H-NMR (DMSO-d$_6$) δ (ppm): 2.20 (3H, s), 2.41 (3H, s), 6.75 (1H, dd, J=7.6, 4.8 Hz), 6.91 (1H, t, J=7.6 Hz), 7.23 (2H, t, J=7.6 Hz), 7.26 (1H, dd, J=7.6, 1.6 Hz), 7.33 (1H, s), 7.38 (2H, d, J=7.6 Hz), 7.63 (1H, s), 7.93 (1H, s), 8.02 (1H, dd, J=4.8, 1.6 Hz), 9.76 (1H, s)

| Elementary analysis for C_{19}H_{18}ClN_3O_2S: | | | |
|---|---|---|---|
| | C | H | N |
| Calculated: | 58.83 | 4.68 | 10.83 |
| Found: | 58.97 | 4.64 | 10.85 |

Example 46

4-Methoxy-N-[2-[(2-methoxy-5-pyridyl)amino]-3-pyridyl]benzenesulfonamide:

Chemical formula 84

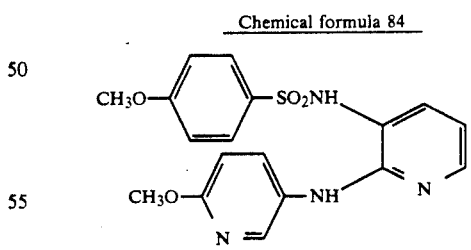

The title compound was produced in the same manner as that of Example 1.

Melting point: 159° to 160° C. (recrystallized from ethanol)

FAB mass spectrometry m/z: 387 ([M+H]+)

$^1$H-NMR (DMSO-d$_6$) δ (ppm): 3.73 (3H, s), 3.81 (3H, s), 6.68–6.73 (2H, m), 6.98 (2H, d, J=8.8 Hz), 7.25 (1H, dd, J=7.6, 1.2 Hz), 7.60 (2H, d, J=8.8 Hz), 7.72 (1H, dd, J=8.8, 2.8 Hz), 7.90 (1H, s), 7.93 (1H, dd, J=4.8, 1.2 Hz), 8.13 (1H, d, J=2.8 Hz), 9.44 (1H, br-s)

| Elementary analysis for $C_{18}H_{18}N_4O_4S$: | | | |
|---|---|---|---|
| | C | H | N |
| Calculated: | 55.95 | 4.69 | 14.50 |
| Found: | 55.95 | 4.72 | 14.46 |

Example 47

N-(4-Anilino-6-methoxy-5-pyrimidyl)-4-methoxybenzenesulfonamide:

Chemical formula 85

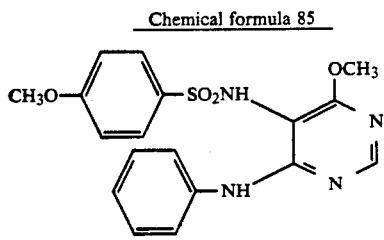

The title compound was produced in the same manner as that of Example 1.

Melting point: 159° to 160° C. (recrystallized from ethanol)

FAB mass spectrometry m/z: 387 ([M+H]$^+$)

$^1$H-NMR (DMSO-d$_6$) δ (ppm): 3.38 (3H, s), 3.80 (3H, s), 7.01–7.07 (3H, m), 7.30 (2H, t, J=8.0 Hz), 7.57 (2H, dd, J=8.0, 0.8 Hz), 7.63 (2H, d, J=8.8 Hz), 8.20 (1H, s), 8.33 (1H, s), 9.29 (1H, s)

| Elementary analysis for $C_{18}H_{18}N_4O_4S$: | | | |
|---|---|---|---|
| | C | H | N |
| Calculated: | 55.95 | 4.70 | 14.50 |
| Found: | 55.90 | 4.71 | 14.49 |

Example 48

N-(4-Anilino-6-chloro-5-pyrimidyl)-4-methoxybenzenesulfonamide:

Chemical formula 86

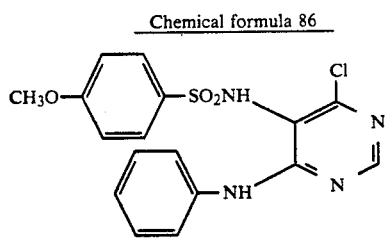

The title compound was produced in the same manner as that of Example 1.

Melting point: 174° to 175° C. (recrystallized from ethanol)

FAB mass spectrometry m/z: 391 ([M+H]$^+$)

$^1$H-NMR (DMSO-d$_6$) δ (ppm): 3.75 (3H, s), 7.03 (2H, d, J=8.8 Hz), 7.09 (1H, t, J=7.6 Hz), 7.32 (2H, t, J=7.6 Hz), 7.46 (2H, d, J=7.6 Hz), 7.65 (2H, d, J=8.8 Hz), 8.29 (1H, s), 8.63 (1H, s), 9.74 (1H, br-s)

| Elementary analysis for $C_{17}H_{15}N_4O_3SCl$: | | | |
|---|---|---|---|
| | C | H | N |
| Calculated: | 52.24 | 3.87 | 14.33 |

| Elementary analysis for $C_{17}H_{15}N_4O_3SCl$: | | | |
|---|---|---|---|
| | C | H | N |
| Found: | 52.29 | 3.85 | 14.27 |

Example 49

N-(2-Anilino-6-dimethylamino-3-pyridyl)-4-methoxybenzenesulfonamide:

Chemical formula 87

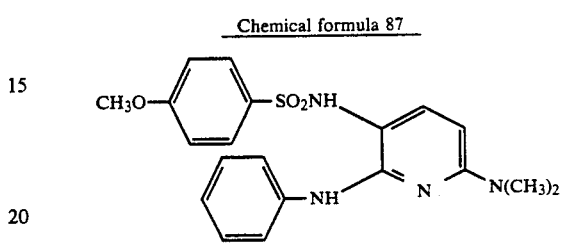

The title compound was produced in the same manner as that of Example 1.

Melting point: 152° to 153° C. (recrystallized from ethyl acetate/n-hexane):

FAB mass spectrometry m/z: 399 ([M+H]$^+$)

$^1$H-NMR (CDCl$_3$) δ (ppm): 3.04 (6H, s), 3.83 (3H, s), 5.71 (1H, d, J=8.8 Hz), 5.75 (1H, s), 6.59 (1H, d, J=8.8 Hz), 6.91–6.96 (3H, m), 7.24–7.28 (3H, m), 7.53 (2H, d, J=7.6 Hz), 7.72 (2H, d, J=9.2 Hz)

| Elementary analysis for $C_{20}H_{22}N_4O_3S$: | | | |
|---|---|---|---|
| | C | H | N |
| Calculated: | 60.28 | 5.56 | 14.06 |
| Found: | 60.21 | 5.47 | 13.92 |

Example 50

N-(2-Anilino-6-chloro-3-pyridyl)-4-methoxybenzenesulfonamide:

Chemical formula 88

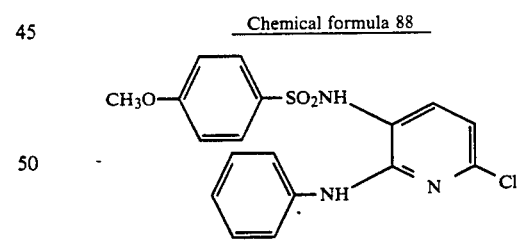

The title compound was produced in the same manner as that of Example 1.

Melting point: 206° to 208° C. (recrystallized from ethanol)

FAB mass spectrometry m/z: 390 ([M+H]$^+$)

$^1$H-NMR (DMSO-d$_6$) δ (ppm): 3.71 (3H, s), 6.79 (1H, d, J=8.0 Hz), 6.93–6.99 (3H, m), 7.26 (3H, t, J=8.0 Hz), 7.38 (2H, d, J=8.0 Hz), 7.61 (2H, d, J=9.2 Hz), 8.15 (1H, s), 9.56 (1H, s)

| Elementary analysis for $C_{18}H_{16}ClN_3O_3S$: | | | |
|---|---|---|---|
| | C | H | N |
| Calculated: | 55.46 | 4.14 | 10.78 |

| Elementary analysis for $C_{18}H_{16}ClN_3O_3S$: | | | |
|---|---|---|---|
| | C | H | N |
| Found: | 55.49 | 4.04 | 10.62 |

Example 51

N-(4-Anilino-3-pyridyl)-4-methoxybenzenesulfonamide:

Chemical formula 89

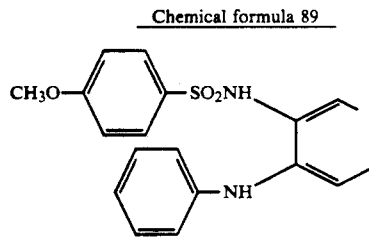

The title compound was produced in the same manner as that of Example 1.

Melting point: 201° to 202° C. (recrystallized from ethanol)

FAB mass spectrometry m/z: 356 ([M+H]$^+$)

$^1$H-NMR (DMSO-d$_6$) δ (ppm): 3.75 (3H, s), 6.92 (1H, d, J=6.4 Hz), 6.95 (2H, d, J=8.8 Hz), 7.13–7.20 (3H, m), 7.39 (2H, t, J=8.0 Hz), 7.67 (2H, d, J=8.8 Hz), 7.78 (1H, s), 7.82 (1H, d, J=5.6 Hz)

| Elementary analysis for $C_{18}H_{17}N_3O_3S$: | | | |
|---|---|---|---|
| | C | H | N |
| Calculated: | 60.83 | 4.82 | 11.82 |
| Found: | 60.78 | 4.77 | 11.84 |

Example 52

N-[2-[(4-Dimethylcarbamoyloxyphenyl)amino]-3-pyridyl]-4-methoxybenzenesulfonamide:

Chemical formula 90

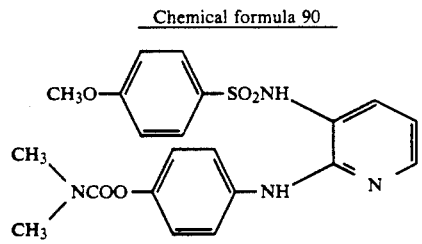

The title compound was produced in the same manner as that of Example 1.

Melting point: 202° to 203° C. (recrystallized from ethanol)

FAB mass spectrometry m/z: 443 ([M+H]$^+$)

$^1$H-NMR (DMSO-d$_6$) δ (ppm): 2.90 (3H, s), 3.03 (3H, s), 3.72 (3H, s), 6.72 (1H, dd, J=7.6, 4.8 Hz), 6.96 (2H, d, J=8.8Hz), 6.97 (2H, d, J=8.8 Hz), 7.26 (1H, dd, J=7.6, 1.6 Hz), 7.41 (2H, d, J=8.8 Hz), 7.60 (2H, d, J=8.8 Hz), 7.94 (1H, s), 7.97 (1H, dd, J=4.8, 1.6 Hz), 9.52 (1H, br-s)

| Elementary analysis for $C_{21}H_{22}N_4O_5S$: | | | |
|---|---|---|---|
| | C | H | N |
| Calculated: | 57.00 | 5.01 | 12.66 |
| Found: | 57.35 | 4.98 | 12.55 |

Example 53

N-(4-Anilino-5-pyrimidyl)-4-methoxybenzenesulfonamide:

Chemical formula 91

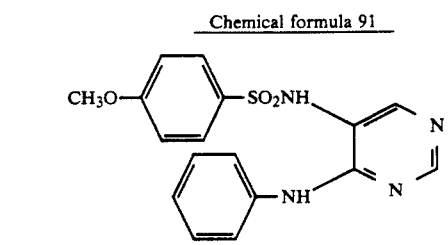

The title compound was produced by catalytically reducing the compound of Example 48 in the presence of palladium/carbon in an ordinary manner.

Melting point: 189° to 190° C. (recrystallized from ethanol)

FAB mass spectrometry m/z: 357 ([M+H]$^+$)

$^1$H-NMR (DMSO-d$_6$) δ (ppm): 3.73 (3H, s), 7.01 (2H, d, J=8.8 Hz), 7.05 (1H, t, J=8.0 Hz), 7.30 (2H, t, J=8.0 Hz), 7.50 (2H, d, J=8.0 Hz), 7.64 (2H, d, J=8.8 Hz), 7.87 (1H, s), 8.40 (1H, s), 8.57 (1H, br-s)

| Elementary analysis for $C_{17}H_{16}N_4O_3S$: | | | |
|---|---|---|---|
| | C | H | N |
| Calculated: | 57.29 | 4.53 | 15.72 |
| Found: | 57.25 | 4.68 | 15.36 |

Example 54

N-(2-Anilino-6-methoxy-3-pyridyl)-4-methoxybenzenesulfonamide:

Chemical formula 92

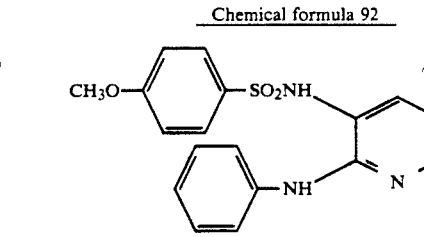

The title compound was produced in the same manner as that of Example 1.

Melting point: 187° to 188° C. (recrystallized from ethanol)

FAB mass spectrometry m/z: 386 ([M+H]$^+$)

$^1$H-NMR (DMSO-d$_6$) δ (ppm): 3.70 (3H, s), 3.77 (3H, s), 6.11 (1H, d, J=8.0 Hz), 6.89 (1H, t, J=7.6 Hz), 6.95 (2H, d, J=9.2 Hz), 7.07 (1H, d, J=8.0 Hz), 7.22 (2H, t, J=7.6 Hz), 7.43 (2H, d, J=7.6 Hz), 7.52 (2H, d, J=9.2 Hz), 7.83 (1H, br-s), 9.23 (1H, br-s)

| Elementary analysis for $C_{19}H_{19}N_3O_4S$: | | | |
|---|---|---|---|
| | C | H | N |
| Calculated: | 59.21 | 4.97 | 10.90 |
| Found: | 59.32 | 4.97 | 10.76 |

Example 55

N-(4,6-Dianilino-5-pyrimidyl)-4-methoxybenzenesulfonamide:

Chemical formula 93

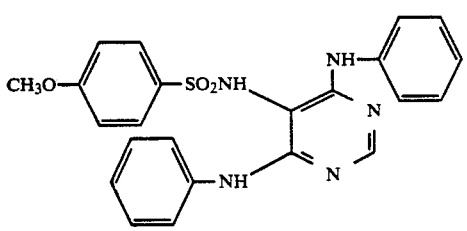

The title compound was produced in the same manner as that of Example 1.

Melting point: 149° to 151° C. (recrystallized from dichloromethane/n-hexane)

FAB mass spectrometry m/z: 448 ([M+H]+)

$^1$H-NMR (DMSO-d$_6$) δ (ppm): 3.53 (3H, s), 6.82 (2H, d, J=8.8 Hz), 6.96 (2H, t, J=7.6 Hz), 7.23 (4H, t, J=7.6 Hz), 7.40 (4H, d, J=7.6 Hz), 7.62 (2H, d, J=8.8 Hz), 8.05 (2H, s), 8.11 (1H, s), 8.90 (1H, s)

| Elementary analysis for $C_{23}H_{21}N_5O_3S$: | | | |
|---|---|---|---|
| | C | H | N |
| Calculated: | 61.73 | 4.73 | 15.65 |
| Found: | 61.91 | 4.72 | 15.74 |

Example 56

4-Methoxy-N-[2-(methylphenyl)amino-3-pyridyl]-benzenesulfonamide:

Chemical formula 94

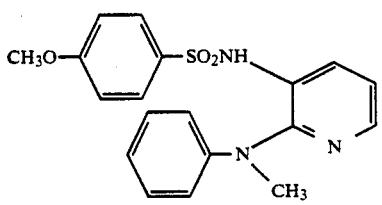

The title compound was produced in the same manner as that of Example 1.

Melting point: 80° to 81° C. (recrystallized from diisopropyl ether)

FAB mass spectrometry m/z: 370 ([M+H]+)

$^1$H-NMR (DMSO-d$_6$) δ (ppm): 3.01 (3H, s), 3.82 (3H, s), 6.46-6.51 (2H, m), 6.78-6.84 (1H, m), 7.04 (2H, d, J=8.8 Hz), 7.11-7.17 (2H, m), 7.17 (1H, dd, J=4.8, 8.0 Hz), 7.65 (1H, dd, J=1.6, 8.0 Hz), 7.68 (2H, d, J=8.8 Hz), 8.14 (1H, dd, J=1.6, 4.8 Hz), 9.30 (1H, br-s)

| Elementary analysis for $C_{19}H_{19}N_3O_3S$: | | | |
|---|---|---|---|
| | C | H | N |
| Calculated: | 61.77 | 5.18 | 11.38 |
| Found: | 61.85 | 5.28 | 11.36 |

Example 57

4-Methoxy-N-[2-[(2-pyrimidyl)amino]phenyl]benzenesulfonamide:

Chemical formula 95

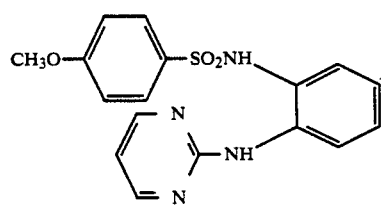

The title compound was produced in the same manner as that of Example 1.

Melting point: 193° to 195° C. (recrystallized from ethanol)

FAB mass spectrometry m/z: 357 ([M+H]+)

$^1$H-NMR (DMSO-d$_6$) δ (ppm): 3.70 (3H, s), 6.79-6.83 (3H, m), 6.96 (1H, dt, J=1.6, 8.4 Hz), 7.01 (1H, dd, J=1.6, 8.4 Hz), 7.19 (1H, dt, J=1.6, 8.4 Hz), 7.47 (2H, d, J=8.8 Hz), 7.87 (1H, dd, J=1.6, 8.4 Hz), 8.38 (2H, dd, J=1.6, 4.8 Hz), 8.54 (1H, br-s), 9.53 (1H, br-s)

| Elementary analysis for $C_{17}H_{16}N_4O_3S$: | | | |
|---|---|---|---|
| | C | H | N |
| Calculated: | 57.29 | 4.53 | 15.72 |
| Found: | 57.18 | 4.57 | 15.80 |

Example 58

N-(2-Anilinophenyl)-4-methoxybenzenesulfonamide:

Chemical formula 96

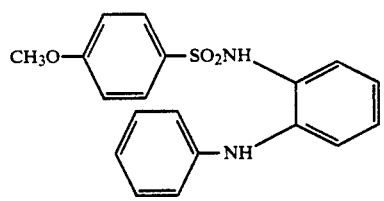

The title compound was produced in the same manner as that of Example 1.

Melting point: 140° to 142° C. (recrystallized from ethanol)

FAB mass spectrometry m/z: 354 (M+)

$^1$H-NMR (DMSO-d$_6$) δ (ppm): 3.69 (3H, s), 6.66-6.72 (2H, m), 6.81 (2H, d, J=8.8 Hz), 6.76-6.87 (2H, m), 7.04-7.17 (5H, m), 7.24 (1H, br-s), 7.52 (2H, d, J=8.8 Hz), 9.30 (1H, br-s)

| Elementary analysis for $C_{19}H_{18}N_2O_3S$: | | | |
|---|---|---|---|
| | C | H | N |
| Calculated: | 64.39 | 5.12 | 7.90 |

-continued

| Elementary analysis for C₁₉H₁₈N₂O₃S: | | | |
|---|---|---|---|
| | C | H | N |
| Found: | 64.49 | 5.17 | 7.77 |

Example 59

N-[2-[(4-Benzoyloxyphenyl)amino]-3-pyridyl]-4-methoxybenzenesulfonamide:

Chemical formula 97

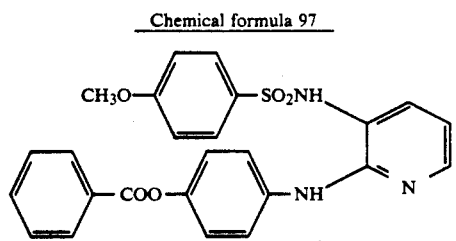

The title compound was produced in the same manner as that of Example 1.

Melting point: 208° to 210° C. (recrystallized from methanol)

FAB mass spectrometry m/z: 476 ([M+H]⁺)

¹H-NMR (DMSO-d₆) δ (ppm): 3.73 (3H, s), 6.75 (1H, d, J=4.8, 7.6 Hz), 6.98 (2H, d, J=8.8 Hz), 7.13 (2H, d, J=8.8 Hz), 7.28 (1H, dd, J=1.6, 7.6 Hz), 7.51 (2H, d, J=8.8 Hz), 7.61 (2H, d, J=8.8 Hz), 7.58–7.65 (2H, m), 7.72–7.78 (1H, m), 8.00 (1H, dd, J=1.6, 4.8 Hz), 8.04 (1H, br-s), 8.11–8.16 (2H,m), 9.54 (1H, br-s)

| Elementary analysis for C₂₅H₂₁N₃O₅S: | | | |
|---|---|---|---|
| | C | H | N |
| Calculated: | 63.15 | 4.45 | 8.84 |
| Found: | 62.95 | 4.57 | 8.76 |

Example 60

N-[2-[[4-(tert-Butoxycarbonylaminoacetyloxy)-phenyl]amino]-3-pyridyl]-4-methoxybenzenesulfonamide:

Chemical formula 98

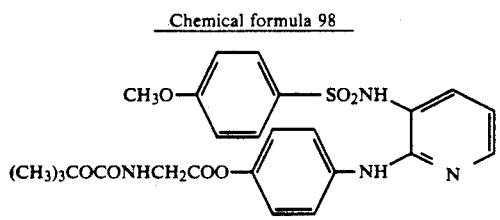

The title compound was produced in the same manner as that of Example 1.

¹H-NMR (CDCl₃) δ (ppm): 1.47 (9H, s), 3.82 (3H, s), 4.18 (2H, d, J=5.6 Hz), 5.17 (1H, br-s), 6.58 (2H, dd, J=7.6, 4.8 Hz), 6.89 (1H, dd, J=7.6, 1.6 Hz), 6.90 (2H, d, J=8.8 Hz), 7.00 (2H, d, J=8.8 Hz), 7.35 (1H, br-s), 7.47 (2H, d, J=8.8 Hz), 7.68 (2H, d, J=8.8 Hz), 8.10 (1H, dd, J=4.8, 1.6 Hz)

Example 61

N-[2-[[4-(Aminoacetyloxy)phenyl]amino]-3-pyridyl]-4-methoxybenzenesulfonamide dihydrochloride:

Chemical formula 99

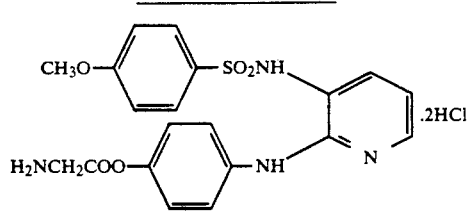

272 mg (0.515 mmol) of the compound of Example 60 was added to 10 ml of tetrahydrofuran. 2 ml of concentrated hydrochloric acid was added to the mixture and stirred at room temperature for 3 h. The solvent was distilled off under reduced pressure and the residue was recrystallized from ethanol to obtain 159 mg of the title compound.

Melting point: 196° to 199° C. (decomp.)

FAB mass spectrometry m/z: 429 ([M+H]⁺)

¹H-NMR (DMSO-d₆) δ (ppm): 3.71 (3H, s), 4.08–4.11 (2H, m), 6.78 (1H, dd, J=4.8, 7.6 Hz), 6.94 (2H, d, J=8.8 Hz), 7.04 (2H, d, J=8.8 Hz), 7.32 (1H, dd, J=1.6, 7.6 Hz), 7.48–7.51 (2H, m), 7.61 (2H, d, J=8.8 Hz), 7.97 (1H, dd, J=1.6, 4.8 Hz), 8.48 (3H, br-s), 9.84 (1H, br-s)

| Elementary analysis for C₂₀H₂₀N₄O₅S.2HCl.1/2H₂O: | | | |
|---|---|---|---|
| | C | H | N |
| Calculated: | 47.07 | 4.54 | 10.98 |
| Found: | 47.38 | 4.45 | 10.78 |

Example 62

4-Methoxy-N-[2-[(4-methoxyphenyl)amino]-3-pyridyl]-N-methylbenzenesulfonamide:

Chemical formula 100

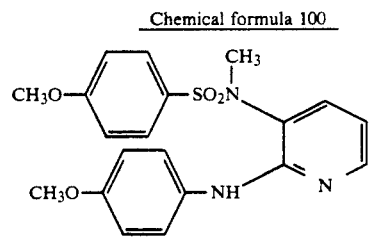

500 mg (1.3 mmol) of the compound of Example 4 was dissolved in 5 ml of dimethylformamide. 60 mg (1.5 mmol) of sodium hydride (60%) was added to the solution. The resulting solution was stirred at room temperature for 30 min and 95 μl (1.5 mmol) of methyl iodide was added thereto.

After stirring overnight, the solvent was distilled off under reduced pressure. The resultant residue was dissolved in ethyl acetate and the solution was washed with water. After drying over magnesium sulfate, it was concentrated and purified by silica gel column chromatography to obtain 290 mg of the title compound.

FAB mass spectrometry m/z: 400 ([M+H]⁺)

¹H-NMR (CDCl₃) δ (ppm): 3.15 (3H, s), 3.80 (3H, s), 3.88 (3H, s), 6.50 (1H, dd, J=4.8, 7.6 Hz), 6.67 (1H, dd, J=1.6, 7.6 Hz), 6.89 (2H, d, J=8.8 Hz), 6.98 (2H, d, J=8.8 Hz), 7.29 (1H, br-s), 7.47 (2H, d, J=8.8 Hz), 7.65 (2H, d, J=8.8 Hz), 8.09 (1H, dd, J=1.6, 4.8 Hz)

| Elementary analysis for $C_{20}H_{21}N_3O_4S$: | | | |
|---|---|---|---|
| | C | H | N |
| Calculated: | 60.14 | 5.30 | 10.52 |
| Found: | 60.08 | 5.39 | 10.29 |

Example 63

N-[2-[[4-(2-Aminobenzoyloxy)phenyl]amino]-3-pyridyl]-4-methoxybenzenesulfonamide:

Chemical formula 101

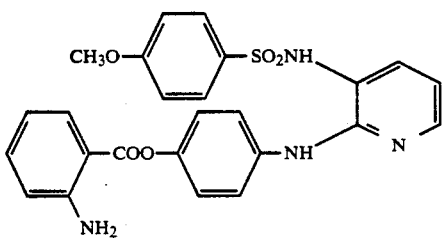

500 mg (1.35 mmol) of the compound of Example 6, 260 mg (1.59 mmol) of isatoic anhydride and 170 mg (1.39 mmol) of 4-dimethylaminopyridine were dissolved in 5 ml of dimethylformamide and the solution was stirred at 80° C. for 5 h. The solvent was distilled off under reduced pressure and ethyl acetate was added to the residue. A precipitate thus formed was recrystallized from ethanol to obtain 500 mg of the title compound.

Melting point: 221° to 225° C. (decomp.)
FAB mass spectrometry m/z: 491 ([M+H]+)
$^1$H-NMR (DMSO-d$_6$) δ (ppm): 3.74 (3H, s), 6.60 (1H, td, J=1.6, 8.4 Hz), 6.73 (2H, br-s), 6.74 (1H, dd, J=4.8, 8.0 Hz), 6.83 (1H, dd, J=0.8, 8.4 Hz), 6.98 (2H, d, J=8.8 Hz), 7.08 (2H, d, J=9.2 Hz), 7.27 (1H, dd, J=2.0, 8.0 Hz), 7.33 (1H, td, J=1.6, 7.2 Hz), 7.49 (1H, d, J=9.2 Hz), 7.61 (2H, d, J=8.8 Hz), 7.92 (1H, dd, J=1.6, 8.4 Hz), 7.99 (1H, dd, J=2.0, 4.8 Hz), 8.02 (1H, s), 9.60 (1H, br-s)

| Elementary analysis for $C_{25}H_{22}N_4O_5S$: | | | |
|---|---|---|---|
| | C | H | N |
| Calculated: | 61.21 | 4.52 | 11.42 |
| Found: | 60.98 | 4.52 | 11.24 |

Example 64

4-[[3-(4-Methoxybenzenesulfonamido)-2-pyridyl]amino]phenyl dihydrogenphosphate:

Chemical formual 102

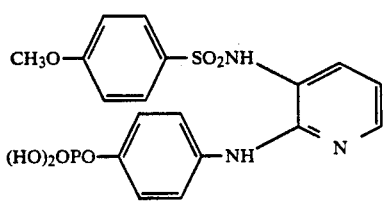

7.44 g (20 mmol) of the compound of Example 6 was suspended in 100 ml of phosphorus oxychloride and the suspension was heated under reflux until a homogeneous solution was obtained. Phosphorus oxychloride was distilled off under reduced pressure and then diisopropyl ether was added to the residue to form a solid, which was separated by filtration and suspended in 100 ml of tetrahydrofuran. 50 ml of water was added to the suspension under cooling with ice and stirred until a homogeneous solution was obtained. After the solvent was distilled off under reduced pressure, 100 ml of methanol and 100 ml of water were added to the residue to obtain a solution, which was concentrated under reduced pressure until an insoluble matter was formed. The insoluble matter was removed and the residue was further concentrated under reduced pressure and the resultant precipitate was separated by filtration to obtain 4.27 g of the title compound.

Melting point: 215° to 216° C.
FAB mass spectrometry m/z: 452 ([M+H]+)
$^1$H-NMR (DMSO-d$_6$) δ (ppm): 3.73 (3H, s), 6.70 (1H, dd, J=7.6, 4.8 Hz), 6.98 (2H, d, J=8.8 Hz), 7.02 (2H, d, J=8.8 Hz), 7.24 (1H, dd, J=7.6, 1.6 Hz), 7.35 (2H, d, J=8.8 Hz), 7.60 (2H, d, J=8.8 Hz), 7.88 (1H, s), 7.95 (1H, dd, J=4.8, 1.6 Hz), 9.50 (1H, br-s)

| Elementary analysis for $C_{18}H_{18}N_3O_7PS$: | | | |
|---|---|---|---|
| | C | H | N |
| Calculated: | 47.90 | 4.02 | 9.31 |
| Found: | 47.72 | 4.00 | 9.39 |

Example 65

3-[[3-(4-Methoxybenzenesulfonamido)-2-pyridyl]amino]phenyl dihydrogenphosphate:

Chemical formula 103

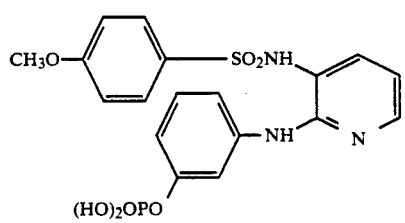

120 mg of the title compound was produced by reacting 1.00 g (2.7 mmol) of the compound of Example 34 with 10 ml of phosphorus oxychloride and the product was treated in the same manner as that of Example 64.

Melting point: 166° to 168° C.
FAB mass spectrometry m/z: 452 ([M+H]+)
$^1$H-NMR (DMSO-d$_6$) δ (ppm): 3.70 (3H, s), 6.73 (1H, d, J=7.6 Hz), 6.77 (1H, dd, J=7.6, 4.8 Hz), 6.95 (2H, d, J=8.8 Hz), 7.15 (1H, t, J=7.6 Hz), 7.21 (1H, d, J=7.6 Hz), 7.30 (1H, dd, J=7.6, 1.6 Hz), 7.37 (1H, s), 7.59 (2H, d, J=8.8 Hz), 8.01 (1H, dd, J=4.8, 1.6 Hz), 8.10 (1H, s), 9.61 (1H, br-s)

| Elementary analysis for $C_{18}H_{18}N_3O_7PS \cdot H_2O$: | | | |
|---|---|---|---|
| | C | H | N |
| Calculated: | 46.06 | 4.29 | 8.95 |
| Found: | 46.16 | 4.13 | 8.83 |

Example 66

4-Methoxy-N-[2-[[4-(4-methoxybenzenesulfonyloxy)-phenyl]amino]-3-pyridyl]benzenesulfonamide:

Chemical formula 104

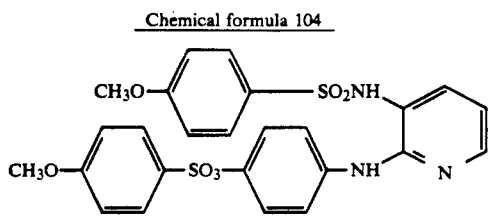

The compound produced in Production Example 4 was reacted with 4-methoxybenzenesulfonyl chloride in an equivalent ratio of 1:2 to obtain the title compound.

Melting point: 122° to 123° C. (recrystallized from ethanol)

FAB mass spectrometry m/z: 542 ([M+H]+)

$^1$H-NMR (DMSO-d$_6$) δ (ppm): 3.71 (3H, s), 3.88 (3H, s), 6.76 (1H, dd, J=7.6, 4.8 Hz), 6.84 (2H, d, J=8.8 Hz), 6.94 (2H, d, J=8.8 Hz), 7.17 (2H, d, J=8.8 Hz), 7.25 (1H, dd, J=7.6, 1.2 Hz), 7.42 (2H, d, J=8.8 Hz), 7.56 (2H, d, J=8.8 Hz), 7.76 (2H, d, J=8.8 Hz), 7.98 (1H, dd, J=4.8, 1.2 Hz), 8.06 (1H, s), 9.51 (1H, br-s)

| Elementary analysis for C$_{23}$H$_{23}$N$_3$O$_7$S$_2$: | | | |
|---|---|---|---|
| | C | H | N |
| Calculated: | 55.40 | 4.28 | 7.76 |
| Found: | 55.57 | 4.26 | 7.61 |

Example 67

N-[2-[(4-Hydroxyphenyl)amino]phenyl]-4-methoxybenzenesulfonamide:

Chemical formula 105

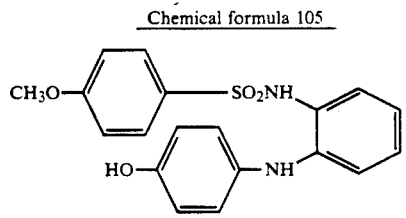

The title compound was produced in the same manner as that of Example 1.

Melting point: 163° to 164° C. (recrystallized from ethanol)

FAB mass spectrometry m/z: 370 (M+)

$^1$H-NMR (DMSO-d$_6$) δ (ppm): 3.76 (3H, s), 6.58-6.67 (5H, m), 6.77 (1H, br-s), 6.80 (1H, dd, J=1.6, 8.0 Hz), 6.90-7.00 (4H, m), 7.56 (2H, d, J=8.8 Hz), 9.05 (1H, s), 9.23 (1H, br-s)

| Elementary analysis for C$_{19}$H$_{18}$N$_2$O$_4$S: | | | |
|---|---|---|---|
| | C | H | N |
| Calculated: | 61.61 | 4.90 | 7.56 |
| Found: | 61.86 | 4.90 | 7.39 |

Example 68

4-Methoxy-N-[2-[(4-pivaloyloxyphenyl)amino]-3-pyridyl]-benzenesulfonamide:

Chemical formula 106

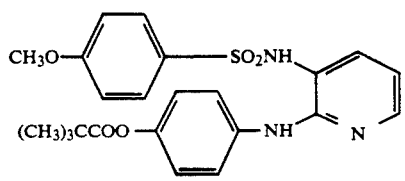

The title compound was produced in the same manner as that of Example 1.

Melting point: 188° to 189° C. (recrystallized from toluene)

FAB mass spectrometry m/z: 456 ([M+H]+)

$^1$H-NMR (DMSO-d$_6$) δ (ppm): 1.30 (9H, s), 3.72 (3H, s), 6.73 (1H, dd, J=7.6, 4.8 Hz), 6.94 (2H, d, J=8.8 Hz), 6.97 (2H, d, J=8.8 Hz), 7.25 (1H, dd, J=7.6, 1.6 Hz), 7.45 (2H, d, J=8.8 Hz), 7.60 (2H, d, J=8.8 Hz), 7.97-8.00 (2H, m), 9.52 (1H, br-s)

| Elementary analysis for C$_{23}$H$_{25}$N$_3$O$_5$S: | | | |
|---|---|---|---|
| | C | H | N |
| Calculated: | 60.64 | 5.53 | 9.22 |
| Found: | 60.57 | 5.43 | 8.95 |

Example 69

4-Methoxy-N-[2-[(4-pyridyl)amino]phenyl]benzenesulfonamide:

Chemical formula 107

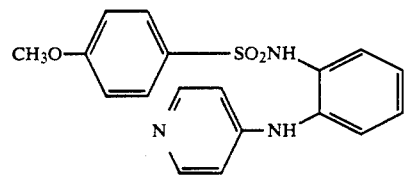

The title compound was produced in the same manner as that of Example 1.

Melting point: 185° to 187° C. (recrystallized from ethanol)

FAB mass spectrometry m/z: 356 ([M+H]+)

$^1$H-NMR (DMSO-d$_6$) δ (ppm): 3.67 (3H, s), 6.45 (2H, d, J=6.0 Hz), 6.73 (2H, d, J=8.8 Hz), 7.07 (1H, dt, J=7.6, 1.2 Hz), 7.16 (1H, dt, J=7.6, 1.2 Hz), 7.22 (1H, dd, J=7.6, 1.2 Hz), 7.28 (1H, dd, J=7.6, 1.2 Hz), 7.45 (2H, d, J=8.8 Hz), 7.90 (1H, br-s), 8.05 (2H, d, J=6.0 Hz)

| Elementary analysis for C$_{18}$H$_{17}$N$_3$O$_3$S: | | | |
|---|---|---|---|
| | C | H | N |
| Calculated: | 60.83 | 4.82 | 11.82 |
| Found: | 61.08 | 4.86 | 11.87 |

Example 70

N-[2-(4-Methoxybenzenesulfonamido)phenyl]-2-methylnicotinamide:

Chemical formula 108

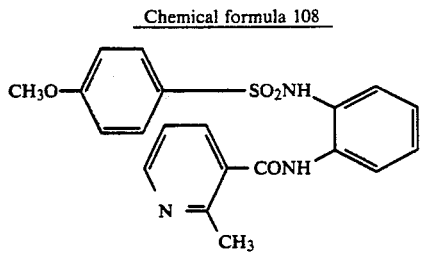

0.97 g (7 mmol) of 2-methylnicotinic acid was suspended in 4.5 ml of dichloromethane. 1.33 g (16.8 mmol) of pyridine and then 1.05 g (8.4 mmol) of thionyl chloride were added to the solution. The mixture was stirred at room temperature for 30 min and then a solution of 1.77 g (6.36 mmol) of the compound produced in Production Example 12 in 7 ml of dichloromethane was added thereto. After stirring overnight, an aqueous sodium hydrogencarbonate solution was added thereto and the product was extracted with dichloromethane. After concentration, ethanol was added to the concentrate and crystals thus formed were separated by filtration and recrystallized from ethanol to obtain 0.80 g of the title compound.

Melting point: 148° to 149° C.

FAB mass spectrometry m/z: 398 ([M+H]+)

$^1$H-NMR (DMSO-$d_6$) δ (ppm): 2.56 (3H, s), 3.80 (3H, s), 7.02 (2H, d, J=8.8 Hz), 7.08 (1H, dd, J=2.0, 8.4 Hz), 7.11 (1H, dt, J=1.6, 4.4 Hz), 7.18–7.27 (1H, m), 7.37 (1H, dd, J=4.8, 7.6 Hz), 7.57 (2H, d, J=8.8 Hz), 7.71–7.84 (2H, m), 8.58 (1H, dd, J=1.6, 4.8 Hz), 9.37 (1H, br-s), 9.60 (1H, br-s)

| Elementary analysis for $C_{20}H_{19}N_3O_4S$: | | |
|---|---|---|
| | C | H | N |
| Calculated: | 60.44 | 4.82 | 10.57 |
| Found: | 60.37 | 4.90 | 10.41 |

Example 71

N-[2-(4-Methoxybenzenesulfonamido)phenyl]-4-methylnicotinamide:

Chemical formula 109

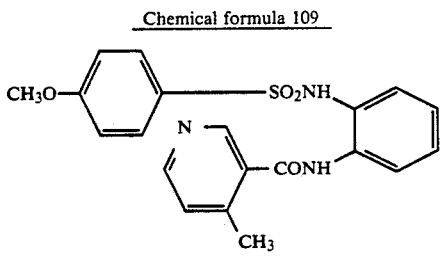

The title compound was produced in the same manner as that of Example 70.

Melting point: 199° to 200° C. (recrystallized from methanol)

FAB mass spectrometry m/z: 398 ([M+H]+)

$^1$H-NMR (DMSO-$d_6$) δ (ppm): 2.58 (39, s), 3.81 (3H, s), 7.00–7.07 (3H, m), 7.09–7.18 (1H, m), 7.19–7.27 (1H, m), 7.62 (2H, d, J=8.4 Hz), 7.74–7.80 (1H, m), 7.82 (1H, d, J=5.6 Hz), 8.80 (1H, d, J=5.6 Hz), 8.87 (1H, s), 9.62 (1H, br-s), 10.16 (1H, br-s)

Example 72

N-[2-(4-Methoxybenzenesulfonamido)phenyl]-3-methylisonicotinamide:

Chemical formula 110

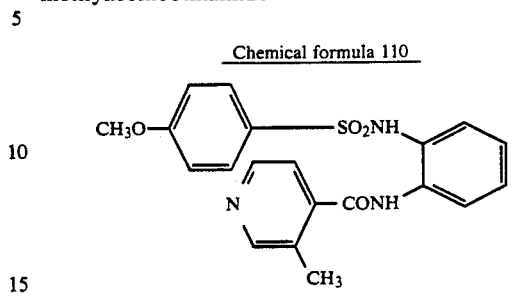

The title compound was produced in the same manner as that of Example 70.

Melting point: 194° to 195° C. (recrystallized from ethanol)

FAB mass spectrometry m/z: 398 ([M+H]+)

$^1$H-NMR (DMSO-$d_6$) δ (ppm): 2.36 (3H, s), 3.81 (3H, s), 7.03 (2H, d, J=8.8 Hz), 7.07 (1H, dd, J=1.6, 8.0 Hz), 7.12 (1H, dt, J=1.6, 8.0 Hz), 7.20–7.27 (1H, m), 7.36 (1H, d, J=4.8 Hz), 7.58 (2H, d, J=8.8 Hz), 7.76–7.83 (1H, m), 8.55–8.61 (2H, m), 9.39 (1H, br-s), 9.65 (1H, br-s)

| Elementary analysis for $C_{20}H_{19}N_3O_4S$: | | |
|---|---|---|
| | C | H | N |
| Calculated: | 60.44 | 4.82 | 10.57 |
| Found: | 60.29 | 4.83 | 10.49 |

Example 73

4-[[3-(4-Methoxybenzenesulfonamido)-2-pyridyl]amino]phenyl β-D-glucopyranoside:

Chemical formula 111

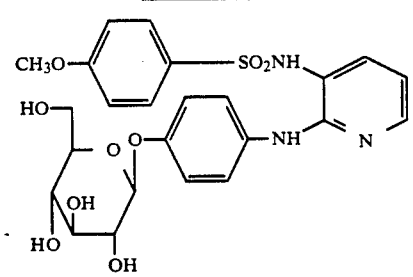

637 mg (0.908 mmol) of the compound produced in Production Example 11 was dissolved in a mixture of 7 ml of 1N sodium hydroxide and 20 ml of ethanol and the solution was refluxed for 3 h. After cooling, 4 ml of 1N hydrochloric acid was added to the solution and the mixture was concentrated. Ethyl acetate and water were added to the concentrate and the ethyl acetate layer thus formed was separated, dried, concentrated and purified by silica gel column chromatography to obtain 270 mg of the title compound.

$^1$H-NMR (DMSO-$d_6$+$D_2O$) δ (ppm): 3.15–3.33 (4H, m), 3.49 (1H, dd, J=5.6, 11.6 Hz), 3.70–3.73 (4H, s+dd), 4.75 (1H, d, J=7.6 Hz), 6.68 (1H, dd, J=4.8, 8.0 Hz), 6.93 (2H, d, J=9.2 Hz), 6.97 (2H, d, J=9.2 Hz), 7.23 (1H, dd, J=2.0, 7.6 Hz), 7.29 (2H, d, J=9.2 Hz), 7.60 (2H, d, J=9.2 Hz), 7.95 (1H, dd, J=2.0, 4.8 Hz)

Example 74

4-[[3-(4-Methoxybenzenesulfonamido)-2-pyridyl-]amino]phenyl β-D-glucopyranoside uronate:

Chemical formula 112

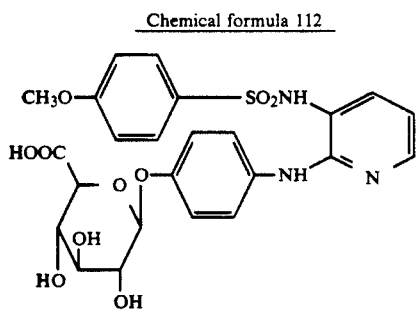

The title compound was produced in the same manner as that of Production Example 11 and Example 73.

¹H-NMR (DMSO-D₆+D₂O) δ (ppm): 3.27 (1H, t, J=8.8 Hz), 3.33 (1H, t, J=8.8 Hz), 3.42 (1H, t, J=8.8 Hz), 3.71 (3H, s), 3.86 (1H, d, J=9.6 Hz), 4.92 (1H, d, J=7.6 (Hz), 6.70 (1H, dd, J=5.2, 7.6 Hz) 6.90 (2H, d, J=8.8 Hz), 6.96 (2H, d, J=8.8 Hz), 7.25 (1H, dd, J=1.6, 7.6 Hz), 7.29 (2H, d, J=8.8 Hz), 7.59 (2H, d, J=8.8 Hz), 7.95 (1H, dd, J=1.6, 5.2 Hz)

Example 75

4-Methoxy-N-[2-[(3,4,5-trimethoxyphenyl)amino]-3-pyridyl]benzenesulfonamide:

Chemical formula 113

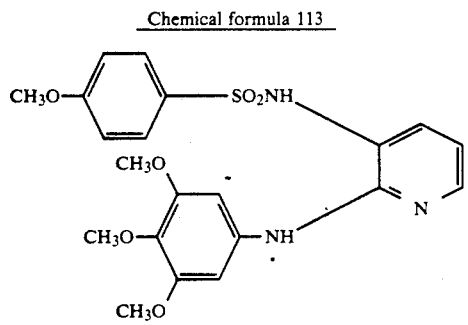

The title compound was produced in the same manner as that of Example 1.

FAB mass spectrometry m/z: 445 (M⁺)

¹H-NMR (DMSO-d₆) δ (ppm): 3.61 (3H, s), 3.71 (3H, s), 3.74 (6H, s), 6.72 (1H, dd, J=4.8, 7.6 Hz), 6.79, 6.80 (2H, s+s), 6.98 (2H, d, J=8.8 Hz), 7.24 (1H, dd, J=1.6, 7.6 Hz), 7.59 (2H, d, J=8.8 Hz), 7.81 (1H, br-s), 8.00 (1H, dd, J=1.6, 4.8 Hz), 9.47 (1H, br-s)

| Elementary analysis for C₂₁H₂₃N₃O₆S: | | | |
|---|---|---|---|
| | C | H | N |
| Calculated: | 56.62 | 5.20 | 9.43 |
| Found: | 56.42 | 5.22 | 9.14 |

Example 76

4-Methoxy-N-[2-[(2-pyridyl)amino]phenyl]benzenesulfonamide:

Chemical formula 114

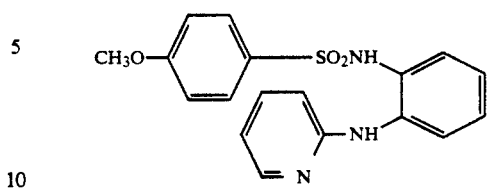

The title compound was produced in the same manner as that of Example 1.

Melting point: 113° to 116° C. (recrystallized from cyclohexane)

FAB mass spectrometry m/z: 356 ([M+H]⁺)

¹H-NMR (DMSO-d₆) δ (ppm): 3.70 (3H, s), 6.53–6.59 (1H, m), 6.70–6.75 (1H, m), 6.71 (2H, d, J=8.8 Hz), 6.95 (1H, dt, J=1.2, 8.0 Hz), 7.11 (1H, dd, J=1.2, 8.0 Hz), 7.14 (1H, dt, J=1.6, 8.0 Hz), 7.41–7.52 (3H, m), 7.61–7.66 (1H, m), 8.05 (1H, dd, J=1.2, 4.8 Hz), 8.06 (1H, br-s), 9.59 (1H, br-s)

| Elementary analysis for C₁₈H₁₇N₃O₃S: | | | |
|---|---|---|---|
| | C | H | N |
| Calculated: | 60.83 | 4.82 | 11.82 |
| Found: | 61.11 | 4.82 | 11.85 |

Example 77

N-(2-Anilino-4-fluorophenyl)-4-methoxybenzene-sulfonamide:

Chemical formula 115

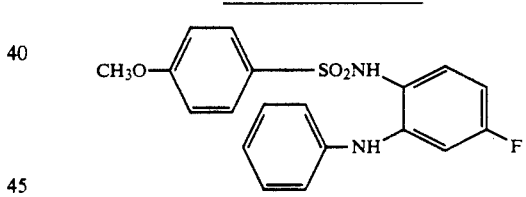

The title compound was produced in the same manner as that of Example 1.

Melting point: 173° to 174° C. (recrystallized from ethanol)

FAB mass spectrometry m/z: 372 (M⁺)

¹H-NMR (DMSO-d₆) δ (ppm): 3.69 (3H, s), 6.57 (1H, dt, J=2.8, 8.8 Hz), 6.73–6.91 (6H, m), 7.00 (1H, dd, J=6.4, 8.8 Hz), 7.19 (2H, t, J=7.6 Hz), 7.37 (1H, br-s), 7.50 (2H, d, J=8.8 Hz), 9.33 (1H, br-s)

| Elementary analysis for C₁₉H₁₇FN₂O₃S: | | | |
|---|---|---|---|
| | C | H | N |
| Calculated: | 61.28 | 4.60 | 7.52 |
| Found: | 61.39 | 4.62 | 7.25 |

Example 78

N-[2-[(4-Chlorophenyl)amino]phenyl]-4-methoxy-benzene-sulfonamide:

Chemical formula 116

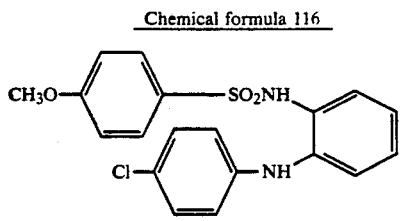

The title compound was produced in the same manner as that of Example 1.

Melting point: 127° to 128° C. (recrystallized from ethanol)

FAB mass spectrometry m/z: 388 (M+)

$^1$H-NMR (DMSO-d$_6$) δ (ppm): 3.69 (3H, s), 6.61 (2H, d, J=8.8 Hz), 6.77 (2H, d, J=9.2 Hz), 6.88–6.94 (1H, m), 7.07–7.14 (4H, m), 7.18 (1H, dd, J=1.2, 8.0 Hz), 7.36 (1H, br-s), 7.47 (2H, d, J=9.2 Hz), 9.28 (1H, br-s)

| Elementary analysis for C$_{19}$H$_{17}$ClN$_2$O$_3$S: | | | |
|---|---|---|---|
| | C | H | N |
| Calculated: | 58.68 | 4.41 | 7.20 |
| Found: | 58.85 | 4.39 | 7.04 |

Example 79

N-[2-[(3-Hydroxyphenyl)amino]phenyl]-4-methoxy-benzene-sulfonamide:

Chemical formula 117

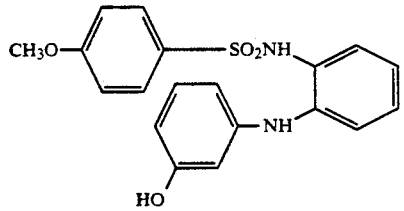

The title compound was produced in the same manner as that of Example 1.

Melting point: 165° to 166° C. (recrystallized from ethanol)

FAB mass spectrometry m/z: 370 (M+)

$^1$H-NMR (DMSO-d$_6$) δ (ppm): 3.71 (3H, s), 6.12–6.17 (2H, m), 6.19–6.24 (1H, m), 6.79–6.86 (3H, m), 6.91 (1H, t, J=8.4 Hz), 7.07 (1H, dt, J=1.2, 8.0 Hz), 7.08 (1H, dd, J=1.2, 8.0 Hz), 7.13 (1H, dd, J=1.2, 8.0 Hz), 7.14 (1H, br-s), 7.52 (2H, d, J=8.8 Hz), 9.16 (1H, s), 9.28 (1H, br-s)

| Elementary analysis for C$_{19}$H$_{18}$N$_2$O$_4$S: | | | |
|---|---|---|---|
| | C | H | N |
| Calculated: | 61.61 | 4.90 | 7.56 |
| Found: | 61.62 | 4.91 | 7.42 |

Example 80

4-Benzyloxy-N-[2-(4-methoxybenzenesulfonamido)-phenyl]-benzamide:

Chemical formula 118

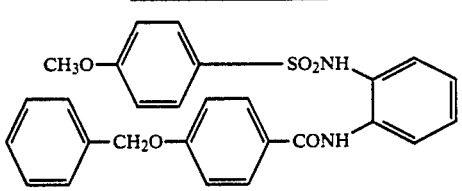

The title compound was produced in the same manner as that of Example 70.

Melting point: 148° to 149 ° C. (recrystallized from ethanol)

FAB mass spectrometry m/z: 489 ([M+H]+)

$^1$H-NMR (DMSO-d$_6$) δ (ppm): 3.74 (3H, s), 5.23 (2H, s), 6.89 (2H, d, J=8.8 Hz), 7.07 (1H, dd, J=2.0, 8.0Hz), 7.10 (1H, dt, J=1.2, 8.0 Hz), 7.17 (2H, d, J=8.8 Hz), 7.23 (1H, dt, J=2.0, 8.0 Hz), 7.33–7.39 (1H, m), 7.42 (2H, t, J32 7.6 Hz), 7.47–7.52 (4H, m), 7.74 (1H, dd, J=1.2, 8.0 Hz), 7.81 (2H, d, J=8.8 Hz), 9.44 (1H, br-s), 9.47 (1H, br-s)

| Elementary analysis for C$_{27}$H$_{24}$N$_2$O$_5$S: | | | |
|---|---|---|---|
| | C | H | N |
| Calculated: | 66.38 | 4.95 | 5.73 |
| Found: | 66.34 | 4.92 | 5.73 |

Example 81

4-Hydroxy-N-[2-(4-methoxybenzenesulfonamido)-phenyl]-benzamide:

Chemical formula 119

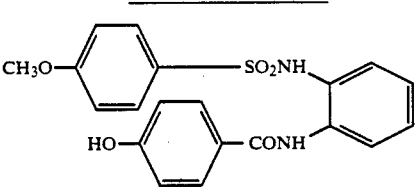

The title compound was produced by catalytically reducing the compound produced in Example 80 in an ordinary manner.

Melting point: 205° to 207 ° C. (recrystallized from ethyl acetate)

FAB mass spectrometry m/z: 399 ([M+H]+)

$^1$H-NMR (DMSO-d$_6$) δ (ppm): 3.76 (3H, s), 6.89 (2H, d, J=8.8 Hz), 6.91 (2H, d, J=8.8 Hz), 7.04 (1H, dd, J=1.6, 8.0 Hz), 7.09 (1H, dt, J=1.6, 8.0 Hz), 7.20–7.25 (1H, m), 7.50 (2H, d, J=8.8 Hz), 7.68–7.76 (3H, m), 9.38 (1H, s), 9.47 (1H, s), 10.20 (1H, s)

| Elementary analysis for C$_{20}$H$_{18}$N$_2$O$_5$S: | | | |
|---|---|---|---|
| | C | H | N |
| Calculated: | 60.29 | 4.55 | 7.03 |
| Found: | 60.38 | 4.58 | 6.75 |

Example 82

4-Fluoro-N-[2-(4-methoxybenzenesulfonamido)-phenyl]benzamide:

Chemical formula 120

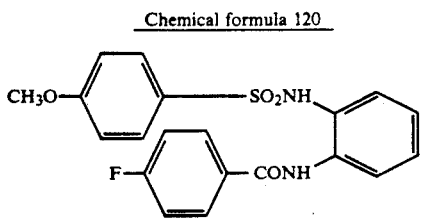

The title compound was produced in the same manner as that of Example 70.

Melting point: 169° to 170° C. (recrystallized from ethanol)

FAB mass spectrometry m/z: 401 ([M+H]+)

$^1$H-NMR (DMSO-d$_6$) δ (ppm): 3.75 (3H, s), 6.90 (2H, d), 7.07–7.16 (2H, m), 7.19–7.26 (1H, m), 7.39 (2H, t, J=8.8 Hz), 7.50 (2H, d, J=8.8 Hz), 7.66–7.73 (1H, m), 7.91 (2H, dd, J=5.6, 8.8 Hz), 9.38 (1H, br-s), 9.54 (1H, br-s)

Elementary analysis for C$_{20}$H$_{17}$FN$_2$O$_4$S:

|  | C | H | N |
|---|---|---|---|
| Calculated: | 59.99 | 4.28 | 7.00 |
| Found: | 60.00 | 4.31 | 6.70 |

Example 83

3-Hydroxy-N-[2-(4-methoxybenzenesulfonamido)-phenyl]benzamide:

Chemical formula 121

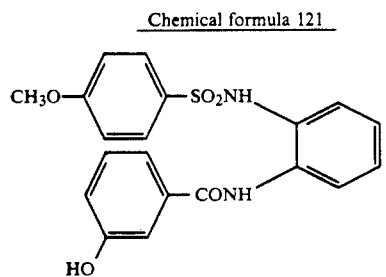

The title compound was produced in the same manner as that of Example 81.

Melting point: 191° to 192° C. (recrystallized from ethanol)

FAB mass spectrometry m/z: 399 ([M+H]+)

$^1$H-NMR (DMSO-d$_6$) δ (ppm): 3.77 (3H, s), 6.92 (2H, d, J=8.8 Hz), 6.99–7.06 (2H, m), 7.09 (1H, dt, J=1.6, 8.0 Hz), 7.20–7.27 (3H, m), 7.34 (1H, t, J=8.0 Hz), 7.51 (2H, d, J=8.8 Hz), 7.75–7.81 (1H, m), 9.46 (1H, s), 9.51 (1H, s), 9.81 (1H, s)

Elementary analysis for C$_{20}$H$_{18}$N$_2$O$_5$S:

|  | C | H | N |
|---|---|---|---|
| Calculated: | 60.29 | 4.55 | 7.03 |
| Found: | 60.41 | 4.55 | 6.71 |

Example 84

N-[2-(4-Methoxybenzenesulfonamido)phenyl]-2-thiophenecarboxamide:

Chemical formula 122

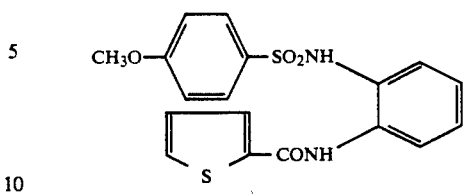

The title compound was produced in the same manner as that of Example 70.

Melting point: 136° to 137° C. (recrystallized from ethanol)

FAB mass spectrometry m/z: 389 ([M+H]+)

$^1$H-NMR (DMSO-d$_6$) δ (ppm): 3.75 (3H, s), 6.85 (2H, d, J=8.8 Hz), 7.05–7.13 (2H, m), 7.17–7.26 (2H, m), 7.49 (2H, d, J=8.8 Hz), 7.60–7.70 (1H, m), 7.77 (1H, dd, J=1.6, 4.0 Hz), 7.87 (1H, dd, J=1.6, 5.2 Hz), 9.50 (2H, br-s)

Elementary analysis for C$_{18}$H$_{16}$N$_2$O$_4$S$_2$:

|  | C | H | N |
|---|---|---|---|
| Calculated: | 55.65 | 4.15 | 7.21 |
| Found: | 55.80 | 4.27 | 7.24 |

Example 85

N-[2-(4-Methoxybenzenesulfonamido)phenyl]-2-furancarboxamide:

Chemical formula 123

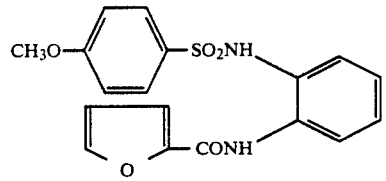

The title compound was produced in the same manner as that of Example 70.

Melting point: 158° to 159° C. (recrystallized from ethanol)

FAB mass spectrometry m/z: 373 ([M+H]+)

$^1$H-NMR (DMSO-d$_6$) δ (ppm): 3.76 (3H, s), 6.73 (1H, dd, J=1.6, 3.6 Hz), 6.91 (2H, d, J=8.8 Hz), 6.98 (1H, dd, J=1.6, 8.0 Hz), 7.08 (1H, dt, J=1.6, 8.0 Hz), 7.21 (1H, dd, J=0.8, 3.6 Hz), 7.24 (1H, dt, J=1.6, 8.0 Hz), 7.53 (2H, d, J=8.8 Hz), 7.84 (1H, dd, J=1.6, 8.0 Hz), 7.99 (1H, dd, J=0.8, 1.6 Hz), 9.42 (1H, br-s), 9.62 (1H, br-s)

Elementary analysis for C$_{18}$H$_{16}$N$_2$O$_5$S:

|  | C | H | N |
|---|---|---|---|
| Calculated: | 58.05 | 4.33 | 7.52 |
| Found: | 58.08 | 4.39 | 7.44 |

Example 86

N-[2-(4-Methoxybenzenesulfonamido)phenyl]-2-pyridinecarboxamide:

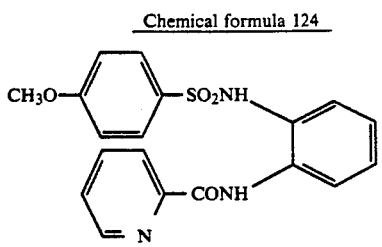

Chemical formula 124

The title compound was produced in the same manner as that of Example 70.

Melting point: 174° to 175° C. (recrystallized from ethanol)

FAB mass spectrometry m/z: 384 ([M+H]+)

$^1$H-NMR (DMSO-d$_6$) δ (ppm): 3.75 (3H, s), 6.82 (1H, dd, J=1.6, 8.0 Hz), 6.92 (2H, d, J=8.8 Hz), 7.03 (1H, dt, J=1.6, 8.0 Hz), 7.30 (1H, dt, J=1.6, 8.0 Hz), 7.57 (2H, d, J=8.8 Hz), 7.70 (1H, td, J=1.6, 4.8, 7.6 Hz), 8.08 (1H, dt, J=1.6, 7.6 Hz), 8.12-8.17 (1H, m), 8.24 (1H, dd, J=1.6, 7.6 Hz), 8.77 (1H, dd, J=1.6, 4.8 Hz), 9.73 (1H, br-s), 10.67 (1H, br-s)

| Elementary analysis for C$_{19}$H$_{17}$N$_3$O$_4$S: | | | |
|---|---|---|---|
| | C | H | N |
| Calculated: | 59.52 | 4.47 | 10.96 |
| Found: | 59.73 | 4.54 | 10.92 |

Example 87

N-[2-(4-Methoxybenzenesulfonamido)phenyl]-nicotinamide:

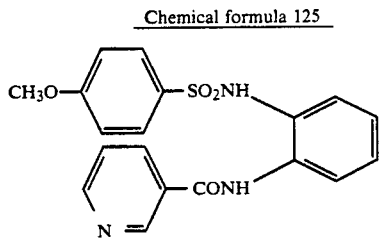

Chemical formula 125

The title compound was produced in the same manner as that of Example 70.

Melting point: 179° to 180° C. (recrystallized from ethanol)

FAB mass spectrometry m/z: 384 ([M+H]+)

$^1$H-NMR (DMSO-d$_6$) δ (ppm): 3.74 (3H, s), 6.89 (2H, d, J=8.8 Hz), 7.12-7.19 (2H, m), 7.19-7.27 (1H, m), 7.51 (2H, d, J=8.8 Hz), 7.59 (1H, dd, J=4.8, 8.0 Hz), 7.63-7.71 (1H, m), 8.17 (1H, dd, J=1.2, 8.0 Hz), 8.79 (1H, dd, J=1.2, 4.8 Hz), 8.99 (1H, d, J=1.2 Hz), 9.49 (1H, br-s), 9.68 (1H, br-s)

| Elementary analysis for C$_{19}$H$_{17}$N$_3$O$_4$S: | | | |
|---|---|---|---|
| | C | H | N |
| Calculated: | 59.52 | 4.47 | 10.96 |
| Found: | 59.61 | 4.57 | 10.84 |

Example 88

N-[2-(4-Methoxybenzenesulfonamido)phenyl]isonicotinamide:

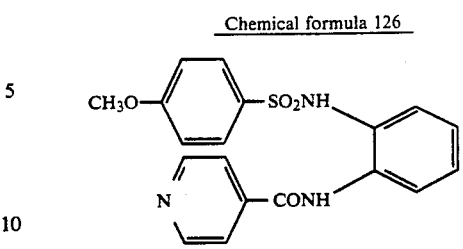

Chemical formula 126

The title compound was produced in the same manner as that of Example 70.

Melting point: 162° to 163° C. (recrystallized from ethanol)

FAB mass spectrometry m/z: 384 ([M+H]+)

$^1$H-NMR (DMSO-d$_6$) δ (ppm): 3.75 (3H, s), 6.90 (2H, d, J=8.8 Hz), 7.11-7.27 (3H, m), 7.53 (2H, d, J=8.8 Hz), 7.64-7.71 (1H, m), 7.75 (2H, d, J=4.8 Hz), 8.81 (2H, d, J=4.8 Hz), 9.52 (1H, br-s), 9.73 (1H, br-s)

| Elementary analysis for C$_{19}$H$_{17}$N$_3$O$_4$S: | | | |
|---|---|---|---|
| | C | H | N |
| Calculated: | 59.52 | 4.47 | 10.96 |
| Found: | 59.59 | 4.52 | 10.96 |

EXAMPLE 89

4-Fluoro-N-[2-(4-methoxybenzenesulfonamido)-6-methylphenyl]benzamide:

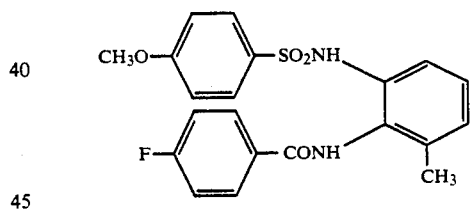

Chemical formula 127

The title compound was produced in the same manner as that of Example 70.

Melting point: 204° to 206° C. (recrystallized from ethanol)

FAB mass spectrometry m/z: 415 ([M+H]+)

$^1$H-NMR (DMSO-d$_6$) δ (ppm): 2.10 (3H, s), 3.80 (3H, s), 6.97 (2H, d, J=8.8 Hz), 7.00-7.12 (3H, m), 7.37 (2H, t, J=8.8 Hz), 7.65 (2H, d, J=8.8 Hz), 8.03 (2H, dd, J=5.6, 8.8 Hz), 9.46 (1H, br-s), 9.48 (1H, br-s)

| Elementary analysis for C$_{21}$H$_{19}$FN$_2$O$_4$S: | | | |
|---|---|---|---|
| | C | H | N |
| Calculated: | 60.86 | 4.62 | 6.76 |
| Found: | 60.74 | 4.56 | 6.65 |

EXAMPLE 90

N-[2-(4-Methoxybenzenesulfonamido)-6-methylphenyl]-nicotinamide:

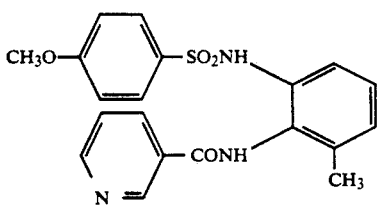

Chemical formula 128

The title compound was produced in the same manner as that of Example 70.

Melting point: 207° to 209° C. (recrystallized from ethanol)

FAB mass spectrometry m/z: 398 ([M+H]+)

$^1$H-NMR (DMSO-d$_6$) δ (ppm): 2.11 (3H, s), 3.79 (3H, s), 6.98 (2H, d, J=8.8 Hz), 7.02 (1H, dd, J=1.6, 7.6 Hz), 7.05–7.14 (2H, m), 7.58 (1H, dd, J=4.8, 8.0 Hz), 7.66 (2H, d, J=8.8 Hz), 8.29 (1H, dt, J=1.6, 8.0 Hz), 8.77 (1H, dd, J=1.6, 4.8 Hz), 9.13 (1H, d, J=1.6 Hz), 9.53 (1H, br), 9.64 (1H, br-s)

| Elementary analysis for C$_{20}$H$_{19}$N$_3$O$_4$S: | | | |
|---|---|---|---|
| | C | H | N |
| Calculated: | 60.44 | 4.82 | 10.57 |
| Found: | 60.55 | 4.90 | 10.53 |

EXAMPLE 91

N-[2-(4-Methoxybenzenesulfonamido)-6-methylphenyl]-isonicotinamide:

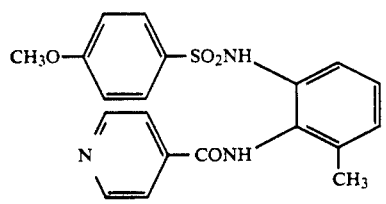

Chemical formula 129

The title compound was produced in the same manner as that of Example 70.

Melting point: 213° to 217° C. (recrystallized from ethanol)

FAB mass spectrometry m/z: 398 ([M+H]+)

$^1$H-NMR (DMSO-d$_6$) δ (ppm): 2.10 (3H, s), 3.80 (3H, s), 6.99 (2H, d, J=8.8 Hz), 7.02 (1H, dd, J=1.6, 7.6 Hz), 7.04–7.14 (2H, m), 7.67 (2H, d, J=8.8 Hz), 7.87 (2H, dd, J=1.6, 8.4 Hz), 8.80 (2H, dd, J=1.6, 8.4 Hz), 9.56 (1H, br-s), 9.73 (1H, br-s)

| Elementary analysis for C$_{20}$H$_{19}$N$_3$O$_4$S: | | | |
|---|---|---|---|
| | C | H | N |
| Calculated: | 60.44 | 4.82 | 10.57 |
| Found: | 60.60 | 4.85 | 10.53 |

EXAMPLE 92

N-[2-(4-Methoxybenzenesulfonamido)-6-methylphenyl]-2-pyridinecarboxamide:

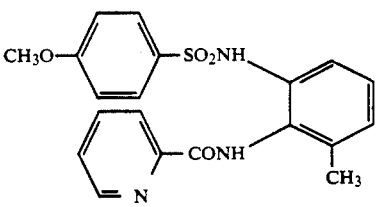

Chemical formula 130

The title compound was produced in the same manner as that of Example 70.

Melting point: 180° to 182° C. (recrystallized from ethanol)

FAB mass spectrometry m/z: 398 ([M+H]+)

$^1$H-NMR (DMSO-d$_6$) δ (ppm): 2.12 (3H, s), 3.78 (3H, s), 6.90 (2H, d, J=8.8 Hz), 6.93 (1H, t, J=4.8 Hz), 7.11 (2H, d, J=4.8 Hz), 7.54 (2H, d, J=8.8 Hz), 7.65–7.72 (1H, m), 8.03–8.08 (2H, m), 8.75 (1H, dd, J=1.2, 5.2 Hz), 9.53 (1H, br-s), 10.11 (1H, br-s)

| Elementary analysis for C$_{20}$H$_{19}$N$_3$O$_4$S: | | | |
|---|---|---|---|
| | C | H | N |
| Calculated: | 60.44 | 4.82 | 10.57 |
| Found: | 60.43 | 4.92 | 10.45 |

EXAMPLE 93

N-[2-(4-Methoxybenzenesulfonamido)phenyl]-2-nitrobenzamide:

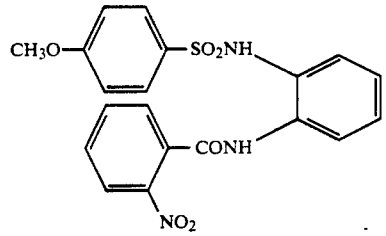

Chemical formula 131

The title compound was produced in the same manner as that of Example 70.

Melting point: 168° to 170° C. (recrystallized from ethanol)

FAB mass spectrometry m/z: 428 ([M+H]+)

$^1$H-NMR (DMSO-d$_6$) δ (ppm): 3.80 (3H, s), 7.05 (2H, d, J=8.8 Hz), 7.07–7.16 (2H, m), 7.19–7.26 (1H, m), 7.62 (2H, d, J=8.8 Hz), 7.66 (1H, d, J=8.0 Hz), 7.73 (1H, d, J=8.0 Hz), 7.79 (1H, t, J=8.0 Hz), 7.92 (1H, t, J=8.0 Hz), 8.16 (1H, d, J=8.0 Hz), 9.23 (1H, br-s), 9.93 (1H, br-s)

| Elementary analysis for C$_{20}$H$_{17}$N$_3$O$_6$S: | | | |
|---|---|---|---|
| | C | H | N |
| Calculated: | 56.20 | 4.01 | 9.83 |
| Found: | 56.21 | 4.05 | 9.77 |

EXAMPLE 94

2-Chloro-4-fluoro-N-[2-(4-methoxybenzenesulfonamido)phenyl]benzamide:

Chemical formula 132

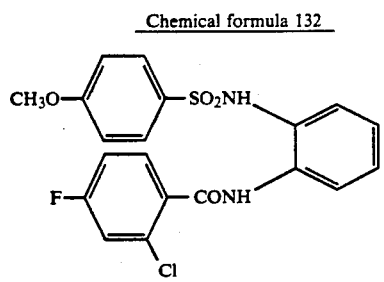

The title compound was produced in the same manner as that of Example 70.

Melting point: 160° to 162° C. (recrystallized from ethanol)

FAB mass spectrometry m/z: 435 ([M+H]+)

$^1$H-NMR (DMSO-d$_6$) δ (ppm): 3.81 (3H, s), 6.97–7.18 (4H, m), 7.19–7.28 (1H, m), 7.34–7.44 (1H, m), 7.51–7.64 (4H, m), 6.74–7.82 (1H, m), 9.33 (1H, br-s), 9.69 (1H, s)

| Elementary analysis for $C_{20}H_{16}ClN_2O_4S$: | | |
|---|---|---|
| C | H | N |
| Calculated: 55.24 | 3.71 | 6.44 |
| Found: 55.42 | 3.90 | 6.20 |

Example 95

N-[2-(4-Methoxybenzenesulfonamido)phenyl]-2-methylbenzamide:

Chemical formula 133

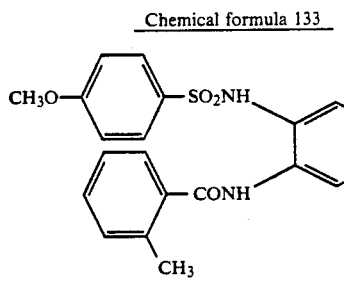

The title compound was produced in the same manner as that of Example 70.

Melting point: 129° to 130° C. (recrystallized from ethanol)

FAB mass spectrometry m/z: 397 ([M+H]+)

$^1$H-NMR (DMSO-d$_6$) δ (ppm): 2.38 (3H, s), 3.81 (3H, s), 7.03 (2H, d, J=8.8 Hz), 7.07 (1H, dd, J=2.0, 8.0 Hz), 7.10 (1H, dt, J=1.2, 8.0 Hz), 7.19–7.27 (1H, m), 7.27–7.39 (3H, m), 7.42 (1H, dt, J=2.0, 7.2 Hz), 7.56 (2H, d, J=8.8 Hz), 7.80–7.87 (1H, m), 9.40 (1H, br-s), 9.46 (1H, br-s)

| Elementary analysis for $C_{21}H_{20}N_2O_4S$: | | |
|---|---|---|
| C | H | N |
| Calculated: 63.62 | 5.09 | 7.07 |
| Found: 63.64 | 5.09 | 7.03 |

Example 96

2-Chloro-N-[2-(4-methoxybenzenesulfonamido)-phenyl]nicotinamide:

Chemical formula 134

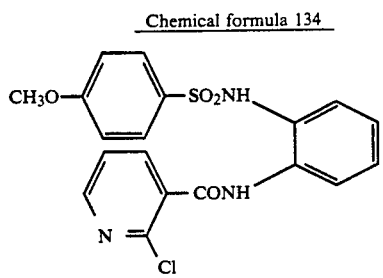

The title compound was produced in the same manner as that of Example 70.

Melting point: 133° to 135° C. (recrystallized from ethanol)

FAB mass spectrometry m/z: 418 ([M+H]+)

$^1$H-NMR (DMSO-d$_6$) δ (ppm): 3.81 (3H, s), 7.04 (2H, d, J=8.8 Hz), 7.07–7.15 (2H, m), 7.18–7.22 (1H, m), 7.60 (2H, d, J=8.8 Hz), 7.61 (1H, dd, J=4.8, 7.6 Hz), 7.78 (1H, d, J=7.6 Hz), 7.98 (1H, dd, J=2.0, 7.6 Hz), 8.56 (1H, dd, J=2.0, 4.8 Hz), 9.29 (1H, br-s), 9.87 (1H, s)

| Elementary analysis for $C_{19}H_{16}ClN_3O_4S$: | | |
|---|---|---|
| C | H | N |
| Calculated: 54.61 | 3.86 | 10.06 |
| Found: 54.71 | 3.87 | 9.90 |

Example 97

4-Fluoro-N-[2-(4-methoxybenzenesulfonamido)-phenyl]benzothioamide:

Chemical formula 135

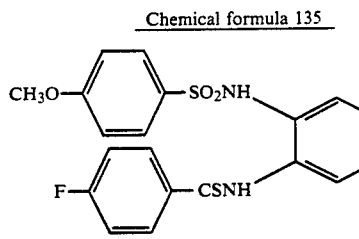

A mixture of 549 mg (1.371 mmol) of the compound produced in Example 82, 333 mg (0.823 mmol) of Lawesson reagent and 10 ml of toluene was heated at 100° C. After the concentration, the residue was purified by silica gel column chromatography to obtain 506 mg of the title compound.

Melting point: 155° to 156° C. (recrystallized from n-butanol)

FAB mass spectrometry m/z: 417 ([M+H]+)

$^1$H-NMR (DMSO-d$_6$) δ (ppm): 3.80 (3H, s), 7.02 (2H, d, J=8.8 Hz), 7.10–7.25, (3H, m), 7.33 (2H, t, J=8.8 Hz), 7.47–7.58 (1H, m), 7.63 (2H, d, J=8.8 Hz), 7.98 (2H, dd, J=5.6, 8.8 Hz), 9.45 (1H, br), 11.13 (1H, br)

| Elementary analysis for $C_{20}H_{17}FN_2O_3S_2$: | | |
|---|---|---|
| C | H | N |
| Calculated: 57.68 | 4.11 | 6.73 |

| Elementary analysis for $C_{20}H_{17}FN_2O_3S_2$: | | | |
|---|---|---|---|
| | C | H | N |
| Found: | 57.63 | 4.12 | 6.58 |

Example 98

N-[5-fluoro-2-(4-methoxybenzenesulfonamido)-phenyl]benzamide:

Chemical formula 136

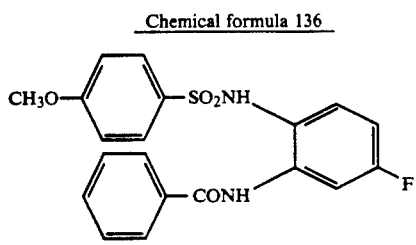

The title compound was produced in the same manner as that of Example 70.

Melting point: 153° to 154° C. (recrystallized from ethanol)

FAB mass spectrometry m/z: 401 ([M+H]$^+$)

$^1$H-NMR (DMSO-d$_6$) δ (ppm): 3.75 (3H, s), 6.88 (2H, d, J=8.8 Hz), 6.94 (1H, dt, J=3.2, 8.8 Hz), 7.00 (1H, dd, J=6.0, 8.8 Hz), 7.47 (2H, d, J=8.8 Hz), 7.55 (2H, t, J=7.6 Hz), 7.59–7.66 (1H, m), 7.74–7.83 (3H, m), 9.45 (1H, br-s), 9.55 (1H, br-s)

| Elementary analysis for $C_{20}H_{17}FN_2O_4S$: | | | |
|---|---|---|---|
| | C | H | N |
| Calculated: | 59.55 | 4.28 | 7.00 |
| Found: | 59.97 | 4.32 | 6.79 |

Example 99

4-Fluoro-N-[2-(4-nitrobenzenesulfonamido)phenyl]-benzamide:

Chemical formula 137

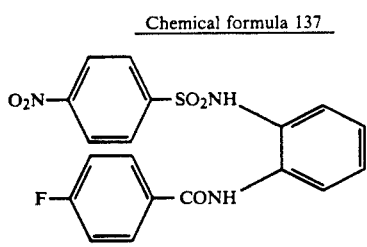

The title compound was produced from the compound produced in Production Example 13 in the same manner as that of Example 70.

Melting point: 265° to 266° C. (recrystallized from ethyl acetate)

FAB mass spectrometry m/z: 416 ([M+H]$^+$) 7.21 (1H, dt, J=1.6, 8.0 Hz), 7.25 (1H, dd, J=2.0, 8.0 Hz), 7.30 (1H, dt, J=2.0, 8.0 Hz), 7.35 (2H, t, J=8.8 Hz), 7.55–7.60 (1H, m), 7.76 (2H, d, J=8.8 Hz), 7.83 (2H, dd, J=5.6, 8.8 Hz), 8.22 (2H, d, J=8.8 Hz), 9.42 (1H, s), 9.89 (1H, s)

| Elementary analysis for $C_{19}H_{14}FN_3O_5S$: | | | |
|---|---|---|---|
| | C | H | N |
| Calculated: | 54.94 | 3.40 | 10.12 |
| Found: | 54.90 | 3.36 | 9.93 |

Example 100

2-Chloro-6-methyl-N-[2-(4-methoxybenzenesulfonamido)phenyl]isonicotinamide:

Chemical formula 138

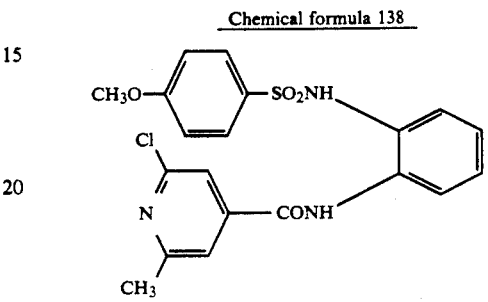

The title compound was produced in the same manner as that of Example 70.

Melting point: 150° to 151° C. (recrystallized from ethanol)

FAB mass spectrometry m/z: 432 ([M+H]$^+$)

$^1$H-NMR (DMSO-d$_6$) δ (ppm): 2.58 (3H, s), 3.76 (3H, s), 6.90 (2H, d, J=8.8 Hz), 7.15–7.26 (3H, m), 7.52 (2H, d, J=8.8 Hz), 7.54–7.63 (3H, m), 9.44 (1H, br-s), 9.73 (1H, br-s)

| Elementary analysis for $C_{20}H_{18}ClN_3O_4S$: | | | |
|---|---|---|---|
| | C | H | N |
| Calculated: | 55.62 | 4.20 | 9.73 |
| Found: | 55.80 | 4.26 | 9.75 |

Example 101

N-[2-(4-Methoxybenzenesulfonamido)phenyl]acetamide:

Chemical formula 139

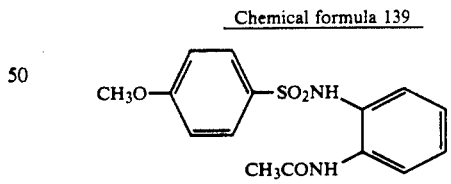

The title compound was produced in the same manner as that of Example 70.

Melting point: 160° to 161° C. (recrystallized from ethanol)

FAB mass spectrometry m/z: 321 ([M+H]$^+$)

$^1$H-NMR (DMSO-d$_6$) δ (ppm): 1.96 (3H, s), 3.80 (3H, s), 6.99–7.17 (5H, m), 7.48 (1H, d, J=8.0 Hz), 7.53 (2H, d, J=8.8 Hz), 9.23 (2H, br-s)

| Elementary analysis for $C_{15}H_{16}N_2O_4S$: | | | |
|---|---|---|---|
| | C | H | N |
| Calculated: | 56.24 | 5.03 | 8.75 |

Example 102

N-[2-(4-Methoxybenzenesulfonamido)phenyl]formamide:

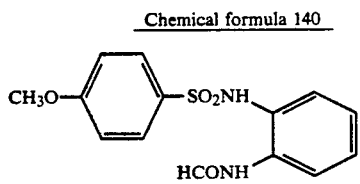

Chemical formula 140

The title compound was produced in the same manner as that of Example 70.

Melting point: 143° to 144° C. (recrystallized from ethanol)

FAB mass spectrometry m/z: 307 ([M+H]+)

| Elementary analysis for $C_{14}H_{14}N_2O_4S$: | | | |
|---|---|---|---|
| | C | H | N |
| Calculated: | 54.89 | 4.61 | 9.14 |
| Found: | 55.05 | 4.65 | 9.09 |

Example 103

N-[2-[(Ethoxycarbonyl)amino]phenyl]-4-methoxybenzenesulfonamide:

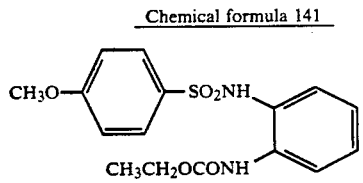

Chemical formula 141

The title compound was produced in the same manner as that of Example 70.

Melting point: 118° to 119° C. (recrystallized from ethanol)

FAB mass spectrometry m/z: 351 ([M+H]+)

$^1$H-NMR (DMSO-d$_6$) δ (ppm): 1.22 (3H, t, J=7.2 Hz), 3.79 (3H, s), 4.03 (2H, q, J=7.2 Hz), 6.98–7.03 (4H, m), 7.17 (1H, t, J=8.0 Hz), 7.52 (2H, d, J=8.8 Hz), 7.57 (1H, d, J=8.0 Hz), 8.43 (1H, s), 9.35 (1H, s)

| Elementary analysis for $C_{16}H_{18}N_2O_5S$: | | | |
|---|---|---|---|
| | C | H | N |
| Calculated: | 54.84 | 5.18 | 7.99 |
| Found: | 54.78 | 5.19 | 7.86 |

Example 104

N-[2-[(Ethylaminocarbonyl)amino]phenyl]-4-methoxybenzenesulfonamide:

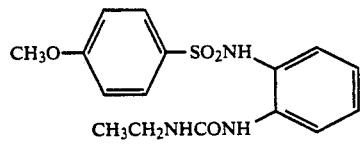

Chemical formula 142

The title compound was produced by reacting the compound produced in Production Example 12 with ethyl isocyanate and treating the product in an ordinary manner.

Melting point: 152° to 154° C. (recrystallized from ethanol)

FAB mass spectrometry m/z: 350 ([M+H]+)

$^1$H-NMR (DMSO-d$_6$) δ (ppm): 1.08 (3H, t, J=7.2 Hz), 3.10 (2H, dq, J=5.6, 7.2 Hz), 3.82 (3H, s), 6.61 (1H, dd, J=1.6, 8.0 Hz), 6.77 (1H, dt, J=1.2, 8.0 Hz), 6.89 (1H, t, J=5.6 Hz), 7.04 (2H, d, J=8.8 Hz), 7.05–7.12 (1H, m), 7.57 (2H, d, J=8.8 Hz), 7.78 (1H, dd, J=1.2, 8.4 Hz), 7.94 (1H, s), 9.41 (1H, s)

| Elementary analysis for $C_{16}H_{19}N_3O_4S$: | | | |
|---|---|---|---|
| | C | H | N |
| Calculated: | 55.00 | 5.48 | 12.03 |
| Found: | 55.08 | 5.47 | 11.88 |

Example 105

N-[3-(4-Methoxybenzenesulfonamido)-2-pyridyl]-2-methylbenzamide:

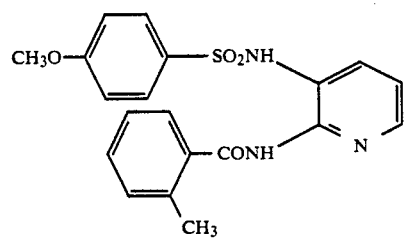

Chemical formula 143

The title compound was produced in the same manner as that of Example 70.

Melting point: 160° to 162° C. (recrystallized from ethanol)

FAB mass spectrometry m/z: 398 ([M+H]+)

$^1$H-NMR (DMSO-d$_6$) δ (ppm): 2.37 (3H, s), 3.81 (3H, s), 7.05 (2H, d, J=8.8 Hz), 7.22–7.33 (4H, m), 7.36–7.43 (1H, m), 7.59 (2H, d, J=8.8 Hz), 7.71 (1H, dd, J=1.6, 8.0 Hz), 8.25 (1H, dd, J=1.6, 4.8 Hz), 9.24 (1H, br-s), 10.47 (1H, br-s)

| Elementary analysis for $C_{20}H_{19}N_3O_4S$: | | | |
|---|---|---|---|
| | C | H | N |
| Calculated: | 60.44 | 4.82 | 10.57 |
| Found: | 60.53 | 4.84 | 10.67 |

Example 106

N-[2-(4-Aminobenzenesulfonamido)phenyl]-4-fluorobenzamide:

---

Continued Elementary analysis for $C_{15}H_{16}N_2O_4S$:

| | C | H | N |
|---|---|---|---|
| Found: | 56.26 | 5.03 | 8.72 |

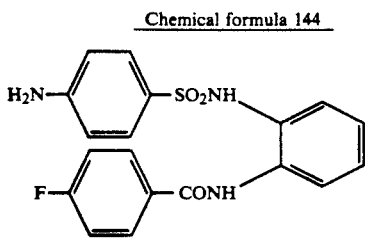

Chemical formula 144

The title compound was produced by reducing the compound produced in Example 99 with zinc/hydrochloric acid.

Melting point: 203° to 205° C. (recrystallized from ethanol)

FAB mass spectrometry m/z: 386 ([M+H]+)

$^1$H-NMR (DMSO-d$_6$) δ (ppm): 5.98 (2H, br-s), 6.45 (2H, d, J=8.8 Hz), 7.05 (1H, dd, J=1.6, 8.0 Hz), 7.09 (1H, dt, J=1.6, 8.0 Hz), 7.20 (1H, dt, J=1.6, 8.0 Hz), 7.23 (2H, d, J=8.8 Hz), 7.39 (2H, t, J=8.8 Hz), 7.74–7.80 (1H, m), 7.93 (2H, dd, J=5.6, 8.8 Hz), 9.20 (1H, br-s), 9.63 (1H, br-s)

| Elementary analysis for $C_{19}H_{16}FN_3O_3S$: | | | |
|---|---|---|---|
| | C | H | N |
| Calculated: | 59.21 | 4.18 | 10.90 |
| Found: | 59.36 | 4.21 | 10.80 |

Example 107

N-[2-(4-Chlorobenzenesulfonamido)phenyl]benzamide

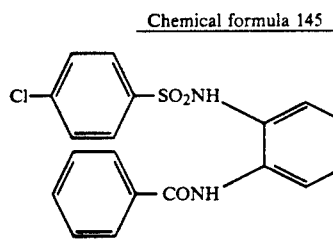

Chemical formula 145

The title compound was produced in the same manner as that of Example 70.

Melting point: 191° to 192° C. (recrystallized from ethanol)

FAB mass spectrometry m/z: 387 ([M+H]+)

$^1$H-NMR (DMSO-d$_6$) δ (ppm): 7.13–7.20 (2H, m), 7.24–7.30 (1H, m), 7.42 (2H, d, J=8.8 Hz), 7.54 (2H, d, J=8.8 Hz), 7.55 (2H, t, J=8.8 Hz), 7.60–7.66 (1H, m), 7.68–7.72 (1H, m), 7.78–7.83 (2H, m), 9.52 (1H, s), 9.71 (1H, s)

| Elementary analysis for $C_{19}H_{15}ClN_2O_3S$: | | | |
|---|---|---|---|
| | C | H | N |
| Calculated: | 58.99 | 3.91 | 7.24 |
| Found: | 59.25 | 4.02 | 7.29 |

Example 108

N-[2-(3,4-Dimethoxybenzenesulfonamido)phenyl]-benzamide:

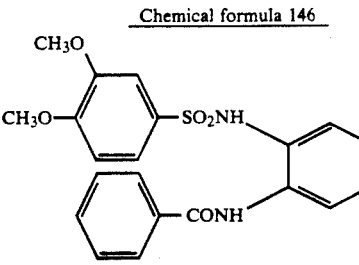

Chemical formula 146

The title compound was produced in the same manner as that of Example 70.

Melting point: 183° to 184° C. (recrystallized from ethanol)

FAB mass spectrometry m/z: 413 ([M+H]+)

$^1$H-NMR (DMSO-d$_6$) δ (ppm): 3.53 (3H, s), 3.75 (3H, s), 6.90 (1H, d, J=8.4 Hz), 6.95 (1H, d, J=2.0 Hz), 7.13 (1H, dd, J=2.0, 8.4 Hz), 7.13–7.18 (2H, m), 7.23–7.29 (1H, m), 7.54 (2H, t, J=7.6 Hz), 7.59–7.65 (1H, m), 7.71–7.76 (1H, m), 7.76–7.82 (2H, m), 9.43 (1H, br-s), 9.53 (1H, br-s)

| Elementary analysis for $C_{21}H_{20}N_2O_5S$: | | | |
|---|---|---|---|
| | C | H | N |
| Calculated: | 61.15 | 4.89 | 6.79 |
| Found: | 61.16 | 4.90 | 6.82 |

Example 109

N-[2-(4-Methoxybenzenesulfonamido)phenyl]benzamide:

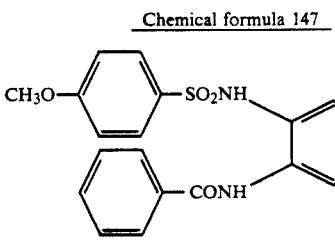

Chemical formula 147

The title compound was produced in the same manner as that of Example 70.

Melting point: 167° to 168° C. (recrystallized from ethanol)

FAB mass spectrometry m/z: 383 ([M+H]+)

$^1$H-NMR (DMSO-d$_6$) δ (ppm): 3.75 (3H, s), 6.91 (2H, d, J=8.8 Hz), 7.08 (1H, dd, J=1.6, 8.0 Hz), 7.12 (1H, dt, J=1.6, 8.0 Hz), 7.24 (1H, dt, J=1.6, 8.0 Hz), 7.51 (2H, d, J=8.8 Hz), 7.52–7.59 (2H, m), 7.60–7.66 (1H, m), 7.76 (1H, dd, J=1.6, 8.0 Hz), 7.81–7.86 (2H, m), 9.50 (1H, br-s), 9.55 (1H, br-s)

| Elementary analysis for $C_{20}H_{18}N_2O_4S$: | | | |
|---|---|---|---|
| | C | H | N |
| Calculated: | 62.81 | 4.74 | 7.33 |
| Found: | 63.06 | 4.77 | 7.32 |

Example 110

4-ethoxy-N-[2-((4-hydroxyphenyl)amino)-3-pyridyl]-benzenesulfoneamide was prepared.

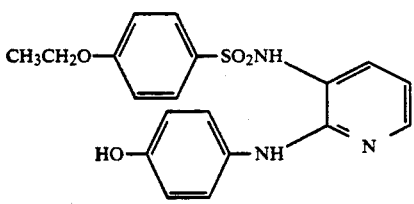

melting point: 194°–195° C. (recrystallized from ethanol)

FAB mass analysis m/z: 386 ([M+H]+)

| Elementary analysis as $C_{19}H_{19}N_3O_3S$: | | | |
|---|---|---|---|
| | C | H | N |
| Calculated: | 59.21 | 4.97 | 10.90 |
| Found: | 59.12 | 4.93 | 10.66 |

$^1$H-NMR (DMSO-d$_6$) δ (ppm): 1.27 (3H, t, J=7.2 Hz), 3.98 (2H, g, J=7.2 Hz), 6.59 (1H, dd, J=4.8, 7.6 Hz), 6.61 (2H, d, J=8.8 Hz), 6.95 (2H, d, J=9.2 Hz), 7.12 (2H, d, J=8.8 Hz), 7.17 (1H, dd, J=1.6, 7.6 Hz), 7.55 (1H, br-s), 7.56 (2H, d, J=9.2 Hz), 7.87 (1H, dd, J=1.6, 4.8 Hz), 8.97 (1H, s), 9.41 (1H, br-s)

We claim:

1. Sulfonamide derivatives of general formula (1) or pharmacologically acceptable salts thereof:

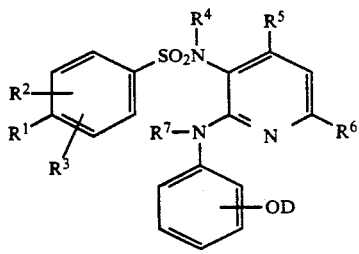

wherein:

R$^1$ represents a hydrogen atom, halogen atom, lower alkyl group, lower alkoxy group, hydroxyl group, nitro group, phenoxy group, cyano group, acetyl group or amino group, R$^2$ and R$^3$ may be the same or different from each other and each represent a hydrogen atom, halogen atom, lower alkyl group or lower alkoxy group, R$^4$ and R$^7$ may be the same or different from each other and each represent a hydrogen atom or lower alkyl group, R$^5$ and R$^6$ may be the same or different from each other and each represents a hydrogen atom, halogen atom, lower alkoxy group, amino group or an amino group substituted with a lower alkyl or a phenyl group, and D represents H or NO.

2. Sulfonamide derivatives or pharmacologically acceptable salts of them according to claim 1, wherein OD is a hydroxyl group or a protected hydroxyl group.

3. Sulfonamide derivatives or pharmacologically acceptable salts thereof according to claim 1, wherein R$^1$ represents a lower alkoxy group.

4. Sulfonamide derivatives or pharmacologically acceptable salts of them according to claim 3, wherein OD is a hydroxyl group or a protected hydroxyl group.

5. Sulfonamide derivatives or pharmacologically acceptable salts thereof according to claim 1, wherein the compound is selected from among the following sulfonamide derivatives:

4-methoxy-N-[2-[(4-methoxyphenyl)amino]-3-pyridyl]benzenesulfonamide or

N-[2-[(4-hydroxyphenyl)amino]-3-pyridyl]-4-methoxybenzenesulfonamide.

6. A pharmacological composition which comprises a pharmacologically effective amount of the derivative as defined in claim 1 and a pharmacologically acceptable carrier.

7. Sulfonamide derivatives of general formula (1) or pharmacological acceptable salts thereof

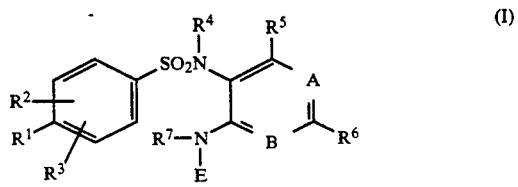

wherein:

R$^1$ represents a hydrogen atom, halogen atom, lower alkyl group, lower alkoxy group, hydroxyl group, nitro group, phenoxy group, cyano group, acetyl group, or amino group, R$^2$ and R$^3$ may be the same or different from each other and each represent a hydrogen atom, halogen atom, lower alkyl group or lower alkoxy group, R$^4$ and R$^7$ may be the same or different from each other and each represent a hydrogen atom or lower alkyl group, R$^5$ and R$^6$ may be the same or different from each other and each represents a hydrogen atom, halogen atom, lower alkoxy group, amino group or an amino group substituted with a lower alkyl or a phenyl group, A is =CH—, B is =N— and E is phenyl optionally substituted by —OD, D representing H, NO, PO(OH)$_2$ or a lower alkyl group.

8. Sulfonamide derivatives or pharmacologically acceptable salts thereof according to claim 7, wherein the compound is selected from among the following sulfonamide derivatives:

(1) N-(2-anilino-3-pyridyl)-p-toluenesulfonamide, (2) N-(2-anilino-3-pyridyl)-4-ethylbenzenesulfonamide, (3) N-(2-anilino-3-pyridyl)-4-methoxybenzenesulfonamide, and (4) 4-[[3-(4-methoxybenzenesulfonamide)-2-pyridyl]amino]-phenyl dihydrogenphosphate.

9. Sulfonamide derivatives of the general formula (1) or pharmacologically acceptable salts thereof:

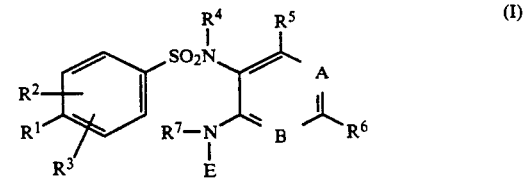

wherein:

R$^1$ represents a hydrogen atom, halogen atom, lower alkyl group, lower alkoxy group, hydroxyl group, nitro group, phenoxy group, cyano group, acetyl group, or amino group, R$^2$ and R$^3$ may be the same or different from each other and each represent a hydrogen atom, halogen atom, lower alkyl group or lower alkoxy group, $R^4$ and $R^7$ may be the same or different from each other and each represents a hydrogen atom or a lower alkyl group, $R^5$ and $R^6$ may be the same or different from each other and each represents a hydrogen atom, halogen atom, lower alkoxy group, amino group or an amino group substituted with a lower alkyl or a phenyl group, A is =CH—, B is =N— and E is a phenyl group or a phenyl group having from 1 to 3 substituents, said substituents being the same or different from one another and selected from the group consisting of a halogen atom, lower alkyl group, lower alkoxy group, hydroxyl group, protected hydroxyl group, carboxyl group, esterified carboxyl group, amidated carboxyl group, lower alkylthio group and phenoxy group.

* * * * *